(12) United States Patent
Gurskis et al.

(10) Patent No.: US 8,821,569 B2
(45) Date of Patent: Sep. 2, 2014

(54) MULTIPLE COMPONENT PROSTHETIC HEART VALVE ASSEMBLIES AND METHODS FOR DELIVERING THEM

(75) Inventors: Donnell W. Gurskis, Belmont, CA (US); Mimi Nguyen-Fitterer, Redwood City, CA (US); Takashi Harry Ino, San Jose, CA (US)

(73) Assignee: Medtronic, Inc., Minneapolis, MN (US)

( * ) Notice: Subject to any disclaimer, the term of this patent is extended or adjusted under 35 U.S.C. 154(b) by 1299 days.

(21) Appl. No.: 11/742,481

(22) Filed: Apr. 30, 2007

(65) Prior Publication Data

US 2007/0288089 A1 Dec. 13, 2007

Related U.S. Application Data

(60) Provisional application No. 60/746,038, filed on Apr. 29, 2006, provisional application No. 60/914,742, filed on Apr. 29, 2007.

(51) Int. Cl.
*A61F 2/24* (2006.01)
(52) U.S. Cl.
USPC .......................................... 623/2.11; 623/2.4
(58) Field of Classification Search
USPC .............. 623/2.11, 2.17, 2.22–2.32, 2.4, 2.41
See application file for complete search history.

(56) References Cited

U.S. PATENT DOCUMENTS

| | | |
|---|---|---|
| 1,023,184 A | 4/1912 | Watts et al. |
| 1,124,025 A | 4/1915 | Johnson |
| 2,023,100 A | 12/1935 | Rose |
| 2,231,314 A | 2/1941 | Amour |
| 3,143,742 A | 8/1964 | Cromie |
| 3,320,974 A | 5/1967 | High et al. |
| 3,370,305 A | 2/1968 | Goott et al. |
| 3,371,352 A | 3/1968 | Siposs |
| 3,409,013 A | 11/1968 | Berry |
| 3,461,733 A * | 8/1969 | Peterson ....................... 474/256 |

(Continued)

FOREIGN PATENT DOCUMENTS

| | | |
|---|---|---|
| CN | 2356656 | 1/2000 |
| DE | 19532973 | 11/1996 |

(Continued)

OTHER PUBLICATIONS

Tascon, "Prosthetic Heart Valves: Design Considerations," Ann. Thorac. Surgery, 48:S16-S17 (1989).

(Continued)

*Primary Examiner* — Dianne Dornbusch
*Assistant Examiner* — Robert Lynch

(57) ABSTRACT

Multiple component heart valves and apparatus and methods for implanting them are provided. The heart valve generally includes a first annular prosthesis and a second valve prosthesis. The first prosthesis includes an annular member compressible from a relaxed condition to a contracted condition to facilitate delivery into a biological annulus, the annular member being resiliently expandable towards the relaxed condition. The first prosthesis also includes guide rails extending therefrom. The second prosthesis includes an annular frame, valve elements, and receptacles for receiving respective guide rails therethrough when the second prosthesis is directed towards the first prosthesis. In addition, a valve holder may releasably carry the valve prosthesis that includes channels for receiving respective guide rails therethrough when the guide rails are received through the valve prosthesis. A delivery tool is also provided that includes an actuator for selectively compressing the annular member into the contracted condition.

17 Claims, 45 Drawing Sheets

(56) References Cited

U.S. PATENT DOCUMENTS

| | | |
|---|---|---|
| 3,464,065 A | 9/1969 | Cromie |
| 3,546,710 A | 12/1970 | Ivanovich et al. |
| 3,571,815 A | 3/1971 | Somyk |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |
| 3,691,567 A | 9/1972 | Cromie |
| 3,710,744 A | 1/1973 | Goodenough et al. |
| 3,744,060 A | 7/1973 | Bellhouse et al. |
| 3,755,823 A | 9/1973 | Hancock |
| 3,800,403 A | 4/1974 | Anderson |
| 3,839,741 A | 10/1974 | Haller |
| 3,890,975 A | 6/1975 | McGregor |
| 3,939,741 A | 2/1976 | Allan |
| 3,959,827 A | 6/1976 | Kaster |
| 3,974,854 A | 8/1976 | Kurpanek |
| 3,996,623 A | 12/1976 | Kaster |
| 3,997,923 A | 12/1976 | Possis |
| 4,035,849 A | 7/1977 | Angell et al. |
| 4,054,144 A | 10/1977 | Hoffman et al. |
| 4,078,268 A | 3/1978 | Possis |
| 4,078,468 A | 3/1978 | Civitello |
| 4,084,268 A * | 4/1978 | Ionescu et al. ............... 623/2.15 |
| 4,106,129 A | 8/1978 | Carpentier et al. |
| 4,140,126 A | 2/1979 | Choudhury |
| 4,164,046 A | 8/1979 | Cooley |
| 4,172,295 A | 10/1979 | Batten |
| 4,211,325 A | 7/1980 | Wright |
| 4,217,665 A | 8/1980 | Bex et al. |
| 4,218,782 A | 8/1980 | Rygg |
| 4,245,358 A | 1/1981 | Moasser |
| 4,259,753 A | 4/1981 | Liotta et al. |
| 4,291,420 A | 9/1981 | Reul |
| 4,297,749 A | 11/1981 | Davis et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,477,930 A | 10/1984 | Totten et al. |
| 4,485,816 A | 12/1984 | Krumme |
| 4,501,030 A | 2/1985 | Lane |
| 4,506,394 A | 3/1985 | Bedard |
| 4,535,483 A | 8/1985 | Klawitter et al. |
| 4,548,202 A | 10/1985 | Duncan |
| 4,605,407 A | 8/1986 | Black et al. |
| 4,626,255 A | 12/1986 | Reichart et al. |
| 4,629,459 A | 12/1986 | Ionescu et al. |
| 4,665,906 A | 5/1987 | Jervis |
| 4,666,442 A | 5/1987 | Arru et al. |
| 4,680,031 A | 7/1987 | Alonso |
| 4,683,883 A | 8/1987 | Martin |
| 4,687,483 A | 8/1987 | Fisher et al. |
| 4,692,164 A | 9/1987 | Dzemeshkievich et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,743,253 A | 5/1988 | Magladry |
| 4,758,151 A | 7/1988 | Arru et al. |
| 4,775,378 A | 10/1988 | Knoch et al. |
| 4,778,461 A | 10/1988 | Pietsch et al. |
| 4,790,843 A | 12/1988 | Carpentier et al. |
| 4,816,029 A | 3/1989 | Penny, III et al. |
| 4,851,000 A | 7/1989 | Gupta |
| 4,865,600 A | 9/1989 | Carpentier et al. |
| 4,888,009 A | 12/1989 | Lederman et al. |
| 4,892,541 A | 1/1990 | Alonso |
| 4,914,097 A | 4/1990 | Oda et al. |
| 4,917,698 A | 4/1990 | Carpentier et al. |
| 4,935,030 A | 6/1990 | Alonso |
| 4,960,424 A | 10/1990 | Grooters |
| 4,993,428 A | 2/1991 | Arms |
| 4,994,077 A | 2/1991 | Dobben |
| 5,002,567 A | 3/1991 | Bona et al. |
| 5,010,892 A | 4/1991 | Colvin et al. |
| 5,032,128 A | 7/1991 | Alonso |
| 5,035,709 A | 7/1991 | Wieting et al. |
| 5,037,434 A | 8/1991 | Lane |
| 5,071,431 A | 12/1991 | Sauter et al. |
| 5,104,406 A | 4/1992 | Curcio et al. |
| 5,147,391 A | 9/1992 | Lane |
| 5,163,953 A | 11/1992 | Vince |
| 5,163,954 A | 11/1992 | Curcio et al. |
| 5,163,955 A | 11/1992 | Love et al. |
| 5,178,633 A | 1/1993 | Peters |
| 5,192,303 A | 3/1993 | Gatturna |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,370,685 A | 12/1994 | Stevens |
| 5,376,112 A | 12/1994 | Duran |
| 5,396,887 A | 3/1995 | Imran |
| 5,397,346 A | 3/1995 | Walker et al. |
| 5,397,348 A | 3/1995 | Campbell et al. |
| 5,397,351 A | 3/1995 | Pavcnik et al. |
| 5,406,857 A | 4/1995 | Eberhardt et al. |
| 5,411,552 A | 5/1995 | Andersen et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,531,784 A | 7/1996 | Love et al. |
| 5,533,515 A | 7/1996 | Coller et al. |
| 5,549,665 A * | 8/1996 | Vesely et al. ............... 623/2.14 |
| 5,549,666 A | 8/1996 | Hata et al. |
| 5,554,185 A | 9/1996 | Block et al. |
| 5,562,729 A | 10/1996 | Purdy et al. |
| 5,571,175 A | 11/1996 | Vanney |
| 5,571,215 A | 11/1996 | Sterman et al. |
| 5,573,007 A | 11/1996 | Bobo, Sr. |
| 5,573,543 A | 11/1996 | Akopov |
| 5,578,076 A | 11/1996 | Krueger et al. |
| 5,584,803 A | 12/1996 | Stevens et al. |
| 5,607,470 A | 3/1997 | Milo |
| 5,613,982 A | 3/1997 | Goldstein |
| 5,618,307 A | 4/1997 | Donlon et al. |
| 5,626,607 A | 5/1997 | Malecki et al. |
| 5,628,789 A | 5/1997 | Vanney et al. |
| 5,662,704 A | 9/1997 | Gross |
| 5,669,917 A | 9/1997 | Sauer |
| 5,693,090 A | 12/1997 | Unsworth et al. |
| 5,695,503 A | 12/1997 | Krueger et al. |
| 5,713,952 A | 2/1998 | Vanney et al. |
| 5,713,953 A | 2/1998 | Vallana et al. |
| 5,716,370 A | 2/1998 | Williamson et al. |
| 5,716,399 A | 2/1998 | Love |
| 5,720,755 A | 2/1998 | Dakov |
| 5,725,554 A | 3/1998 | Simon |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,807,405 A | 9/1998 | Vanney et al. |
| 5,814,097 A | 9/1998 | Sterman et al. |
| 5,814,098 A | 9/1998 | Hinnenkamp et al. |
| 5,814,100 A | 9/1998 | Carpentier et al. |

(56) References Cited

U.S. PATENT DOCUMENTS

| | | |
|---|---|---|
| 5,824,060 A | 10/1998 | Christie et al. |
| 5,824,061 A | 10/1998 | Quijano et al. |
| 5,824,064 A | 10/1998 | Taheri |
| 5,830,239 A | 11/1998 | Toomes |
| 5,840,081 A | 11/1998 | Andersen et al. |
| 5,843,179 A | 12/1998 | Vanney et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,603 A | 1/1999 | Reif |
| 5,860,992 A | 1/1999 | Daniel |
| 5,861,028 A | 1/1999 | Angell |
| 5,865,801 A | 2/1999 | Houser |
| 5,871,489 A * | 2/1999 | Ovil ........................ 606/148 |
| 5,873,906 A | 2/1999 | Lau et al. |
| 5,876,436 A | 3/1999 | Vanney et al. |
| 5,879,371 A | 3/1999 | Gardiner et al. |
| 5,891,160 A | 4/1999 | Williamson, IV et al. |
| 5,891,195 A | 4/1999 | Klostermeyer et al. |
| 5,895,420 A | 4/1999 | Mirsch, II et al. |
| 5,902,308 A | 5/1999 | Murphy |
| 5,908,450 A | 6/1999 | Gross et al. |
| 5,908,452 A | 6/1999 | Bokros et al. |
| 5,910,170 A | 6/1999 | Reimink et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,925,061 A | 7/1999 | Ogi et al. |
| 5,925,063 A | 7/1999 | Khosravi |
| 5,931,969 A | 8/1999 | Carpentier et al. |
| 5,935,163 A | 8/1999 | Gabbay |
| 5,957,940 A | 9/1999 | Tanner et al. |
| 5,957,949 A | 9/1999 | Leonhardt et al. |
| 5,961,549 A | 10/1999 | Nguyen et al. |
| 5,961,550 A | 10/1999 | Carpentier |
| 5,972,004 A | 10/1999 | Williamson, IV et al. |
| 5,972,024 A | 10/1999 | Northrup, III |
| 5,976,183 A | 11/1999 | Ritz |
| 5,984,959 A | 11/1999 | Robertson et al. |
| 5,984,973 A | 11/1999 | Girard et al. |
| 6,007,577 A | 12/1999 | Vanney et al. |
| 6,010,531 A | 1/2000 | Donlon et al. |
| 6,042,607 A | 3/2000 | Williamson, IV et al. |
| 6,045,576 A | 4/2000 | Starr et al. |
| 6,059,827 A | 5/2000 | Fenton, Jr. |
| 6,066,160 A | 5/2000 | Colvin et al. |
| 6,068,657 A | 5/2000 | Lapeyre et al. |
| 6,074,041 A | 6/2000 | Imanaka et al. |
| 6,074,417 A | 6/2000 | Peredo |
| 6,074,418 A | 6/2000 | Buchanan et al. |
| 6,081,737 A | 6/2000 | Shah |
| 6,083,179 A | 7/2000 | Oredsson |
| 6,096,074 A | 8/2000 | Pedros |
| 6,099,475 A | 8/2000 | Seward et al. |
| 6,102,944 A | 8/2000 | Huynh |
| 6,106,550 A | 8/2000 | Magovern et al. |
| 6,110,200 A | 8/2000 | Hinnenkamp |
| 6,113,632 A | 9/2000 | Reif |
| 6,117,091 A | 9/2000 | Young et al. |
| 6,126,007 A | 10/2000 | Kari et al. |
| 6,129,758 A | 10/2000 | Love |
| 6,139,575 A | 10/2000 | Shu et al. |
| 6,143,024 A | 11/2000 | Campbell et al. |
| 6,143,025 A | 11/2000 | Stobie et al. |
| 6,149,658 A | 11/2000 | Gardiner et al. |
| 6,152,935 A | 11/2000 | Kammerer et al. |
| 6,162,233 A | 12/2000 | Williamson, IV et al. |
| 6,165,183 A | 12/2000 | Kuehn et al. |
| 6,168,614 B1 | 1/2001 | Andersen et al. |
| 6,176,877 B1 | 1/2001 | Buchanan et al. |
| 6,176,977 B1 | 1/2001 | Taylor et al. |
| 6,183,512 B1 | 2/2001 | Hawanec, Jr. et al. |
| 6,197,054 B1 | 3/2001 | Hamblin, Jr. et al. |
| 6,200,306 B1 | 3/2001 | Klostermeyer |
| 6,203,553 B1 | 3/2001 | Robertson |
| 6,214,043 B1 | 4/2001 | Krueger et al. |
| 6,217,610 B1 | 4/2001 | Carpentier et al. |
| 6,217,611 B1 | 4/2001 | Klostermeyer |
| 6,231,561 B1 | 5/2001 | Frazier et al. |
| 6,231,602 B1 | 5/2001 | Carpentier et al. |
| 6,241,765 B1 | 6/2001 | Griffin et al. |
| 6,245,102 B1 | 6/2001 | Jayaraman |
| 6,245,105 B1 | 6/2001 | Nguyen et al. |
| 6,254,636 B1 | 7/2001 | Peredo |
| 6,264,691 B1 | 7/2001 | Gabbay |
| 6,270,526 B1 | 8/2001 | Cox |
| 6,270,527 B1 | 8/2001 | Campbell et al. |
| 6,283,127 B1 | 9/2001 | Sterman et al. |
| 6,283,995 B1 | 9/2001 | Moe et al. |
| 6,287,339 B1 | 9/2001 | Vazquez et al. |
| 6,290,674 B1 | 9/2001 | Roue et al. |
| 6,299,638 B1 | 10/2001 | Sauter |
| 6,309,417 B1 | 10/2001 | Spence |
| 6,312,447 B1 | 11/2001 | Grimes |
| 6,312,465 B1 | 11/2001 | Griffin et al. |
| 6,319,280 B1 | 11/2001 | Schoon |
| 6,319,281 B1 | 11/2001 | Patel |
| 6,322,588 B1 | 11/2001 | Ogle et al. |
| 6,328,727 B1 | 12/2001 | Frazier et al. |
| 6,328,763 B1 | 12/2001 | Love et al. |
| 6,334,446 B1 | 1/2002 | Beyar |
| 6,338,740 B1 | 1/2002 | Carpentier |
| 6,350,281 B1 | 2/2002 | Rhee |
| 6,358,278 B1 | 3/2002 | Brendzel et al. |
| 6,358,556 B1 | 3/2002 | Ding et al. |
| 6,371,983 B1 | 4/2002 | Lane |
| 6,391,053 B1 | 5/2002 | Brendzel et al. |
| 6,395,025 B1 | 5/2002 | Fordenbacher et al. |
| 6,402,780 B2 | 6/2002 | Williamson, IV et al. |
| 6,409,759 B1 | 6/2002 | Peredo |
| 6,413,275 B1 | 7/2002 | Nguyen et al. |
| 6,419,696 B1 | 7/2002 | Ortiz et al. |
| 6,425,902 B1 | 7/2002 | Love |
| 6,425,916 B1 | 7/2002 | Garrison et al. |
| 6,440,164 B1 | 8/2002 | DiMatteo et al. |
| 6,447,524 B1 | 9/2002 | Knodel |
| 6,454,799 B1 * | 9/2002 | Schreck ................... 623/2.18 |
| 6,458,153 B1 | 10/2002 | Bailey et al. |
| 6,461,382 B1 | 10/2002 | Cao |
| 6,468,305 B1 | 10/2002 | Otte |
| 6,503,272 B2 | 1/2003 | Duerig et al. |
| 6,514,265 B2 | 2/2003 | Ho et al. |
| 6,530,952 B2 | 3/2003 | Vesely |
| 6,547,827 B2 | 4/2003 | Carpentier et al. |
| 6,551,332 B1 | 4/2003 | Nguyen et al. |
| 6,558,418 B2 | 5/2003 | Carpentier et al. |
| 6,569,196 B1 | 5/2003 | Vesely |
| 6,582,462 B1 | 6/2003 | Andersen et al. |
| 6,585,766 B1 | 7/2003 | Huynh et al. |
| 6,589,279 B1 | 7/2003 | Anderson et al. |
| 6,598,307 B2 | 7/2003 | Love et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,613,085 B1 | 9/2003 | Anderson et al. |
| 6,641,593 B1 | 11/2003 | Schaller et al. |
| 6,652,578 B2 | 11/2003 | Bailey et al. |
| 6,660,032 B2 | 12/2003 | Klumb et al. |
| 6,676,671 B2 | 1/2004 | Robertson et al. |
| 6,678,962 B1 | 1/2004 | Love et al. |
| 6,682,559 B2 | 1/2004 | Myers et al. |
| 6,685,739 B2 | 2/2004 | DiMatteo et al. |
| 6,692,513 B2 | 2/2004 | Streeter et al. |
| 6,695,859 B1 | 2/2004 | Golden et al. |
| 6,709,457 B1 | 3/2004 | Otte et al. |
| 6,716,243 B1 | 4/2004 | Colvin et al. |
| 6,716,244 B2 | 4/2004 | Klaco |
| 6,719,789 B2 | 4/2004 | Cox |
| 6,719,790 B2 | 4/2004 | Brendzel et al. |
| 6,730,118 B2 | 5/2004 | Spenser et al. |
| 6,733,525 B2 | 5/2004 | Yang et al. |
| 6,764,508 B1 | 7/2004 | Roehe et al. |
| 6,767,362 B2 * | 7/2004 | Schreck ................... 623/2.11 |

(56) References Cited

U.S. PATENT DOCUMENTS

| | | |
|---|---|---|
| 6,769,434 B2 | 8/2004 | Liddicoat et al. |
| 6,776,785 B1 | 8/2004 | Yencho |
| 6,786,924 B2 | 9/2004 | Ryan et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,830,585 B1 | 12/2004 | Artof et al. |
| 6,833,924 B2 | 12/2004 | Love et al. |
| 6,837,902 B2 | 1/2005 | Nguyen et al. |
| 6,846,324 B2 | 1/2005 | Stobie |
| 6,846,325 B2 | 1/2005 | Liddicoat |
| 6,872,226 B2 | 3/2005 | Cali et al. |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,908,481 B2 | 6/2005 | Cribier |
| 6,911,043 B2 | 6/2005 | Myers et al. |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,929,653 B2 | 8/2005 | Strecter |
| 6,939,365 B1 | 9/2005 | Fogarty |
| 6,945,980 B2 | 9/2005 | Nguyen et al. |
| 6,945,997 B2 | 9/2005 | Huynh et al. |
| 6,960,221 B2 | 11/2005 | Ho et al. |
| 6,966,925 B2 * | 11/2005 | Stobie ............... 623/2.11 |
| 6,974,476 B2 | 12/2005 | McGuckin et al. |
| 7,011,681 B2 | 3/2006 | Vesely |
| 7,025,780 B2 | 4/2006 | Gabbay |
| 7,037,333 B2 | 5/2006 | Myers et al. |
| 7,070,616 B2 | 7/2006 | Majercak et al. |
| 7,083,648 B2 | 8/2006 | Yu |
| 7,097,659 B2 | 8/2006 | Woolfson et al. |
| 7,101,396 B2 | 9/2006 | Artof et al. |
| 7,137,184 B2 | 11/2006 | Schreck |
| 7,141,064 B2 | 11/2006 | Scott et al. |
| 7,147,663 B1 | 12/2006 | Berg et al. |
| 7,153,324 B2 | 12/2006 | Case et al. |
| 7,172,625 B2 | 2/2007 | Shu et al. |
| 7,175,659 B2 * | 2/2007 | Hill et al. ............... 623/2.11 |
| 7,179,290 B2 | 2/2007 | Cao |
| 7,182,769 B2 | 2/2007 | Ainsworth et al. |
| 7,186,265 B2 | 3/2007 | Sharkawy et al. |
| 7,195,641 B2 | 3/2007 | Palmaz et al. |
| 7,201,761 B2 | 4/2007 | Woolfson et al. |
| 7,201,771 B2 | 4/2007 | Lane |
| 7,201,772 B2 | 4/2007 | Schwammenthal et al. |
| 7,214,344 B2 | 5/2007 | Carpentier et al. |
| 7,238,200 B2 | 7/2007 | Lee et al. |
| 7,252,682 B2 | 8/2007 | Seguin |
| 7,261,732 B2 | 8/2007 | Justino |
| 7,300,463 B2 | 11/2007 | Liddicoat |
| RE40,377 E | 6/2008 | Williamson, IV et al. |
| 7,381,218 B2 * | 6/2008 | Schreck ............... 623/1.26 |
| 7,393,360 B2 | 7/2008 | Spenser et al. |
| 7,422,603 B2 | 9/2008 | Lane |
| 7,445,632 B2 | 11/2008 | McGuckin et al. |
| 7,513,909 B2 | 4/2009 | Lane et al. |
| 7,547,313 B2 | 6/2009 | Gardiner et al. |
| 7,556,647 B2 | 7/2009 | Drews et al. |
| 7,566,343 B2 | 7/2009 | Jenson et al. |
| 7,578,843 B2 | 8/2009 | Shu |
| 7,597,710 B2 | 10/2009 | Obermiller |
| 7,597,711 B2 | 10/2009 | Drews et al. |
| 7,670,370 B2 * | 3/2010 | Hill et al. ............... 623/2.11 |
| 7,708,775 B2 | 5/2010 | Rowe et al. |
| 7,717,955 B2 | 5/2010 | Lane et al. |
| 7,722,643 B2 | 5/2010 | Ho et al. |
| 7,744,611 B2 | 6/2010 | Nguyen et al. |
| 7,763,040 B2 | 7/2010 | Schaller et al. |
| 7,771,469 B2 | 8/2010 | Liddicoat et al. |
| 7,803,184 B2 | 9/2010 | McGuckin et al. |
| 8,021,421 B2 * | 9/2011 | Fogarty et al. ............... 623/2.38 |
| 2001/0007956 A1 | 7/2001 | Letac et al. |
| 2001/0018592 A1 | 8/2001 | Schaller et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044656 A1 | 11/2001 | Williamson, IV et al. |
| 2001/0049492 A1 | 12/2001 | Frazier et al. |
| 2002/0026238 A1 | 2/2002 | Lane et al. |
| 2002/0032480 A1 | 3/2002 | Spence et al. |
| 2002/0032481 A1 | 3/2002 | Gabbay |
| 2002/0035361 A1 | 3/2002 | Houser et al. |
| 2002/0055774 A1 | 5/2002 | Liddicoat |
| 2002/0058994 A1 | 5/2002 | Hill et al. |
| 2002/0058995 A1 | 5/2002 | Stevens |
| 2002/0077555 A1 | 6/2002 | Schwartz |
| 2002/0077698 A1 | 6/2002 | Peredo |
| 2002/0091441 A1 | 7/2002 | Nguyen et al. |
| 2002/0116054 A1 | 8/2002 | Lundell et al. |
| 2002/0123802 A1 | 9/2002 | Snyders |
| 2002/0128684 A1 | 9/2002 | Foerster |
| 2002/0138138 A1 | 9/2002 | Yang |
| 2002/0151970 A1 | 10/2002 | Garrison et al. |
| 2002/0173842 A1 | 11/2002 | Buchanan |
| 2002/0177223 A1 | 11/2002 | Ogle et al. |
| 2002/0183834 A1 | 12/2002 | Klaco |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023302 A1 | 1/2003 | Moe et al. |
| 2003/0023303 A1 | 1/2003 | Palmaz et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0045902 A1 | 3/2003 | Weadeock |
| 2003/0050693 A1 | 3/2003 | Quijano et al. |
| 2003/0055495 A1 | 3/2003 | Pease et al. |
| 2003/0109922 A1 | 6/2003 | Peterson et al. |
| 2003/0109924 A1 | 6/2003 | Cribier |
| 2003/0114913 A1 | 6/2003 | Spenser et al. |
| 2003/0125793 A1 | 7/2003 | Vesely |
| 2003/0130729 A1 | 7/2003 | Paniagua et al. |
| 2003/0136417 A1 | 7/2003 | Fonseca et al. |
| 2003/0149477 A1 | 8/2003 | Gabbay |
| 2003/0149478 A1 | 8/2003 | Figulla et al. |
| 2003/0153974 A1 | 8/2003 | Spenser et al. |
| 2003/0167089 A1 | 9/2003 | Lane |
| 2003/0191481 A1 | 10/2003 | Nguyen et al. |
| 2003/0199963 A1 | 10/2003 | Tower et al. |
| 2003/0199971 A1 | 10/2003 | Tower et al. |
| 2003/0199974 A1 | 10/2003 | Lee et al. |
| 2003/0229394 A1 | 12/2003 | Ogle et al. |
| 2003/0236568 A1 | 12/2003 | Hojeibane et al. |
| 2004/0015232 A1 | 1/2004 | Shu |
| 2004/0019374 A1 | 1/2004 | Hojeibane et al. |
| 2004/0024452 A1 | 2/2004 | Kruse et al. |
| 2004/0030381 A1 | 2/2004 | Shu |
| 2004/0034411 A1 | 2/2004 | Quijano et al. |
| 2004/0039436 A1 | 2/2004 | Spenser et al. |
| 2004/0044406 A1 | 3/2004 | Woolfson et al. |
| 2004/0050393 A1 | 3/2004 | Golden et al. |
| 2004/0068276 A1 | 4/2004 | Golden et al. |
| 2004/0078074 A1 | 4/2004 | Anderson et al. |
| 2004/0093075 A1 | 5/2004 | Kuehne |
| 2004/0102797 A1 | 5/2004 | Golden et al. |
| 2004/0106976 A1 | 6/2004 | Bailey et al. |
| 2004/0106990 A1 | 6/2004 | Spence et al. |
| 2004/0122514 A1 | 6/2004 | Fogarty |
| 2004/0122516 A1 | 6/2004 | Fogarty |
| 2004/0122526 A1 | 6/2004 | Imran |
| 2004/0167573 A1 | 8/2004 | Williamson, IV et al. |
| 2004/0167620 A1 | 8/2004 | Ortiz et al. |
| 2004/0176839 A1 | 9/2004 | Huynh et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0199176 A1 | 10/2004 | Berreklouw |

(56) References Cited

U.S. PATENT DOCUMENTS

| | | |
|---|---|---|
| 2004/0206363 A1 | 10/2004 | McCarthy et al. |
| 2004/0210304 A1 | 10/2004 | Seguin et al. |
| 2004/0210305 A1 | 10/2004 | Shu |
| 2004/0210307 A1 | 10/2004 | Khairkhahan |
| 2004/0225355 A1 | 11/2004 | Stevens |
| 2004/0225356 A1 | 11/2004 | Frater |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1* | 2/2005 | Fogarty et al. .............. 606/224 |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065601 A1 | 3/2005 | Lee et al. |
| 2005/0065614 A1 | 3/2005 | Stinson |
| 2005/0070923 A1* | 3/2005 | McIntosh .................... 606/139 |
| 2005/0070924 A1 | 3/2005 | Schaller et al. |
| 2005/0075584 A1 | 4/2005 | Cali |
| 2005/0075659 A1 | 4/2005 | Realyvasquez et al. |
| 2005/0075667 A1 | 4/2005 | Ho et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075730 A1 | 4/2005 | Myers et al. |
| 2005/0080454 A1 | 4/2005 | Drews |
| 2005/0096738 A1 | 5/2005 | Cali et al. |
| 2005/0098547 A1 | 5/2005 | Cali et al. |
| 2005/0101975 A1 | 5/2005 | Nguyen et al. |
| 2005/0107871 A1 | 5/2005 | Realyvasquez et al. |
| 2005/0131429 A1 | 6/2005 | Ho et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137702 A1 | 6/2005 | Haug et al. |
| 2005/0150775 A1 | 7/2005 | Zhang et al. |
| 2005/0159811 A1 | 7/2005 | Lane |
| 2005/0165477 A1 | 7/2005 | Andruiza et al. |
| 2005/0165479 A1 | 7/2005 | Lane |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkaway et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0240263 A1* | 10/2005 | Fogarty et al. .............. 623/2.38 |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0004389 A1 | 1/2006 | Nguyen et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino |
| 2006/0122692 A1 | 6/2006 | Gilad et al. |
| 2006/0135964 A1 | 6/2006 | Vesely |
| 2006/0136052 A1 | 6/2006 | Vesely |
| 2006/0136054 A1 | 6/2006 | Berg et al. |
| 2006/0149360 A1 | 7/2006 | Schwammenthal et al. |
| 2006/0149367 A1 | 7/2006 | Sieracki |
| 2006/0154230 A1 | 7/2006 | Cunanan |
| 2006/0161249 A1 | 7/2006 | Realyvasquez et al. |
| 2006/0167543 A1 | 7/2006 | Bailey et al. |
| 2006/0173537 A1 | 8/2006 | Yang et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0276888 A1 | 12/2006 | Lee |
| 2006/0287717 A1* | 12/2006 | Rowe et al. .................. 623/2.11 |
| 2006/0287719 A1* | 12/2006 | Rowe et al. .................. 623/2.18 |
| 2007/0005129 A1 | 1/2007 | Damm et al. |
| 2007/0010835 A1 | 1/2007 | Breton et al. |
| 2007/0010876 A1 | 1/2007 | Salahieh et al. |
| 2007/0010877 A1 | 1/2007 | Salahieh et al. |
| 2007/0016285 A1 | 1/2007 | Lane |
| 2007/0016286 A1 | 1/2007 | Herrmann et al. |
| 2007/0016288 A1 | 1/2007 | Gurskis |
| 2007/0027461 A1 | 2/2007 | Gardiner et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0095698 A1 | 5/2007 | Cambron |
| 2007/0100440 A1 | 5/2007 | Figulla et al. |
| 2007/0106313 A1 | 5/2007 | Golden et al. |
| 2007/0129794 A1 | 6/2007 | Realyvasquez |
| 2007/0129795 A1 | 6/2007 | Hill et al. |
| 2007/0142848 A1 | 6/2007 | Ainsworth et al. |
| 2007/0142906 A1 | 6/2007 | Figulla et al. |
| 2007/0142907 A1 | 6/2007 | Moaddeb et al. |
| 2007/0150053 A1 | 6/2007 | Gurskis |
| 2007/0156233 A1 | 7/2007 | Kapadia et al. |
| 2007/0162103 A1 | 7/2007 | Case et al. |
| 2007/0162107 A1* | 7/2007 | Haug et al. .................. 623/1.26 |
| 2007/0162111 A1 | 7/2007 | Fukamachi et al. |
| 2007/0162113 A1 | 7/2007 | Sharkawy et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288089 A1 | 12/2007 | Gurskis et al. |
| 2008/0004696 A1 | 1/2008 | Vesely |
| 2008/0033543 A1 | 2/2008 | Gurskis et al. |
| 2008/0071361 A1 | 3/2008 | Tuval et al. |
| 2008/0071369 A1 | 3/2008 | Tuval et al. |
| 2008/0097595 A1 | 4/2008 | Gabbay |
| 2008/0119875 A1 | 5/2008 | Ino et al. |
| 2008/0281411 A1 | 11/2008 | Berreklouw |
| 2008/0319543 A1 | 12/2008 | Lane |
| 2009/0036903 A1 | 2/2009 | Ino et al. |

(56) References Cited

U.S. PATENT DOCUMENTS

| | | |
|---|---|---|
| 2009/0112233 A1 | 4/2009 | Xiao |
| 2009/0192599 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0210052 A1 | 8/2009 | Forster et al. |
| 2009/0264903 A1 | 10/2009 | Lee et al. |
| 2009/0319038 A1 | 12/2009 | Gurskis et al. |
| 2010/0030244 A1 | 2/2010 | Woolfson et al. |
| 2010/0044410 A1 | 2/2010 | Argentine et al. |
| 2010/0100174 A1 | 4/2010 | Gurskis |
| 2010/0249894 A1 | 9/2010 | Oba et al. |

FOREIGN PATENT DOCUMENTS

| | | |
|---|---|---|
| EP | 0 084 395 | 8/1986 |
| EP | 0 096 721 | 12/1987 |
| EP | 0 125 393 | 12/1987 |
| EP | 0 179 562 | 7/1989 |
| EP | 0 826 340 | 3/1998 |
| EP | 0 850 607 | 7/1998 |
| EP | 1057460 | 12/2000 |
| EP | 1 088 529 | 4/2001 |
| EP | 971 650 | 1/2005 |
| EP | 171 059 | 2/2005 |
| EP | 1171059 | 11/2005 |
| GB | 1093599 | 12/1967 |
| GB | 1477643 | 6/1977 |
| GB | 2011259 | 7/1979 |
| GB | 2 056 023 | 3/1981 |
| GB | 2 069 843 | 9/1981 |
| GB | 2254254 | 10/1992 |
| GB | 2 279 134 | 12/1994 |
| SU | 1116573 | 7/1985 |
| WO | WO 87/05489 | 9/1987 |
| WO | WO 89/00084 | 2/1989 |
| WO | WO 91/15167 | 10/1991 |
| WO | WO 92/01269 | 8/1992 |
| WO | WO 92/13502 | 8/1992 |
| WO | WO 92/19184 | 11/1992 |
| WO | WO 92/19185 | 11/1992 |
| WO | WO 95/17139 | 6/1995 |
| WO | WO 95/28899 | 11/1995 |
| WO | WO 96/40006 | 12/1996 |
| WO | WO 97/09933 | 3/1997 |
| WO | WO 97/09944 | 3/1997 |
| WO | WO 97/27799 | 8/1997 |
| WO | WO 97/41801 | 11/1997 |
| WO | WO 97/42871 | 11/1997 |
| WO | WO 98/06329 | 2/1998 |
| WO | WO 99/11201 | 3/1999 |
| WO | WO 99/15112 | 4/1999 |
| WO | WO 99/51169 | 10/1999 |
| WO | WO 00/32105 | 6/2000 |
| WO | WO 00/40176 | 7/2000 |
| WO | WO 00/44311 | 8/2000 |
| WO | WO 00/47139 | 8/2000 |
| WO | WO 00/56250 | 9/2000 |
| WO | WO 00/59382 | 10/2000 |
| WO | WO 00/60995 | 10/2000 |
| WO | WO 00/64380 | 11/2000 |
| WO | WO 01/10310 | 2/2001 |
| WO | WO 01/10312 | 2/2001 |
| WO | WO 01/49217 | 7/2001 |
| WO | WO 01/58363 | 8/2001 |
| WO | WO 01/76510 | 10/2001 |
| WO | WO 01/82840 | 11/2001 |
| WO | WO 01/87190 | 11/2001 |
| WO | WO 03/011195 | 2/2003 |
| WO | WO 03/063740 | 8/2003 |
| WO | WO 2004/006810 | 1/2004 |
| WO | WO 2004/089246 | 10/2004 |
| WO | WO 2005/004753 | 1/2005 |
| WO | WO 2005/020842 | 3/2005 |
| WO | WO 2005/039452 | 5/2005 |
| WO | WO 2005/072655 | 8/2005 |
| WO | WO 2006/086135 | 8/2006 |
| WO | WO 2009/137517 | 11/2009 |

OTHER PUBLICATIONS

Jansen, et al., "Detachable Shape-Memory Sewing Ring for Heart Valves," Artif. Organs. vol. 16, No. 3, 1992, pp. 294-297, Helmholtz Institute for Biomedical Engineering, Technical University of Aachen, Aachn, Germany.

Lutter, et al., Percutaneous Valve Replacement: Current State and Future Prospects; Ann. Thorac. Suig. 2004; 78: 2199-2206.

English language abstract of Chinese Patent Publication No. CN 2356656, European Patent Office, Espacenet database—Worldwide, (2012).

English language abstract of European Patent Publication No. EP 171 059, European Patent Office, Espacenet Patent Translate (2012).

\* cited by examiner

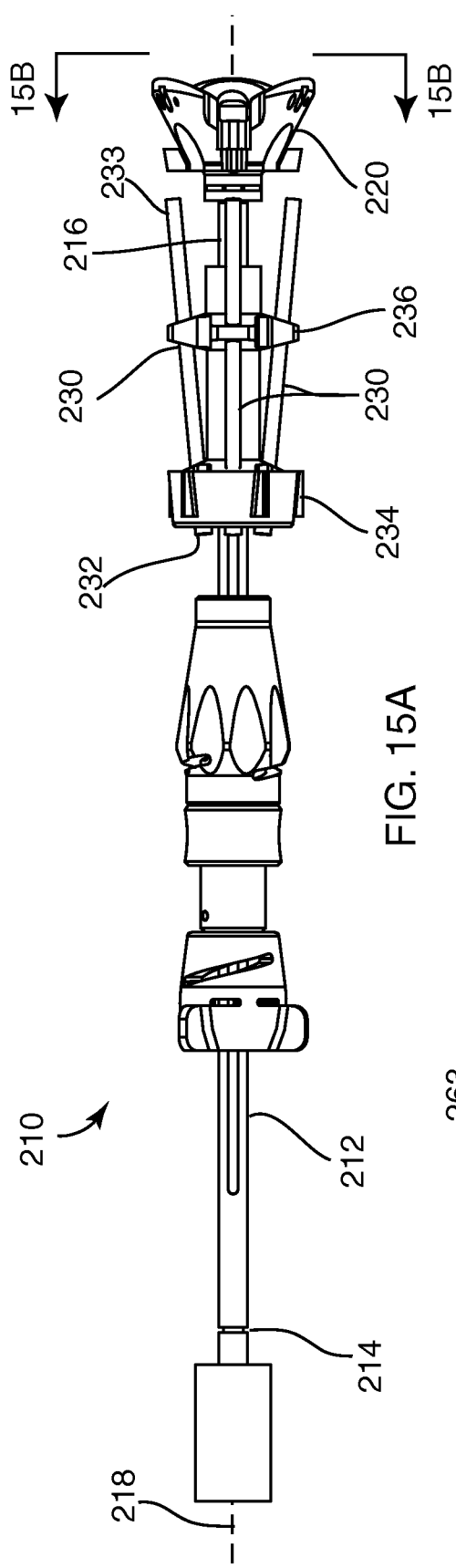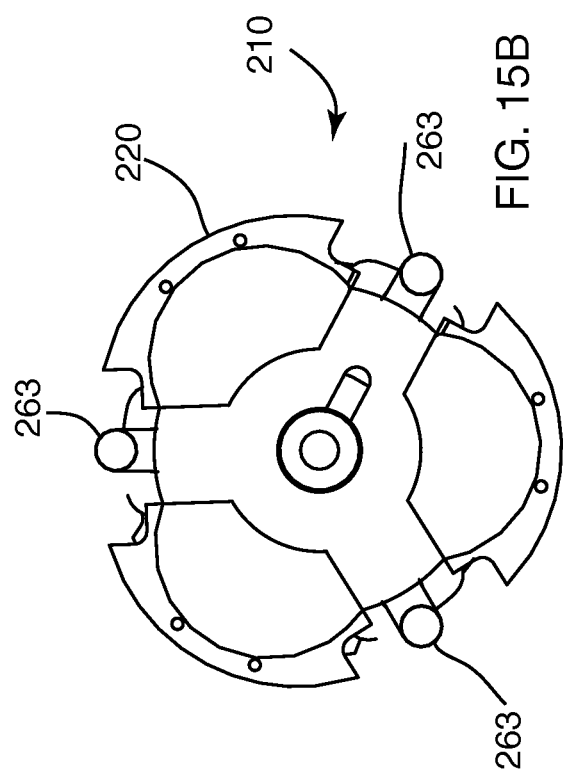
FIG. 15A
FIG. 15B

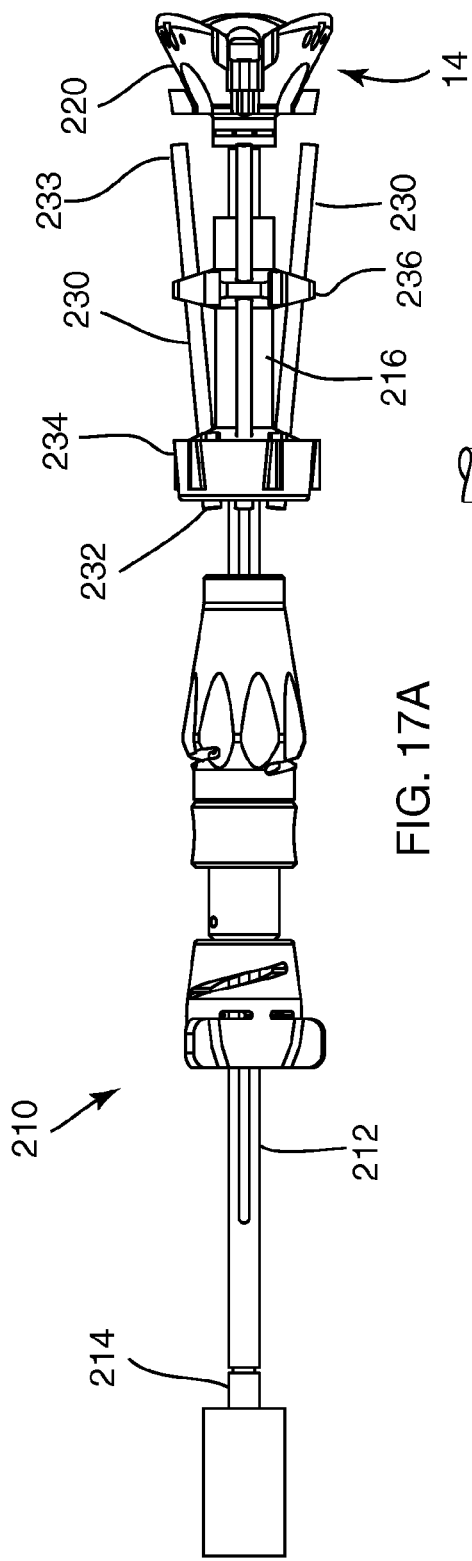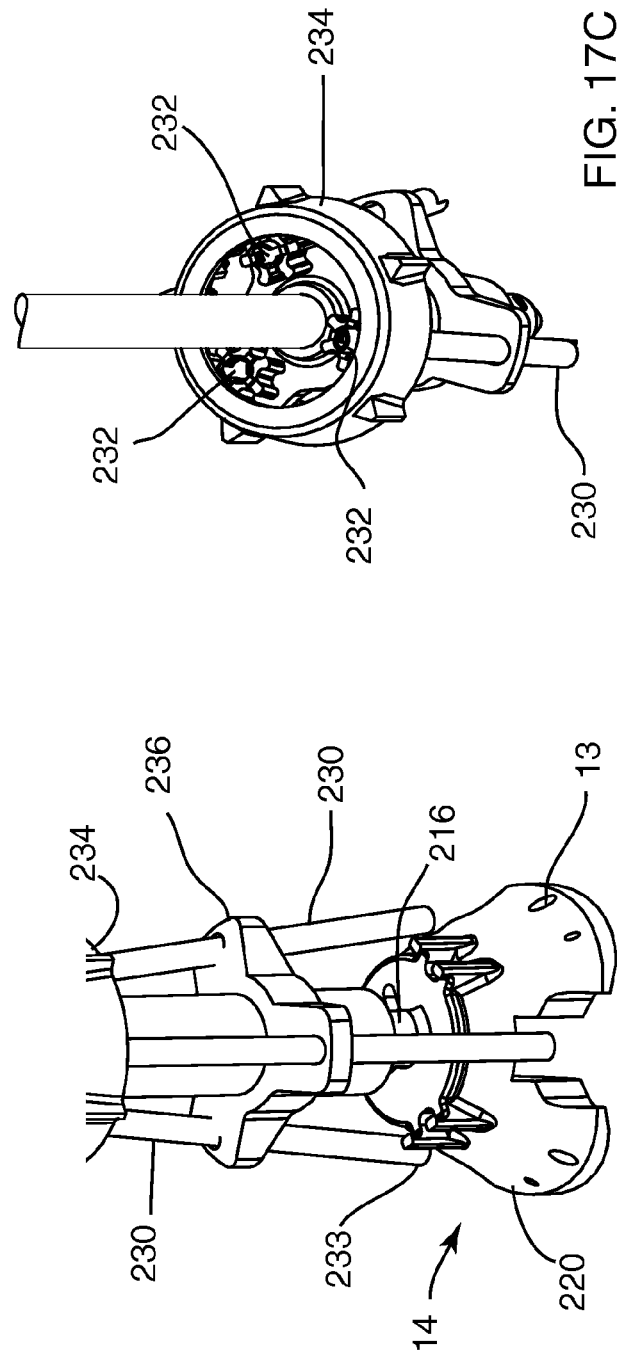

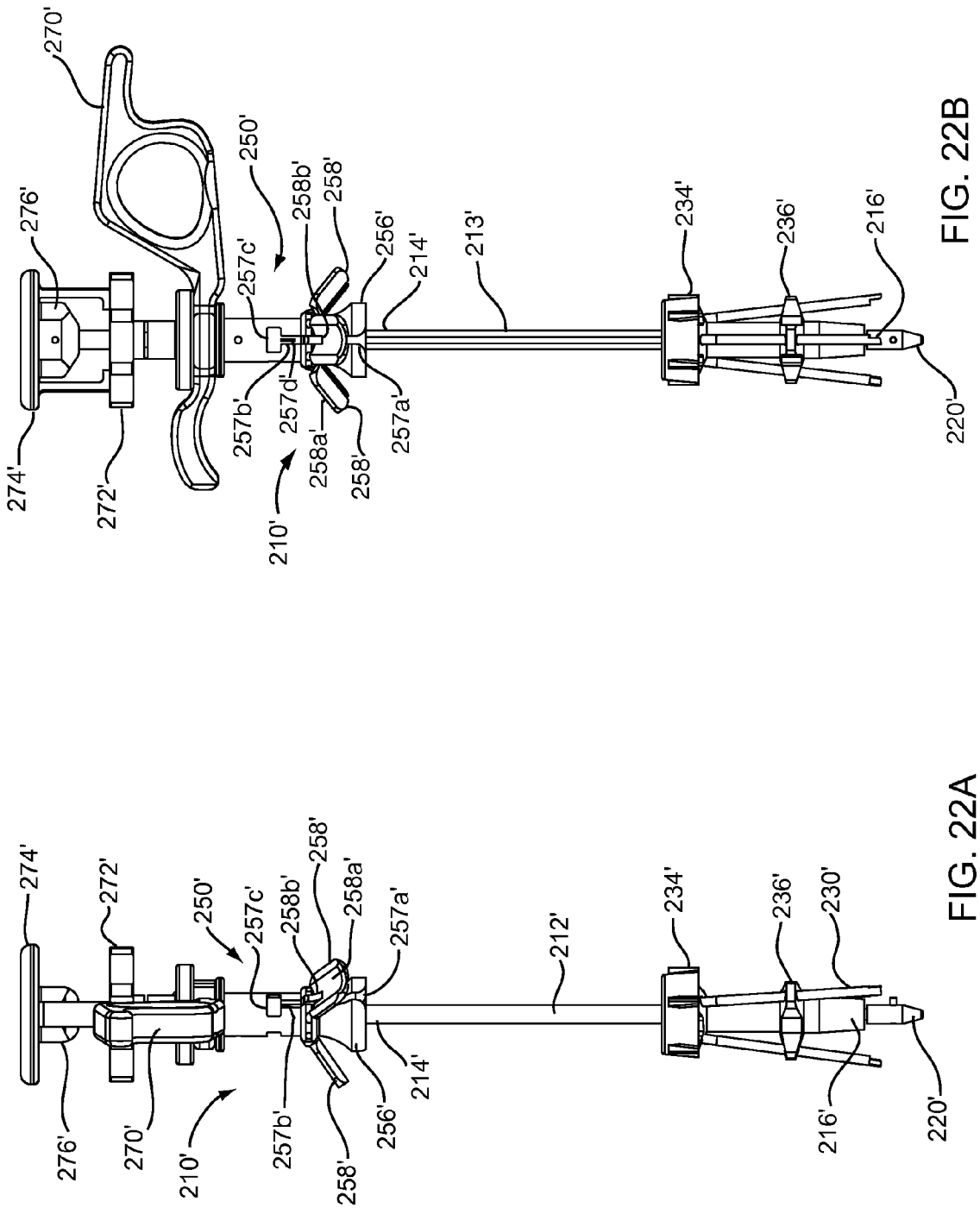

MULTIPLE COMPONENT PROSTHETIC HEART VALVE ASSEMBLIES AND METHODS FOR DELIVERING THEM

RELATED APPLICATION DATA

This application claims benefit of co-pending provisional application Ser. No. 60/746,038, filed Apr. 29, 2006, and 60/914,742, filed Apr. 29, 2007, the entire disclosures of which are expressly incorporated by reference herein.

FIELD OF THE INVENTION

The present invention relates generally to heart valves that may be implanted within a patient, and, more particularly, to multiple component heart valve assemblies that may be assembled together, and to apparatus and methods for using them.

BACKGROUND

Prosthetic heart valves can replace defective human valves in patients. For example, one piece valves have been suggested that include sewing rings or suture cuffs that are attached to and extend around the outer circumference of a prosthetic valve. In addition, multiple component valves have also been suggested that include a sewing ring that is separate from a valve component. The sewing rings of either type of prosthetic valve can be tedious and time consuming to secure within a target site, i.e., within an annulus of a heart where a natural heart valve has been removed.

For example, to implant a sewing ring within an annulus of a heart, between twelve and twenty sutures may be secured initially to tissue surrounding the annulus. The sewing ring and/or the entire prosthetic valve may then be advanced or "parachuted" down the sutures into the annulus. Knots may then be tied with the sutures to secure the sewing ring within the annulus, whereupon the sutures may be cut. Consequently, this procedure can be very complicated, requiring management and manipulation of many sutures. The complexity of the procedure also provides a greater opportunity for mistakes and requires a patient to be on cardiopulmonary bypass for a lengthy period of time.

Because the annulus of the heart may not match the circular cross-section of the sewing ring and/or prosthetic valve, the prosthetic valve may not fit optimally within the annulus. As a result, natural blood hemodynamics through and around the valve may be impaired, resulting in clotting, possible emboli production, and eventual calcification of the valve structure.

To address this concern, flexible sewing rings have been suggested for use with multiple component valves. The sewing ring may be implanted within the annulus, e.g., using the procedure described above, i.e., parachuted down an arrangement of sutures. The sewing ring may conform at least partially to the anatomy of the annulus. Alternatively, instead of using sutures, it has also been suggested to drive staples through the sewing ring into the surrounding tissue to secure the sewing ring.

When a mechanical or prosthetic valve is then attached to the sewing ring, however, the valve and sewing ring may not mate together effectively, e.g., if the shape of the sewing ring has been distorted to conform to the annulus, which may also impair natural blood hemodynamics, create leaks, and/or otherwise impair performance of the prosthetic valve.

In addition, less invasive or minimally invasive procedures are often desirable, because they may reduce stress on the patient's body and/or accelerate recovery after a procedure. Such procedures may involve creating smaller access sites and/or even using ports to access a procedure site. During valve replacement, in order to introduce a prosthetic heart valve and/or sewing ring into a patient's heart, the heart must be accessed, e.g., by sternotomy or thoracotomy. The resulting opening must be sufficiently large to permit passage of the prosthetic heart valve and still allow the physician to access and/or observe the site of implantation. Thus, conventional procedures for implanting prosthetic heart valves may not be compatible with less invasive or minimally invasive procedures.

SUMMARY OF THE INVENTION

The present invention is directed to prosthetic heart valves that may be implanted within a patient, and, more particularly, to multiple component heart valve assemblies that may be assembled together, and to tools, apparatus, systems, and methods for making and implanting them.

In accordance with one embodiment, a prosthesis is provided for receiving a valve prosthesis to replace a natural or prosthetic heart valve within a biological annulus. The prosthesis may include an annular member implantable within the biological annulus for contacting tissue surrounding the biological annulus, a sewing cuff extending from the annular member, and a plurality of elongate guide rails or other leaders extending from one of the annular member and the sewing cuff for guiding a valve prosthesis towards the prosthesis. Optionally, the annular member may be resiliently compressible, expandable, and/or otherwise biased, and/or may include a collar extending upwardly therefrom, a skirt, one or more guide shields, and/or other components.

In accordance with another embodiment, a prosthesis is provided for receiving a valve prosthesis to replace a natural or prosthetic heart valve within a biological annulus. The prosthesis may include an annular member that is compressible radially inwardly from a relaxed or expanded condition to a contracted condition to facilitate delivery into a biological annulus. When the annular member is released from the contracted condition, the annular member may resiliently expand towards the expanded condition, e.g., to dilate tissue surrounding the biological annulus. Optionally, the prosthesis may include a sewing cuff extending from the annular member, a collar extending upwardly therefrom, a skirt, a plurality of elongate guide rails or other leaders extending from the prosthesis for guiding a valve prosthesis member towards the prosthesis, and/or other components.

In accordance with yet another embodiment, a prosthesis is provided for receiving a valve prosthesis to replace a natural or prosthetic heart valve within a biological annulus. The prosthesis may include an annular member, and a plurality of guide rails or other leaders extending from the annular member. Each of the leaders may include a proximal end, a distal end secured to the annular member, and one or more ratchets, clasps, locking tabs, or other retention elements or connectors, e.g., configured to allow a valve member to be directed distally but not proximally over the connectors. In an exemplary embodiment, each of the connectors may include a tapered proximal surface and a blunt distal surface. The connectors may be spaced a predetermined distance from the annular member to secure the valve member against or immediately adjacent the annular member. Optionally, the annular member may be compressible radially inwardly from a relaxed or expanded condition to a contracted condition to facilitate delivery into a biological annulus, resiliently expandable towards the expanded condition, and/or otherwise biased.

In accordance with still another embodiment, a heart valve assembly is provided that includes a first annular prosthesis implantable within a biological annulus, a second valve prosthesis, and a plurality of elongate guide rails or other leaders extending from the first prosthesis for guiding the second prosthesis into engagement with the first prosthesis. In exemplary embodiments, the second prosthesis may be a mechanical valve or a bioprosthetic valve, e.g., including multiple tissue leaflets carried by a frame.

Optionally, the second prosthesis may include a plurality of receptacles or other features for receiving respective leaders. For example, the features may be ports or other receivers fixed to a frame or wall of the second prosthesis, a plurality of tubular members that may be removable from a frame, fabric covering, or other portion of the second prosthesis, and the like.

In one embodiment, one or more connectors may be provided on at least one of the first and second prostheses for securing the second prosthesis to the first prosthesis. For example, the one or more connectors may include one or more cooperating clips, detents, and the like that self-engage one another when the second prosthesis is directed towards the first prosthesis. In addition, or alternatively, the leaders may include one or more ratchets, clasps, locking tabs, or other retention elements or connectors for securing the second prosthesis against or immediately adjacent the first prosthesis.

In addition or alternatively, the first prosthesis may include an annular member, a sewing cuff extending radially from the annular member, and/or a skirt to enhance sealing between the first prosthesis and surrounding tissue. In one embodiment, the first prosthesis may also include a collar extending upwardly from the annular member for receiving the valve member. The sewing cuff and/or collar may be formed from resiliently flexible material, e.g., silicone or polyester film, covered with a fabric covering.

In accordance with yet another embodiment, a prosthetic heart valve system is provided that includes a first annular prosthesis, a second valve prosthesis, and one or more delivery tools for introducing the first and/or second prostheses. The first prosthesis may include an annular member implantable within a biological annulus for contacting tissue surrounding the biological annulus, a sewing cuff extending radially outwardly from the annular member, and a plurality of elongate guide rails or other leaders extending from one of the annular member and the sewing cuff for guiding the valve prosthesis towards the sewing cuff.

The one or more delivery tools may include an elongate member including a proximal end, a distal end sized for introduction into a biological annulus, and an actuator for directing the first prosthesis between an expanded or relaxed condition and a contracted condition that facilitates introduction into a biological annulus. In one embodiment, the tool may include a groove or lumen extending between the proximal and distal ends thereof for receiving portions of the leaders therethrough. The actuator may include a handle at the proximal end and one or more mechanisms for locking, tightening, and/or releasing the leaders received in the groove or lumen, e.g., to facilitate tightening and/or loosening the leaders. Thus, the first prosthesis may be releasably engaged with the distal end of the delivery tool when the leaders are secured to the delivery tool. For example, the first prosthesis may be compressible from an expanded or relaxed condition to a contracted condition when the leaders are tensioned, thereby drawing portions of the first prosthesis inwardly towards the distal end of the delivery tool.

In another embodiment, the tool may include a central hub or support and a plurality of movable arms for capturing the first prosthesis between the support and arms. The actuator may direct the arms inwardly and outwardly for directing the first prosthesis to the contracted condition and releasing the first prosthesis from the tool. In an exemplary embodiment, in the contracted condition, the first prosthesis may assume a clover or other multiple lobular shape, while, in the expanded condition, the first prosthesis may have a substantially circular shape. The first prosthesis may be resiliently compressible such that, when the first prosthesis is released, the first prosthesis may resiliently expand towards the expanded condition.

In accordance with still another embodiment, a prosthetic heart valve system is provided that includes a first annular prosthesis and a delivery tool. The first prosthesis may be resiliently compressible from a relaxed or expanded condition to a contracted condition. The delivery tool may include one or more constraints for maintaining the first prosthesis in the contracted condition. For example, the delivery tool may include a plurality of movable arms surrounding a central hub or set of supports, the arms being movable towards and away from the hub for capturing and/or compressing the first prosthesis between the arms and the hub. The first prosthesis may be resiliently compressible such that, when released from the one or more constraints, the first prosthesis may resiliently expand towards the expanded condition.

In accordance with yet another embodiment, a method is provided for implanting a prosthetic heart valve assembly to replace a natural or prosthetic heart valve within a biological annulus below a sinus cavity. A first annular prosthesis may be inserted into the biological annulus while in a contracted condition. In one embodiment, the first prosthesis may include a plurality of guide rails or other leaders extending from the prosthesis. At least a first portion of the first prosthesis may be deployed in the annulus so that the first prosthesis expands to an enlarged state therein, e.g., to at least partially dilate tissue surrounding the biological annulus. In addition or alternatively, the first prosthesis may include a flexible sewing cuff and/or skirt extending around the first prosthesis, which may be disposed supra-annularly and/or sub-annularly when the first portion is deployed in the biological annulus. One or more connectors, e.g., sutures, clips, and the like, may be directed through the first prosthesis, e.g., through the sewing cuff, and adjacent tissue, to secure the first prosthesis relative to the annulus.

A second valve prosthesis, e.g., a mechanical or bioprosthetic valve, may be directed into the annulus adjacent the first prosthesis. For example, the valve prosthesis may be advanced along guide rails or other leaders extending from the first prosthesis until the second prosthesis engages or otherwise contacts the implanted first prosthesis. In one embodiment, the valve prosthesis may be secured to the first prosthesis using one or more connectors, e.g., one or more sutures, clips detents, and/or other cooperating connectors, e.g., on the first prosthesis and a frame of the valve prosthesis. In addition or alternatively, the second prosthesis may be secured to the first prosthesis by ratcheting, locking, or other retention elements or connectors on the leaders.

In accordance with yet another embodiment, a method is provided for implanting a prosthetic heart valve assembly to replace a natural or prosthetic heart valve within a biological annulus below a sinus cavity. A gasket member and delivery tool may be provided with a plurality of elongate guide rails or other leaders extending from the gasket member into a distal end of the delivery tool. The leaders may be secured relative to the delivery tool, e.g., by a locking mechanism. A tightening mechanism on the delivery tool may be actuated to tension the leaders to compress the gasket member to a contracted condition. Alternatively, the delivery tool and gasket member may be initially provided with the leaders already tensioned.

The distal end of the delivery tool may be introduced into the sinus cavity, thereby carrying the gasket member in the contracted state at least partially into the biological annulus. The gasket member may be at least partially released from the delivery tool, e.g., to at least partially dilate tissue surrounding the biological annulus. For example, the locking mechanism on the delivery tool may be released, unlocked, or otherwise actuated to release the gasket member, allowing the gasket member to expand resiliently towards an enlarged condition. The gasket member may be attached to the biological annulus, e.g., using one or more fasteners, such as sutures, clips, and the like.

A valve member may then be introduced into the sinus cavity and secured to the first prosthesis. Optionally, the valve member may be carried by the same delivery tool used to introduce the gasket member or by a separate tool. The valve member may be secured to the gasket member by one or more connectors, e.g., sutures, clips, detents, ratcheting or other retention elements, and the like. In one embodiment, the valve member may be introduced into the sinus cavity along the leaders and/or may be secured to the gasket member by one or more connectors on the leaders.

In accordance with still another embodiment, a valve holder device may be provided for delivering a valve prosthesis into a biological annulus for connection to an annular prosthesis previously introduced into the biological annulus and including one or more guide rails or other leaders extending therefrom. For example, the valve holder device may include one or more elements, e.g., a head, for releasably carrying the valve prosthesis on a distal end of the valve holder device. In addition, the valve holder device may include one or more channels or other receivers for receiving respective leaders, the receivers slidably receiving the leaders while the valve holder device and valve prosthesis are directed towards the annular prosthesis. Optionally, the valve holder device may include one or actuators that may be manipulated to sever the leaders after the valve prosthesis is secured relative to the annular prosthesis.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIGS. 15A and 15B are side and end views, respectively, of a valve holder tool for delivering a valve prosthesis into a biological annulus.

FIG. 17A is a side view of the valve holder tool of FIGS. 15A-15D carrying a valve prosthesis.

FIG. 17B is a detail of a distal end of the valve holder tool of FIG. 17A, showing a plurality of sutures securing the valve prosthesis to the valve holder tool.

FIG. 17C is a detail of the distal end of the valve holder tool of FIGS. 17A and 17B, showing passages for receiving respective guide rails of a gasket member, such as that shown in FIGS. 8A and 8B.

FIGS. 22A and 22B are side views of another embodiment of a valve holder tool for delivering a valve prosthesis into a biological annulus.

DETAILED DESCRIPTION OF THE EXEMPLARY EMBODIMENTS

Figure 1:
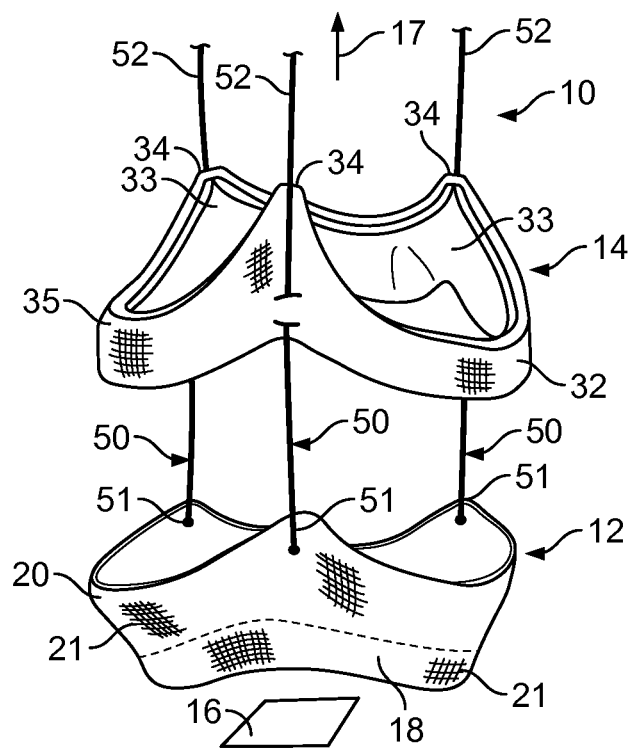
FIG. 1 is a perspective view of a two piece heart valve assembly including a gasket member having elongate leaders extending therefrom and a valve member.
Figure 2:
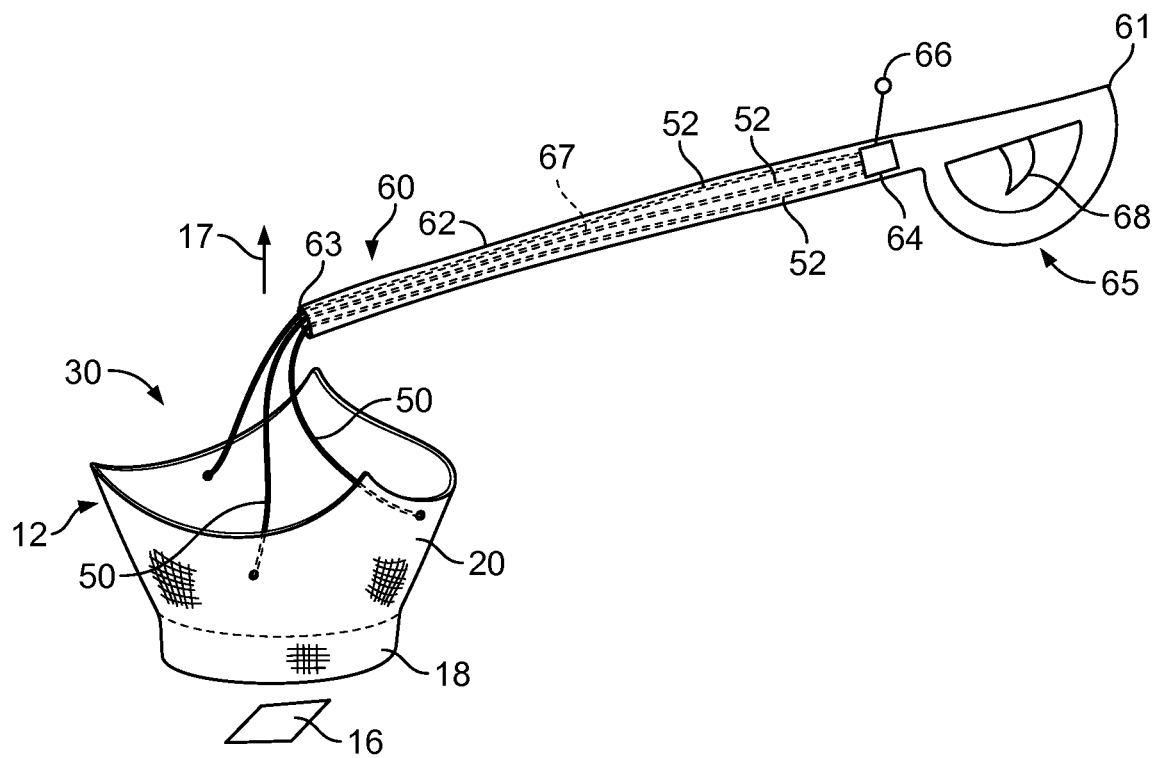
FIG. 2 is a perspective view of an apparatus for delivering the gasket member of FIG. 1 into a biological annulus that includes a delivery tool for receiving the elongate leaders from the gasket member.

Turning to the drawings, FIGS. 1 and 2 show an exemplary embodiment of a heart valve assembly 10 that generally includes a gasket member 12 and a valve member 14. The gasket member 12 is an annular shaped body generally defining a plane 16 and a central longitudinal axis 17 extending substantially perpendicular to the plane 16. As shown, the gasket member 12 includes an annular ring 18, a sewing cuff 20, and a plurality of elongate leaders, guide rails, or other elements 50 extending from the sewing cuff 20 or other portion of the gasket member 12, as described further below. Optionally, the gasket member 12 may also include a flexible skirt and/or baleen elements (not shown), e.g., surrounding the annular ring 18, a collar, and/or a plurality of guide shields (also not shown), similar to other embodiments described herein. A fabric covering 21 may be provided on one or more components of the gasket member 12, e.g., over the annular ring 18 and over a core of the sewing cuff 20, as described further below.

In one embodiment, the annular ring 18 may have a generally circular shape. Alternatively, the annular ring 18 may have a multi-lobular shape about the circumference, e.g., including three lobes separated by scallops or cusps (not shown) depending upon the anatomy within which the annular ring 18 is to be introduced. The annular ring 18 may be formed from an elastic or superelastic material, for example, metal, such as Nitinol, stainless steel, and the like, a polymer, or a composite material. Such material may facilitate compression and/or expansion of the annular ring 18, as described further below.

In an exemplary embodiment, the annular ring 18 may be cut from a flat sheet of base material having a desired thickness for the annular ring 18, for example, by laser cutting, mechanical cutting, and the like. Thus, the annular ring 18 may be initially formed as a long band of material, having a width corresponding to the desired width of the annular ring 18 and a length corresponding to the desired circumference of the annular ring 18. The band may be wrapped around a mandrel or otherwise restrained in a generally cylindrical shape with the ends adjacent to one another, and the band may be heat treated or otherwise processed to program the generally cylindrical shape into the material to create the annular ring 18. The generally cylindrical shape may include the ends overlapping one another, spaced apart from one another to provide an open "C" shape, or attached to one another. In another exemplary embodiment, the annular ring 18 may be manufactured from a solid rod of material, e.g. Nitinol, stainless steel, a polymer, or composite material, e.g., by machining, electrical discharge machining ("EDM"), laser cutting, or other processes.

Optionally, the annular ring 18 may be heat treated to program a shape memory into the band material, e.g., when the material is in an austenitic state. For example, the programmed shape may be an enlarged or relaxed condition, e.g., having a substantially circular shape. The composition of the material may be such that the annular ring 18 transforms to a substantially martensitic state substantially below body temperature, e.g., at or below ambient temperatures (e.g., 20° C. or less). Thus, in the martensitic state (before delivery), the annular ring 18 may be relatively soft such that the annular ring 18 may be plastically compressed or otherwise deformed, e.g., into a contracted condition to facilitate delivery, as described below. A transition temperature of the material may be set such that the annular ring 18 transforms substantially back to an austenitic state close to or at about body temperature (e.g., at 37° C. or more). Thus, once the annular ring 18 is exposed within a patient's body, the annular ring 18 may automatically become biased towards the enlarged condition due the shape memory of the austenitic state.

Alternatively, the material may be programmed to assume an austenitic state at both ambient and body temperatures, but within the elastic or superelastic range of the material. Thus, the annular ring 18 may be elastically compressed into the contracted condition, but may resiliently expand towards the enlarged condition when released from any constraints maintaining the annular ring 18 in the contracted condition.

The annular ring 18 may be at least partially covered with fabric, e.g., for tissue ingrowth, by wrapping fabric around the annular ring 18, while accommodating expansion and contraction of the annular ring 18. For example, at least near the ends of the band forming the annular ring 18, the fabric may not be secured to the annular ring 18, allowing the ends to slide circumferentially relative to the fabric. Optionally, sutures and the like (not shown) may be used to secure the fabric to the annular ring 18 at locations removed from the ends, e.g., at an intermediate location about the circumference of the annular ring 18. Alternatively, the entire annular ring 18 may be free to slide within the fabric wrapped around the annular ring 18.

With continued reference to FIGS. 1 and 2, the sewing cuff 20 may be attached to or otherwise extend around the annular ring 18. The sewing cuff 20 may simply be one or more layers of fabric or other material covering at least a portion of the annular ring 18. For example, a layer of fabric 21 may cover all of the annular ring 18 (other than any connectors and/or bearing surfaces, if any) and/or may include a section of material extending radially outwardly from the annular ring 18 to at least partially define the sewing cuff 20.

Optionally, the sewing cuff 20 may include flexible core material (not shown) that may be attached to or otherwise extend around the annular ring 18. For example, the core may be secured around the annular ring 18 by an interference fit, bonding, fusing a portion of the core to the annular ring 18, e.g., along an upper edge thereof, and the like. The core may be substantially covered with fabric, similar to the annular ring 18.

In an exemplary embodiment, the core may include a lattice (not shown) extending around a circumference of the core, e.g., including at least two spaced apart circumferential elements and a plurality of ribs or transverse elements extending between the circumferential elements, thereby defining openings through the lattice. The openings may be completely open, i.e., free from any material. Alternatively, the openings may be recesses including a relatively thin wall of core material, i.e., that is substantially thinner than the circumferential elements and/or ribs. In other embodiments, the core may include a base or web and a plurality of fins or ribs extending from the web to provide a flexible structure, e.g., which may facilitate sealing between the sewing cuff 20 and valve member 14.

Exemplary materials for the core include silicone or other elastomeric materials, foam, fabric, felt, polymers, and the like. In addition or alternatively, the core may include swellable material, e.g., foam or sponge materials that may expand when exposed to fluid, such as blood. The materials may be molded or otherwise formed into the core, e.g., using known molding, extrusion, cutting, or other manufacturing procedures. For example, the core may be injection molded or otherwise formed in its annular shape.

Alternatively, the core may be molded or otherwise formed as a flat sheet, and rolled into the annular shape. In this alternative, the ends of the sheet may be attached to one another, e.g., using sutures, adhesives, ultrasonic welding, and the like. Optionally, to provide a tapered shape, one or more wedges (not shown) may be cut out of the band to provide a desired tapered but annular shape. In another option, portions of the core may be disconnected from other portions, e.g., to prevent puckering. For example, if the core is formed from a rolled sheet (not shown), ends of the sheet (also not shown) may remain loose to allow the ends to move relative to one another.

In a relaxed state (free from external forces), the sewing cuff 20 may adopt an undulating annular shape or a generally planar annular shape. The sewing cuff 20 may also be tapered, as shown in FIGS. 1 and 2, e.g., having a larger diameter or circumference about an upper edge than about an edge adjacent the annular ring 18. The tapered shape of the sewing cuff 20 may define an angle relative to the longitudinal axis 17, e.g., between about twenty and forty five degrees (20-45°).

The material of the core may be substantially flexible, e.g., manufactured in a desired annular shape, yet easily deformed, e.g., deflected, stretched, and/or compressed. The core may be sufficiently flexible to be "floppy," i.e., such that the core conforms easily to the particular anatomy and/or implantation arrangements encountered during implantation. Thus, when the sewing cuff 20 is placed above or within a biological annulus within a patient's heart, the core may conform to the surrounding anatomy and/or may deform when the valve member 14 is secured to the gasket member 12, e.g. to enhance sealing between the valve member 14 and the gasket member 12, as described further below. Additional information on flexible cores or other constructions of the sewing cuff 20 may be found in U.S. Publication No. US 2006/0195184, filed as Ser. No. 11/069,081, the entire disclosure of which is expressly incorporate by reference herein.

Figure 4:
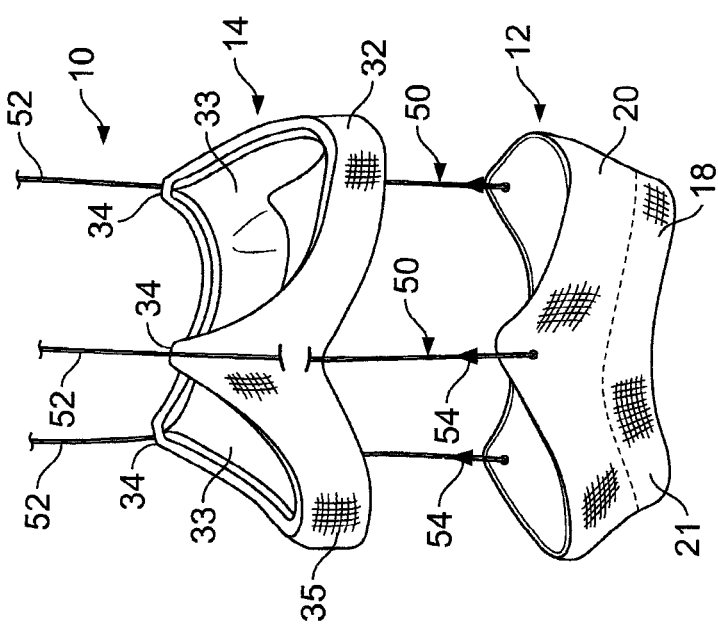
FIG. 4 is a perspective view of another embodiment of a heart valve assembly, including a gasket member having elongate leaders extending therefrom that include retention elements, and a valve member.

With continued reference to FIGS. 1 and 2, the leaders 50 may include elongate rails, fibers, or filaments including a first or distal end 51 attached or otherwise secured to the gasket member 12 and a second or proximal end 52. Optionally, the leaders 50 may include one or more markers or other elements (not shown) spaced apart along at least a portion of their lengths, e.g., immediately adjacent the first end 51. In addition or alternatively, as shown in FIG. 4, the leaders 50 may include one or more unidirectional or bidirectional retention elements 54, e.g., locking beads, tabs, ratchets, detents, and the like. As explained further elsewhere herein, these leaders may also provide connectors for attaching and/or securing the valve member 14 to or adjacent the gasket member 12.

The leaders 50 may be threads, filaments, wires, rails, or other tethers that extend from the gasket member 12. For example, the leaders 50 may be monofilaments or multifilament structures, e.g., braided, spun, or otherwise formed into a unitary member. The leaders 50 may be formed from wire or suture materials, e.g., plastic, such as polyethylene, metal, such as stainless steel, cat gut, or composite materials, using known methods. The leaders 50 may be stiff or flexible, and/or may be resiliently bendable or plastically pliable. The retention elements 54 may be integrally formed on the leaders 50, e.g., at the time the leaders 50 are formed, or may be separate elements (made from the same or different materials than the leaders 50) that are bonded, fused, or otherwise attached to the leaders 50 at predetermined locations. Alternatively, the leaders 50 may be flat bands, e.g., formed from plastic or other material, and may have the retention elements 54 formed therein or attached thereto, as described elsewhere herein.

With continued reference to FIG. 4, the retention elements 54 may include tapered proximal edges 54a and substantially blunt distal edges 54b. The proximal edges 54a may provide a substantially smooth transition allowing the valve member 14 to be passed distally over the retention elements 54. The distal edges 54b may provide locks that prevent the valve member 14 from being passed proximally back over the retention elements 54, similar to a ratchet or detent, as described further below. In alternative embodiments, the retention elements on the leaders 50 may include knots (not shown) tied onto the leaders 50 and/or beads (also not shown) formed on the leaders 50 at predetermined locations. Although only one retention element 54 is shown on each leader 50, optionally, multiple retention elements 54 may be provided spaced apart from one another along each leader 50.

Each leader 50 may be attached to, pre-threaded through, or otherwise placed on the gasket member 12, e.g., at spaced apart intervals from one another. For example, leaders 50 may be provided on the gasket member 12 that are aligned with the commissures (not shown) on the valve member 14 and/or a biological annulus into which the gasket member 12 is to be implanted. Thus, for example, for a prosthesis for an aortic valve having three commissures, three leaders 50 may be provided, as shown.

Each leader 50 may be attached to the gasket member 12 by directing the first end 51 through a predetermined location in the gasket member 12 and melting or otherwise expanding the first end 51 (e.g., similar to a rivet or nail head) to prevent subsequent removal. Alternatively, the first end 51 may be looped back around the leader 50 and bonded, fused, tied, or otherwise secured to the leader 50. In another alternative, the first end 51 may be pulled and secured or disposed adjacent the second end 52 (not shown), e.g., similar to a double-arm suture. The leaders 50 may be attached to the fabric of the sewing cuff 20 immediately adjacent the annular ring 18, or to other portions of the gasket member 12, e.g., to the annular ring 18, the core of the sewing cuff (not shown), or other portions of the fabric covering of gasket member 12.

Optionally, the gasket member 12 may include one or more additional components. For example, the gasket member 12 may include a collar or stand-off 58 that extends upwardly from the sewing cuff 20 for receiving the valve member 14, such as that shown in FIG. 8C. In addition or alternatively, a skirt or a plurality of baleen elements (not shown) may be provided around or adjacent the annular ring 18, e.g., that may bias a portion of the fabric covering outwardly (also not shown). Additional information on materials, construction, and/or components of the gasket member 112 may be found in U.S. Publication Nos. US 2004/0122516, filed as Ser. No. 10/327,821, US 2005/0165479, filed as Ser. No. 10/765,725, US 2006/0195184, filed as Ser. No. 11/069,081, and US 2007/0016285, filed as Ser. No. 11/420,720, and in co-pending application Ser. No. 11/567,735, filed Dec. 6, 2006. The entire disclosures of these references are expressly incorporated by reference herein.

Figure 3A:
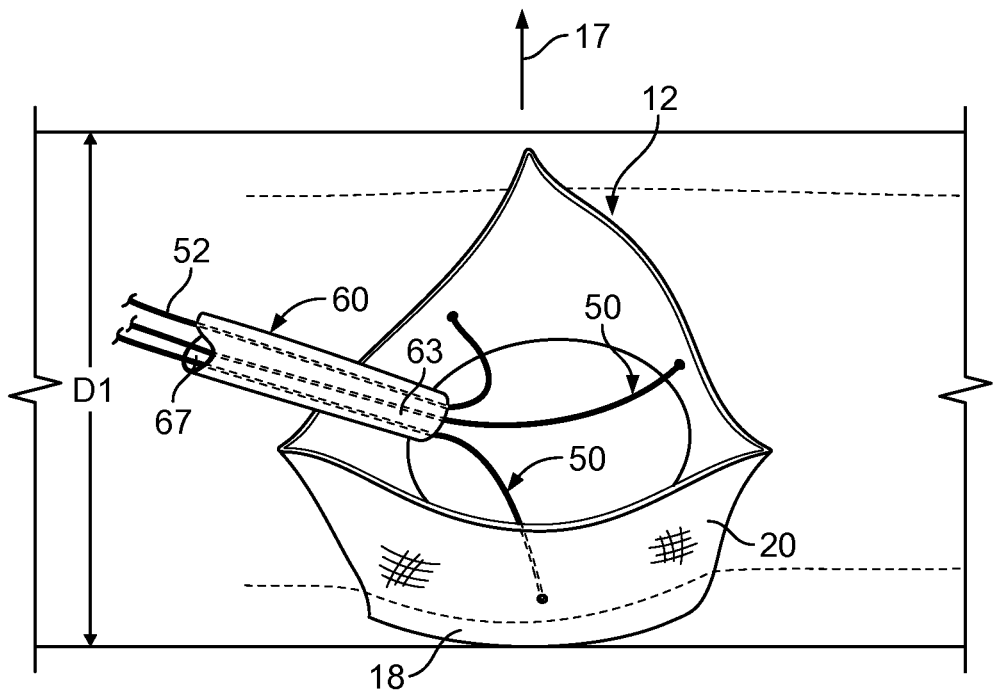
FIG. 3A is a perspective view of the apparatus of FIG. 2, showing the gasket member in a relaxed condition, when the leaders are free from external forces.
Figure 3B:
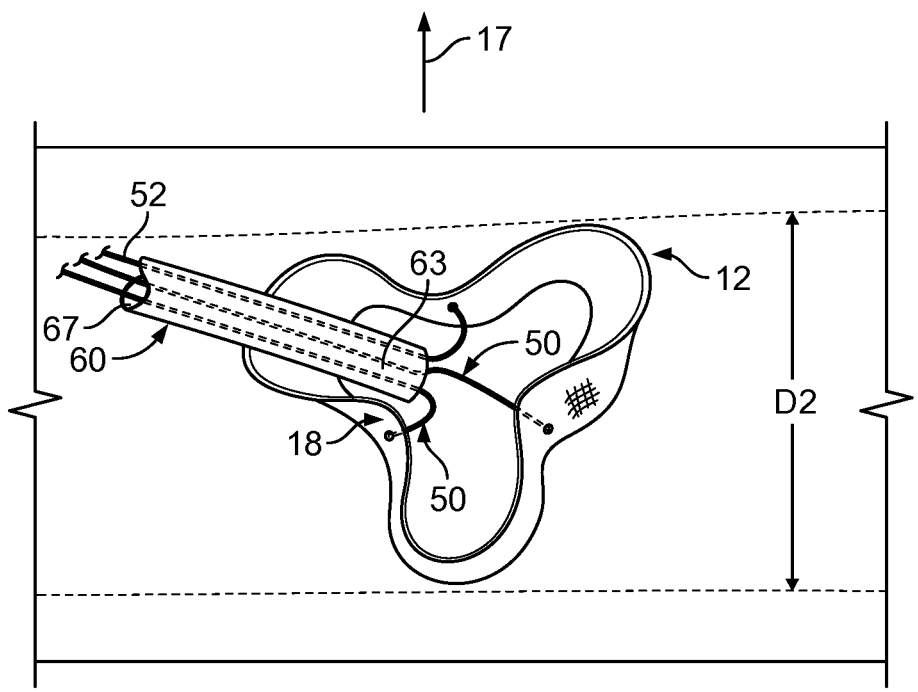
FIG. 3B is a perspective view of the apparatus of FIGS. 2 and 3A, showing the gasket member in a contracted condition, when tension is applied to pull the leaders further into the delivery tool.

Turning to FIGS. 3A and 3B, the gasket member 12 may be expandable and/or compressible such that the cross-section of the gasket member 12 may be adjusted, e.g., to accommodate introduction into a patient's body during a procedure, as described further elsewhere herein. In one embodiment, the annular ring 18 may be biased to a relaxed or expanded condition, e.g., defining a predetermined diameter "D1" (as shown in FIG. 3A). At least a portion of the annular ring 18 may be contracted radially inwardly to define a smaller diameter or cross-section "D2" (as shown in FIG. 3B), e.g., to facilitate delivery into a biological annulus. As described above, the sewing cuff 20 may be substantially flexible such that the sewing cuff 20 is also compressed radially inwardly as the annular ring 18 is compressed. Thus, the gasket member may be compressible, yet may be resiliently expandable to dilate tissue surrounding the annulus and/or to facilitate securing the gasket member 12 within a biological annulus.

To contract the gasket member 12, tension may be applied to the leaders 50 (e.g., using delivery tool 60, described further below), e.g., to draw one or more portions of the gasket member 12 inwardly towards the central axis 17. For example, inward and/or proximal tension may be applied to the leaders 50, e.g., by pulling the leaders 50 at least partially into the delivery tool 60, as described further below, which may pull the ends of the leaders 50 inwardly towards the central axis 17. As the leaders 50 are tensioned, the annular ring 18 may contract inwardly to assume a multiple lobular shape, e.g., as shown in FIG. 3B, such that the gasket member 12 assumes the contracted condition.

The annular ring 18 may deform elastically towards the contracted condition. Alternatively, as described elsewhere herein, the annular ring 18 may be cooled to a martensitic state, e.g., by immersing the gasket member 12 in ice, ice water, or other fluid maintained at a temperature below the final martensitic temperature of the annular ring 18. In this alternative, the annular ring 18 may be plastically deformed while the annular ring 18 is in the relatively soft, martensitic state.

When tension of the leaders 50 is released, e.g. by releasing the leaders 50 at least partially from the delivery tool 60, the annular ring 18 may resiliently expand outwardly, e.g., to a shape having a generally circular cross-section, thereby returning the gasket member 12 towards the expanded condition, e.g., as shown in FIG. 3A. For example, if the annular ring 18 is deformed elastically to the contracted condition, the annular ring 18 may simply expand resiliently towards the expanded condition. Alternatively, if deformed in a martensitic state, the gasket member 12 may be heated such that the annular ring 18 resumes an austenitic state, e.g., when the annular ring 18 is exposed to ambient temperatures or body temperature. In this alternative, the annular ring 18 may "remember" the expanded condition and become biased to expand upon being released.

Turning to FIG. 2, an exemplary embodiment of an apparatus or system 30 is shown for delivering a prosthesis into a biological annulus that includes a gasket member 12 and a delivery tool 60. The gasket member 12 may be any of the embodiments described herein, e.g., including an annular ring 18, a sewing cuff 20, and a plurality of elongate leaders 50. The delivery tool 60 generally includes a shaft 62 having a proximal end 61, a distal end 63 sized and/or shaped for introduction into an opening in a patient's body, and a handle 65 on the proximal end 61. The delivery tool 60 may also include one or more lumens 67 (one shown in phantom) extending between the proximal and distal ends 61, 63, e.g., for receiving portions of the leaders 50 therein. Alternatively, the shaft 62 may include other configurations, e.g., a "U" shaped cross-section defining a channel for receiving the leaders 50 therein. Such a cross-section may facilitate loading the leaders onto the delivery tool 60.

The handle 65 may also include one or more actuators 66, 68, e.g., one or more locking, tightening, and/or loosing mechanisms for manipulating the leaders 50. For example, the delivery tool 60 may include a locking mechanism 64 for releasably securing the second ends of the leaders 50, e.g., one or more clamping structures, detents, and the like. In addition or alternatively, the actuators 66, 68 may allow the second ends of the leaders 50 to be directed proximally or distally, e.g., to apply or release tension, as described further below. As shown, the locking mechanism 64 includes a lever 66 that may be actuated to release the second ends of the leaders 50, and a latch 68 that may be actuated to increase and/or decrease tension applied to the leaders 50.

For example, the leaders 50 may be loaded into the distal end 63 of the delivery tool 60 and through the lumen 67 until the second ends are engaged or otherwise received by the locking mechanism 64. Optionally, the leaders 50 may be loaded by a user shortly before a procedure, e.g., allowing a gasket member 12 of a desired size "D1" to be selected and loaded onto the delivery tool 60. Alternatively, the leaders 50 may be preloaded into a delivery tool 60 during manufacturing, although this may require providing multiple delivery tools 60 before a procedure, each carrying a different size gasket member 12.

When it is desired to compress the gasket member 12, the latch 68 may be actuated to pull the leaders 50 proximally a predetermined distance within the delivery tool 60. This action may pull the gasket member 12 proximally against the distal end 63 of the delivery tool 60 and/or radially inwardly, as shown in FIG. 3B. The tension may be selected to compress the gasket member 12 to a predetermined size and/or shape. As shown in FIG. 3B, the gasket member 12 has been compressed into a three lobe clover-like shape having a cross-section "D2." The tension may be applied by a user shortly before introducing the gasket member 12 into a patient or the tension may be preloaded, e.g., during manufacturing.

When it is desired to deploy the gasket member 12, the lever 66 may be actuated, thereby releasing the leaders 50 from the delivery tool 60. Alternatively, the tension on the leaders 50 may be released by actuating the latch 68, e.g., in the opposite direction, from that used to apply the tension, without releasing the leaders 50 entirely from the delivery tool 60. In a further alternative, the lever 66 and latch 68 may be combined into a single actuator having multiple settings or positions, depending upon the action desired (e.g., tension, tension release, fully release).

It will be appreciated that other constraints and/or delivery tools may be provided to compress and/or maintain the gasket member 12 in a contracted condition. For example, a delivery tool (not shown) may be provided that includes a tubular body or other structure into which the entire gasket member 12 may be loaded, e.g., after compressing the gasket member 12 to the contracted condition. The delivery tool may include a plunger or other device (not shown) within the tubular body that may be used to deploy the gasket member 12 from the tubular body. In an exemplary embodiment, the gasket member 12 may be compressed by flattening the annular ring 18 along the plane 16 and then folding or rolling the resulting flattened annular ring 18. For example, after flattening the annular ring 18, the annular ring 18 may be rolled into a spiral, folded in half, e.g., into a "C" shape, such as that shown in FIG. 12, or otherwise compressed. When the gasket member 18 is deployed from the delivery tool, the annular ring 18 may resiliently return to its expanded condition, similar to the other embodiments described elsewhere herein. Additional information regarding apparatus and methods for using such as gasket member and/or heart valve assembly may be found in U.S. Publication No. 2007/0016288, filed as Ser. No. 11/457,437, the entire disclosure of which is expressly incorporated by reference herein.

Returning to FIGS. 1 and 2, the valve member 14 generally includes an annular shaped body or frame 32 and one or more valve elements 33. The valve member 14 may include a fabric covering 35, similar to the gasket member 12, e.g., covering the frame 32 and/or other components of the valve member 14. The frame 32 may have a noncircular, e.g., multiple lobular shape corresponding to a shape of the biological annulus within which the valve member 14 is to be implanted. For example, the valve member 14 may have a tri-lobular shape, including three lobes separated by cusps or scallops, e.g., corresponding to a sinus of Valsalva above an aortic valve site. In one embodiment, the valve member 14 may be a bioprosthetic valve member, e.g., an annular frame 32 carrying a plurality of tissue leaflets 33. The frame 32 may include a plurality of struts (also not shown for clarity) that may be attached to and/or otherwise carry the leaflets 33. For example, the struts may include a laminate structure, including two or more sheets of flexible material, similar to the valves disclosed in U.S. Pat. No. 6,371,983, and U.S. Publication No. US 2006/0276888, filed as Ser. No. 11/144,254, the entire disclosures of which are expressly incorporated by reference herein.

Alternatively, the valve member 14 may be a connecting device to which a valve (not shown) may be connected or that may otherwise receive a valve component, such as the connection adapter elements shown in U.S. Publication No. US as 2005/0043760, filed as Ser. No. 10/646,639, the entire disclosure of which is expressly incorporated by reference herein. In another alternative, the valve 14 may include a mechanical valve or other valve (not shown), such as those disclosed in US 2005/0165479 and US 2007/0016285725, incorporated by reference above.

Figure 6:
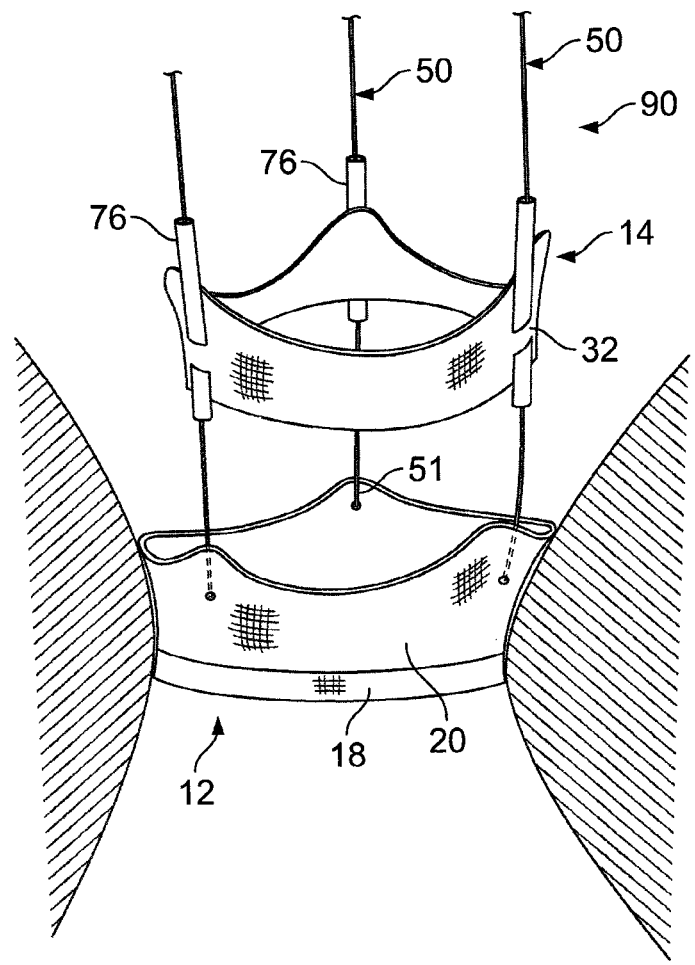
FIG. 6 is a cross-sectional view of a biological annulus showing an alternate embodiment of a valve member that may be provided for a heart valve assembly implanted within the biological annulus.
Figure 7:
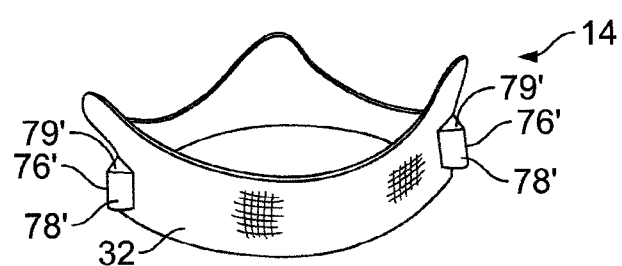
FIG. 7 is a perspective view of another alternate embodiment of a valve member.

Turning to FIGS. 6 and 7, optionally, the valve member 14 may include one or more introducers or receivers 76 through which leaders 50 may be received. For example, as shown in FIG. 6, a first embodiment of an introducer 76 is shown that includes a tubular member 76 received through a portion of the valve member 14. For example, the tubular members 76 may simply be removably inserted through predetermined regions of a fabric covering on the frame 32, e.g., such that the tubular members 76 extend substantially parallel to the longitudinal axis 17. As shown, the tubular members 76 are located at commissures 34 of the frame 32, although alternatively, the tubular members 76 may be located at other desired angular locations around the frame 32 corresponding to the locations of the leaders 50 on the gasket member 12 (not shown in FIG. 6; see, e.g., FIG. 1).

The tubular members 76 may be formed from a variety of materials, e.g., a section of hypotube, made from metal, such as stainless steel, plastic, or composite materials. The tubular members 76 may be preloaded onto the frame 32, e.g., during manufacturing, or loaded onto the frame 32 shortly before a procedure. As described further below, the tubular members 76 may be removed from the frame 32 at any time, e.g., immediately before or after securing the valve member 14 to the gasket member 12.

FIG. 7 shows another embodiment of introducers 76' that may be provided directly on the valve member 14. As shown, for example, the introducers 76' are formed from a piece of fabric or other material 78' attached to the fabric covering the valve member 14, thereby defining a pocket or passage 79' therethrough. The introducers 76' may be a rectangular section of material whose side edges are stitched, bonded, or otherwise attached to the fabric covering or other portion of the valve member 14, or a separate tubular structure. In yet another embodiment, the leaders 50 may be introduced through the fabric itself of valve member 14, e.g., using a needle or other tool (not shown) on the second ends of the leaders 50 to "pick up" one or more threads of the fabric. Additional information on introducers or receivers may be found in US 2005/0165479, incorporated by reference herein.

Figure 5A:
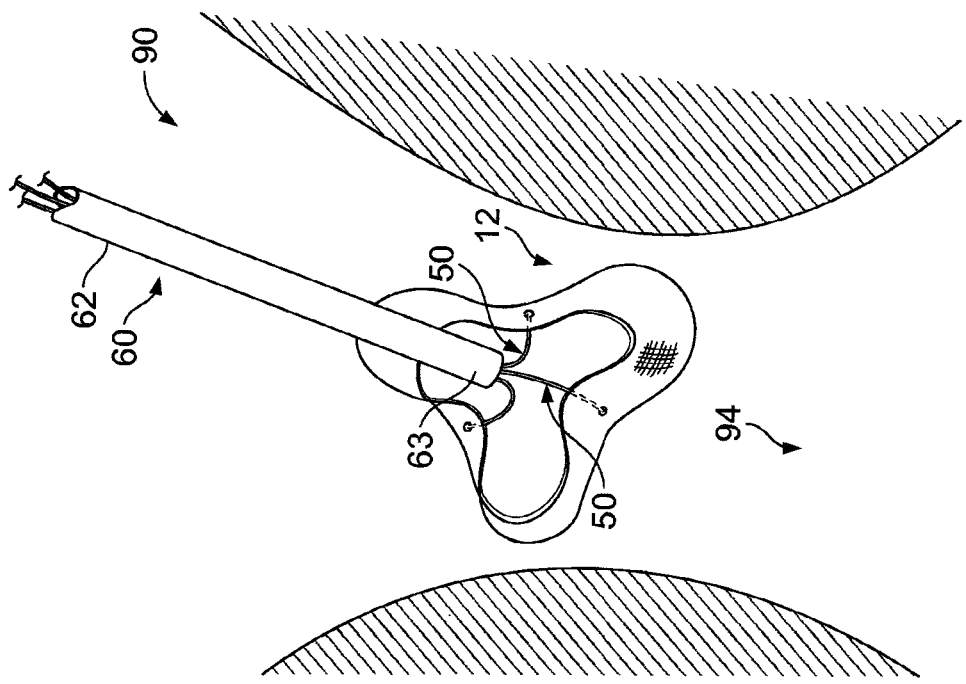
FIGS. 5A-5C are cross-sectional views of a biological annulus, showing a method for implanting the heart valve assembly of FIG. 4.
Figure 5C:
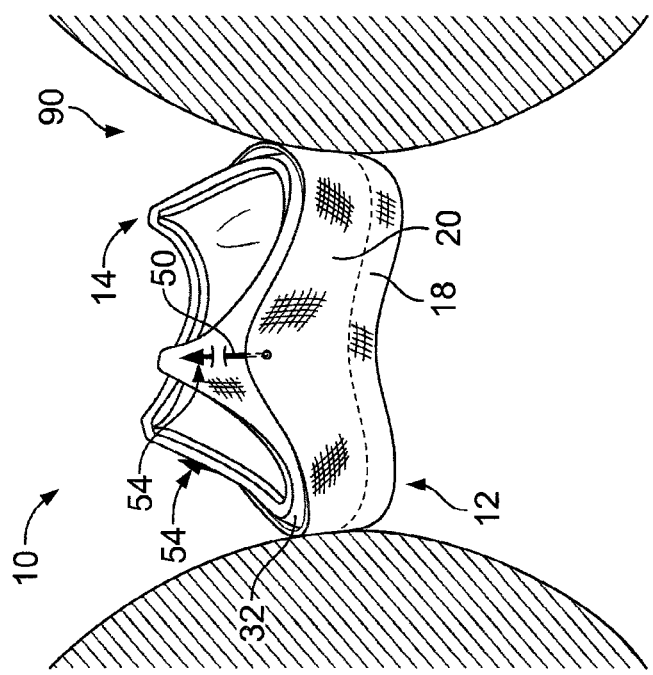
Figure 5B:
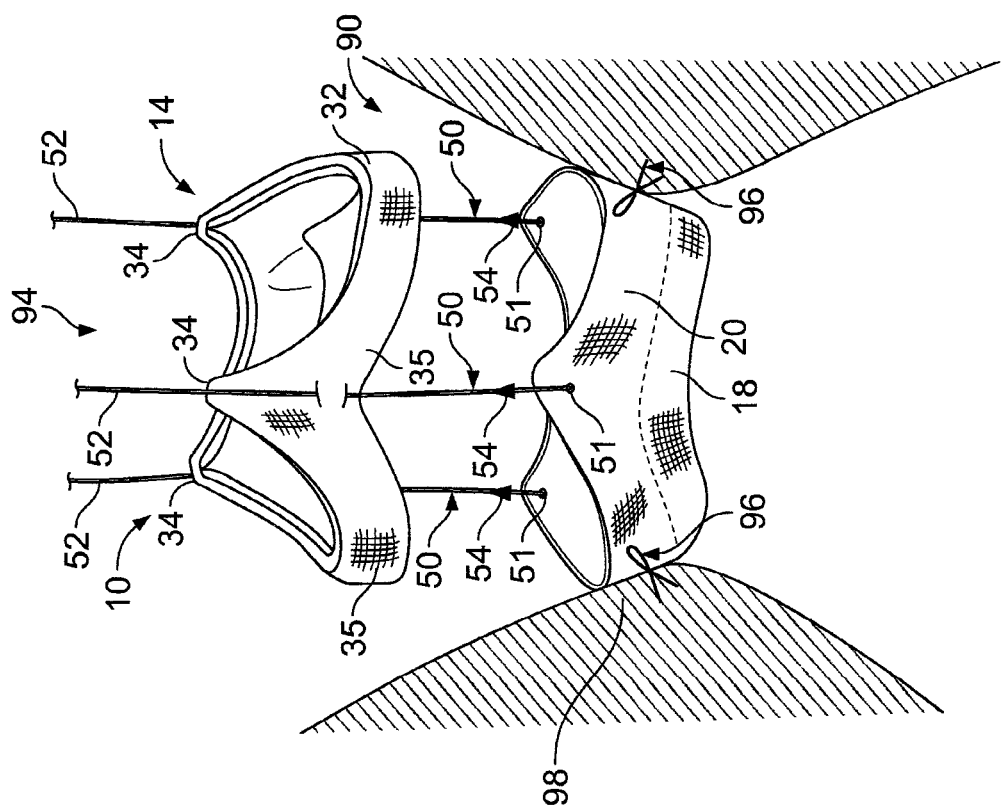

Turning to FIGS. 5A-5C, during use, the heart valve assembly 10 may be implanted within a patient's body, e.g., within or adjacent to a biological annulus 90. The biological annulus 90 may be the site for replacing an existing natural or previously implanted heart valve, such as a tricuspid, mitral, aortic, or pulmonary valve within a patient's heart (not shown).

Before implanting the heart valve assembly 10, the patient may be prepared for the procedure using known methods. For example, the patient may be placed on cardiopulmonary bypass (CPB), and the patient's heart may be exposed, e.g., by sternotomy, thoracotomy, or other open or minimally invasive procedure. An incision may be created in the blood vessel above the valve being replaced (not shown), e.g., the aorta for an aortic valve replacement, in order to access the annulus 90. The existing natural or prosthetic heart valve and/or leaflets (also not shown) may be removed from the annulus 90 using known methods.

A heart valve assembly 10, e.g., including a gasket member 12 and a valve member 14, may be selected based upon the anatomy encountered, e.g., having a plurality of lobes, matching the lobes of the biological annulus 90 and/or having a cross-sectional dimension corresponding to the interior cross-section of the biological annulus 90. Optionally, a gasket member 12 and/or valve member 14 may be selected having a size that is larger than the biological annulus 90. For example, the gasket member 12 may have a diameter in its relaxed condition that is slightly larger than the biological annulus 90, e.g., such that the gasket member 12 may at least partially dilate the biological annulus 90 upon implantation. In addition or alternatively, the valve member 14 may have a diameter or other cross-section that is substantially larger than the biological annulus 90, e.g., for supra-annular or intra-sinus implantation, which may accommodate the larger size.

With reference to FIG. 5A, initially the gasket member 12 may be restrained in the contracted condition, e.g., by the delivery tool 60. For example, as described above, the gasket member 12 may include leaders 50 and the delivery tool 60 may be provided with the leaders 50 preloaded into the delivery tool 60. The leaders 50 may be provided initially in a relaxed state, i.e., without subjecting the gasket member 12 to any tension or other stress, e.g., to prevent fatigue of components and/or materials of the gasket member 12. Immediately before use, the user (e.g., a physician, physician's assistant, nurse, or other medical professional) may actuate the latch 68 to apply tension to the leaders 50, e.g., to compress the gasket member 12 inwardly to the contracted condition shown in FIG. 5A. Optionally, before compressing the gasket member 12, the gasket member 12 may be placed in ice water or otherwise chilled, e.g., to "soften" or place the annular ring 18 in a martensitic state, as described elsewhere herein. In addition or alternatively, the predetermined tension may pull the gasket member 12 onto or around the distal end 63 of the delivery tool 60, thereby stabilizing and/or securing the gasket member 12 relative to the distal end 63, e.g., to facilitate introduction into the patient's body. Alternatively, the leaders 50 may be pre-tensioned by the delivery tool 60 before use, e.g., during manufacturing, as described above.

In an alternative embodiment, the user may load the leaders 50 into the deliver tool 60 immediately before the procedure, and then apply the desired tension to compress and/or stabilize the gasket member 14. This alternative may be particularly desirable when a single delivery tool 60 is used to deliver one of various sized gasket members available to the user. Thus, once the implantation site is exposed, the physician may measure the size of the biological annulus 90 and select an appropriate gasket member 12 (and/or valve member 14) based upon the specific anatomy encountered.

Once constrained in the contracted condition, the gasket member 12 may be introduced into the patient's body and advanced into the biological annulus 90, e.g., by directing the distal end 63 of the delivery tool 60 into the patient's body. The gasket member 12 may be advanced until the annular ring 18 extends at least partially into the biological annulus 90. In one embodiment, the annular ring 18 may extend through the biological annulus 90, i.e., with a lower edge of the annular ring 18 disposed within the sub-annular space below the biological annulus 90. Optionally, the gasket member 12 may include a flexible skirt (not shown) that may surround and/or extend from the annular ring 18 through the biological annulus 90. The skirt may be biased to extend outwardly to provide a smooth transition and/or enhance a seal between the gasket member 12 and the biological annulus 90.

Turning to FIG. 5B, the gasket member 12 may then be expanded or at least partially released within the biological annulus 90, e.g., to dilate the biological annulus 90 or otherwise direct the surrounding tissue 98 outwardly. For example, the latch 68 on the delivery tool 60 (not shown, see FIG. 2) may be actuated to remove the tension on the leaders 50, whereupon the annular ring 18 may resiliently expand against the tissue surrounding the biological annulus 90. This may substantially stabilize or secure the gasket member 12 relative to the biological annulus 90. Once stabilized, the leaders 50 may be released entirely from the delivery tool 60, e.g., by actuating lever 66 (not shown, see FIG. 2). In an alternative embodiment, a dilation tool (not shown) may be advanced into the gasket member 12 and expanded to forcibly (e.g., plastically) expand the annular ring 18 within the biological annulus 90.

With the annular ring 18 deployed within the biological annulus 90, the sewing cuff 20 may contact the tissue surrounding the supra-annular space above the biological annulus 90, as shown in FIG. 5B. One or more fasteners 96, e.g., clips, staples, sutures, and the like, may be directed through the gasket member 12 into the tissue 98 above and/or surrounding the biological annulus 90. For example, as shown, a plurality of clips 96 may be driven through the sewing cuff 20 into the surrounding tissue 98, similar to the method shown in FIGS. 14A-14C and described elsewhere herein. Exemplary fasteners and methods for using them to secure the gasket member 112 may be found in U.S. Publication Nos. US 2004/0122516, filed as Ser. No. 10/327,821, US 2005/0043760, filed as Ser. No. 10/646,639, US 2005/0080454, filed as Ser. No. 10/681,700, and US 2006/0122634, filed as Ser. No. 11/004,445, the entire disclosures of which are incorporated by reference herein.

Turning to FIG. 5B, with the gasket member 12 within the biological annulus 90, the valve member 14 may then be advanced into the patient's body towards the biological annulus 90. In the embodiment shown, the valve member 14 may be advanced along the leaders 50 toward the gasket member 12. Before advancing the valve member 14, the second or free ends 52 of the leaders 50 may be directed through respective portions of the valve member 14. Thus, before advancing the valve member 14, the leaders 50 need to be released and/or removed completely from the delivery tool 60, as described above.

In the exemplary embodiment shown in FIG. 5B, the leaders 50 may be directed through respective portions of the fabric covering 35, e.g., adjacent the commissures 34. For example, the second ends 52 of the leaders 50 may include needles (not shown) that may be directed through desired portions of the fabric covering 35 to pick up one or more threads. Optionally, the valve member 14 may include receptacles (not shown) attached to the frame 32 and/or fabric covering 35, and the fabric covering 35 may include slits or other openings through which the leaders 50 may be introduced to pass the leaders 50 through the receptacles, e.g., similar to the embodiments shown in FIGS. 20A-20E and FIGS. 24A-26 and described elsewhere herein.

Alternatively, as shown in FIG. 6, if the valve member 14 includes introducers 76, the second ends 52 of the leaders 50 may be backloaded through respective introducers 76. In a further alternative, shown in FIG. 7, the valve may include receivers 76' through which the leaders 50 may be directed.

With the leaders 50 received through the valve member 14, the valve member 14 may be advanced distally over the leaders 50 towards the gasket member 12, i.e., in the direction of arrow 94, until the valve member 14 engages or otherwise contacts the gasket member 12. As shown in FIG. 5B, the leaders 50 may include ratcheting or other retention elements 54 over which the valve member 14 may pass. For example, the retention elements 54 may include tapered proximal edges 54a, which may provide a smooth transition that allows the retention elements 54 to pass freely through the fabric covering 35, receptacles (not shown), or introducers 76, 76.'

Because of the blunt distal edges 54b, however, the valve member 14 may not be withdrawn back over the retention elements 54. Thus, the retention elements 54 may allow unidirectional advancement of the valve member 14, i.e., towards the gasket member 12.

In an exemplary embodiment, the retention elements 54 may be disposed a predetermined distance from the first ends 51 of the leaders 50, thereby securing the valve member 14 against or immediately adjacent the gasket member 12. The predetermined distance may be set such that the frame 32 of the valve member 14 substantially contacts the sewing cuff 20, e.g., to at least partially compress the core, which may enhance sealing between the valve member 14 and the gasket member 14.

In addition or alternatively, one or more knots may be directed down the leaders 50 after the valve member 14 engages or contacts the gasket member 12. In another alternative, if the gasket member 12 includes a collar (not shown, see, e.g., FIG. 8C) extending above the sewing cuff 20, the collar may include a drawstring or other connector(s) (also not shown) that may be tightened around the frame 32 of the valve member 14 to secure the valve member 14 relative to the gasket member 12. In further alternatives, the valve member 14 and/or gasket member 12 may include one or more cooperating connectors, e.g., clips, detents, and the like, that may self-engage when the valve member 14 is docked to the gasket member 12, similar to the embodiments described in the references incorporated by reference above.

Turning to FIG. 5C, once the valve member 14 is secured to the gasket member 12, the leaders 50 may be cut or otherwise severed, thereby providing a heart valve assembly 10 implanted within the biological annulus 90. As shown, the leaders 50 are severed above the retention elements 54 used to secure the valve member 14 to the gasket member 12. If the leaders 50 are knotted to secure the valve member 14 to the gasket member 12, the leaders 50 may be severed above the knots. Optionally, the leaders 50 may include weakened regions (not shown) above the retention elements 54 or otherwise disposed a predetermined distance from the first ends 51. When a predetermined tension is applied to the leaders 50 (greater than that used to compress and/or secure the gasket member to the delivery tool 60), the weakened regions may automatically fail, thereby separating the first ends 51 from the remainder of the leaders 50, which may then be removed from the patient's body. This alternative may eliminate the need to introduce scissors or other cutting tools into the patient to cut the leaders 50. If desired, e.g., in an acute emergency situation or if the valve member 14 is being replaced, the remaining leaders may be cut below the retention elements 54 to release the valve member 14, allowing the valve member 14 to be removed from the gasket member 12 and/or patient's body.

With additional reference to FIG. 6, if the valve member 14 includes removable introducers 76, the introducers 76 may be removed from the valve member 14 immediately before, while, or immediately after the valve member 14 is secured to the gasket member 12. For example, the introducers 76 may be removed simply by directing the introducers 76 proximally over the leaders 50, i.e., out of the fabric or frame of the valve member 14 and over the second ends 52 of the leaders 50. Alternatively, as shown in FIG. 7, the introducers 76' may be pockets formed from fabric, metal, or polymeric material, separately attached or integrated with the frame 32 and/or fabric covering 35 of the valve member 14. In this alternative, the introducers 76' may interact with the retention elements 54 on the leaders 50 to prevent removal of the valve member 14 away from the gasket member 12.

Figure 8A:
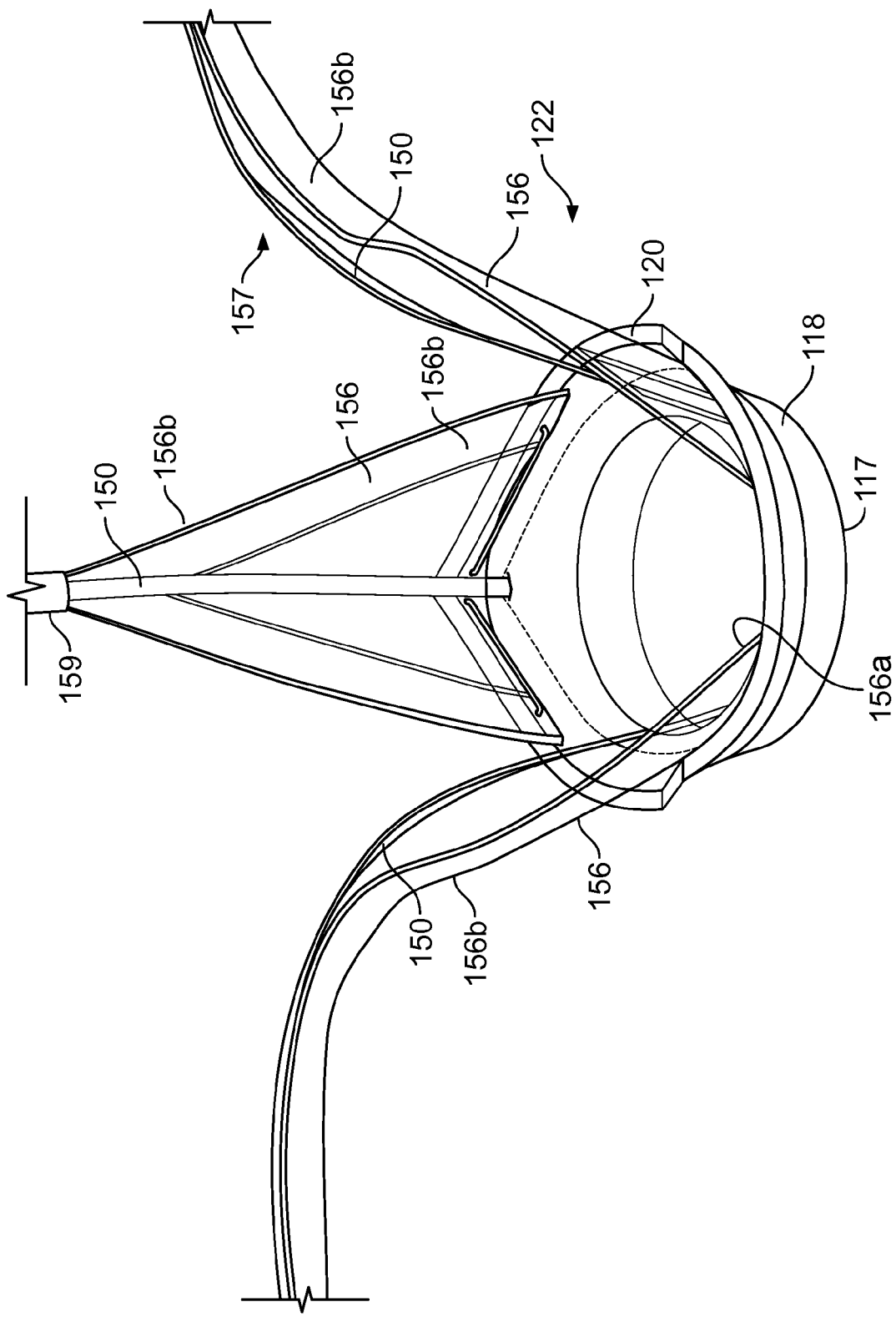
FIGS. 8A and 8B are perspective and top views, respectively, of another embodiment of a gasket member including a plurality of guide rails and guide shields.
Figure 8B:
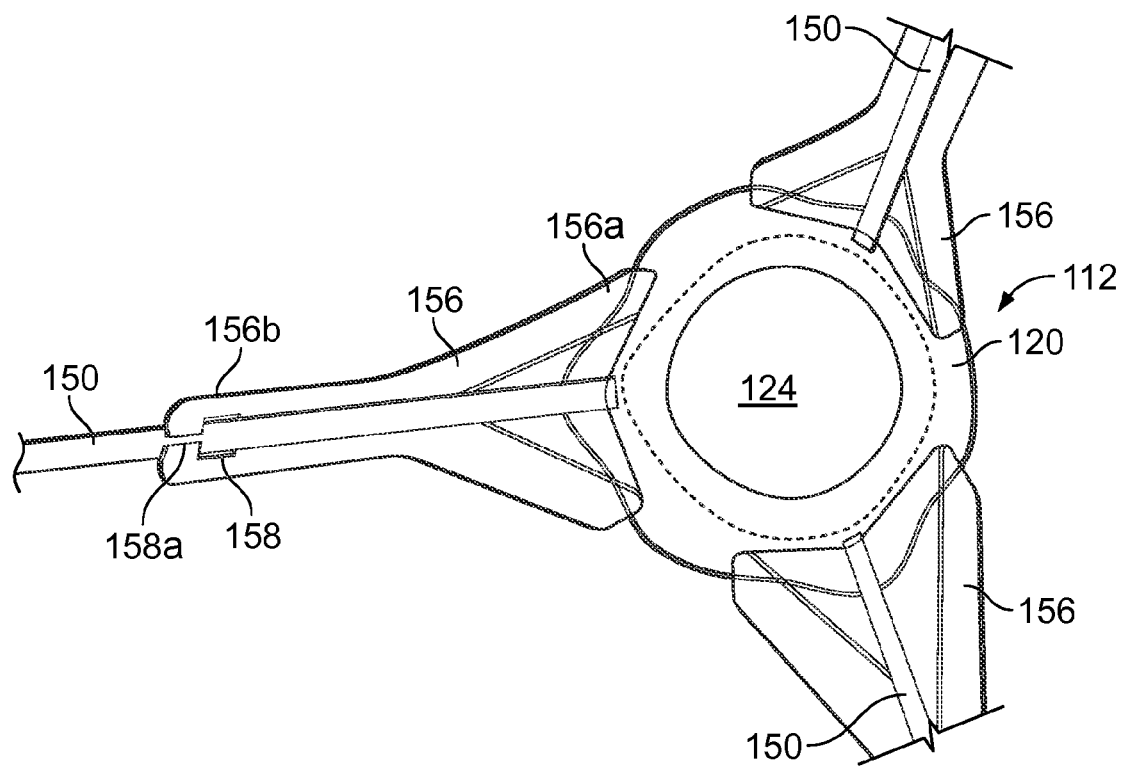
Figure 8C:
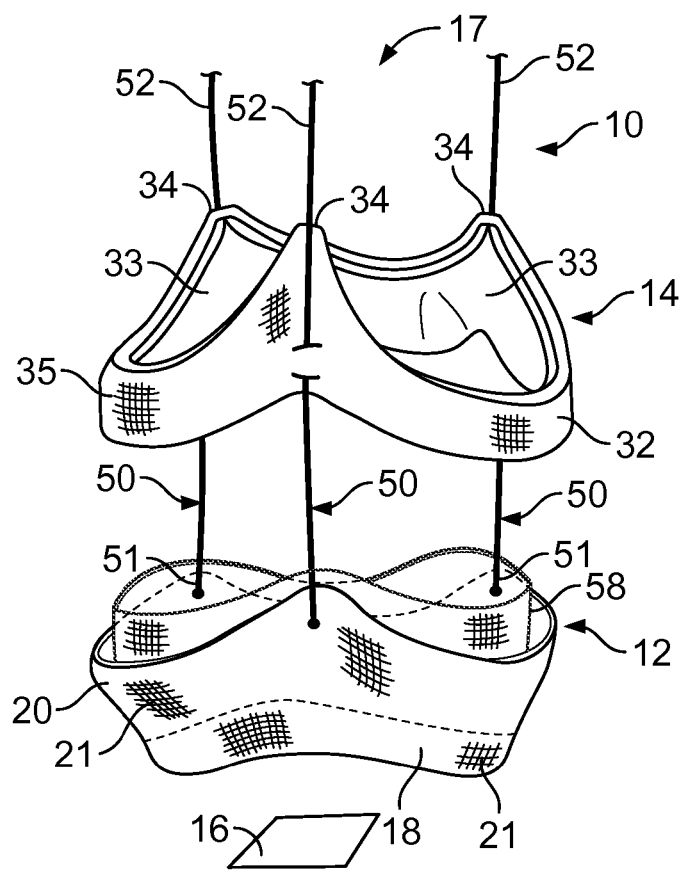
FIG. 8C is a perspective view of an alternative embodiment of a gasket member, including a collar extending upwardly for receiving a valve member therein.

Turning to FIGS. 8A and 8B, another embodiment of a gasket member 112 is shown that includes an annular ring 118, a sewing cuff 120, and a plurality of elongate guide rails or other leaders 150 extending from the sewing cuff 120 or other portion of the gasket member 12, e.g., similar to other embodiments herein. Optionally, the gasket member 112 may also include a flexible skirt and/or baleen elements (not shown), e.g., surrounding the annular ring 118. A fabric covering may be provided on one or more components of the gasket member 112, e.g., over the annular ring 118 and over a core of the sewing cuff 120, also as described elsewhere herein.

In addition, the gasket member 112 includes a plurality of guide shields 156 removably attached to the gasket member 112, e.g., by one or more sutures to the sewing cuff 120. The guide shields 156 may extend upwardly and/or outwardly from the sewing cuff 120, e.g., to at least partially define a passage 124 for guiding a valve prosthesis (not shown) downwardly towards the gasket member 112, as described further below. In a relaxed condition, the guide shields 156 may extend diagonally outwardly from the gasket member 112, but may be deflectable radially inwardly towards a central axis 117 of the gasket member 112, e.g., during delivery.

The guide shields 156 may be formed from a relatively thin and/or transparent sheet, e.g., a plastic such as polyester or Mylar or any other polymeric film or material, such as high-density or low-density polyethylene, polystyrene, and the like. The sheet may be cut or otherwise formed to include one or more bands, e.g., defining a relatively wide base that may be attached to the gasket member 112 and a relatively narrow loose upper end. For example, as shown in FIG. 8A, the guide shields 156 may have a generally triangular shape, e.g., with a wider base 156a and a narrower upper end 156b. Optionally, as shown, a center of the guide shields may be removed to provide diagonal or inverted "V" bands extending from the upper end 156b down to the base 156a. Alternatively, the guide shields 156 may have a substantially continuous "mandolin" or inverted "Y" shape, as shown in FIG. 8B, and described further in co-pending application Ser. No. 60/914, 742, incorporated by reference herein.

Optionally, the upper ends 156b may include one or more features that partially restrain the guide rails 150 away from the passage 124 or otherwise out of the operator's field of view during a procedure. For example, as shown in FIG. 8A, the upper ends 156b may include one or more bands 159 that may be wrapped around the guide rails 150 to releasably constrain the guide rails 150 to the guide shields 156. In addition or alternatively, as shown in FIG. 8B, the upper ends 156b may include openings 158 that may receive the guide rails 150. Optionally, the upper ends 156b of the guide shields 156 may be split, e.g., at 158a down to the openings 158 or diagonally from the openings 158 (not shown), to facilitate inserting and/or removing the guide rails into/from the openings 158, as shown in FIG. 8B.

The guide shields 156 may be attached to the sewing cuff 120, e.g., by one or more sutures (not shown) sewn through fabric of the sewing cuff 120 (and/or other portion of the gasket member 12) and holes (also not shown) in the base 156a. Optionally, a chain stitch or other stitch may be used, e.g., that may unravel upon being cut at a single location, which may facilitate removing the sutures and, consequently, the guide shields 156 after implantation. Additional information on methods for removably attaching the guide shields 156 to the gasket member and/or methods for using the guide shields 156 may be found in co-pending application Ser. No. 60/914,742, incorporated by reference herein.

Figure 9A:
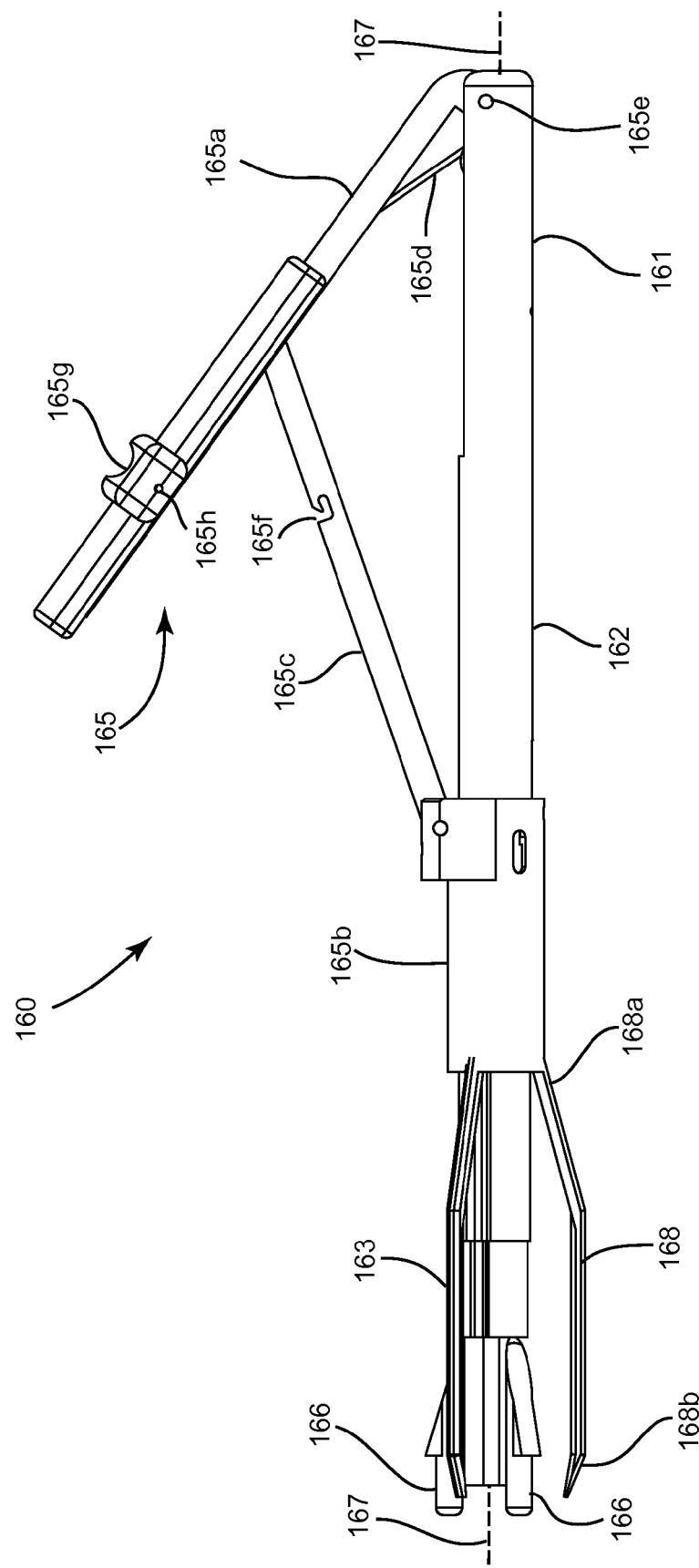
FIGS. 9A-9C are side, perspective, and end views, respectively, of a tool for delivering the gasket member of FIGS. 8A and 8B.
Figure 9B:
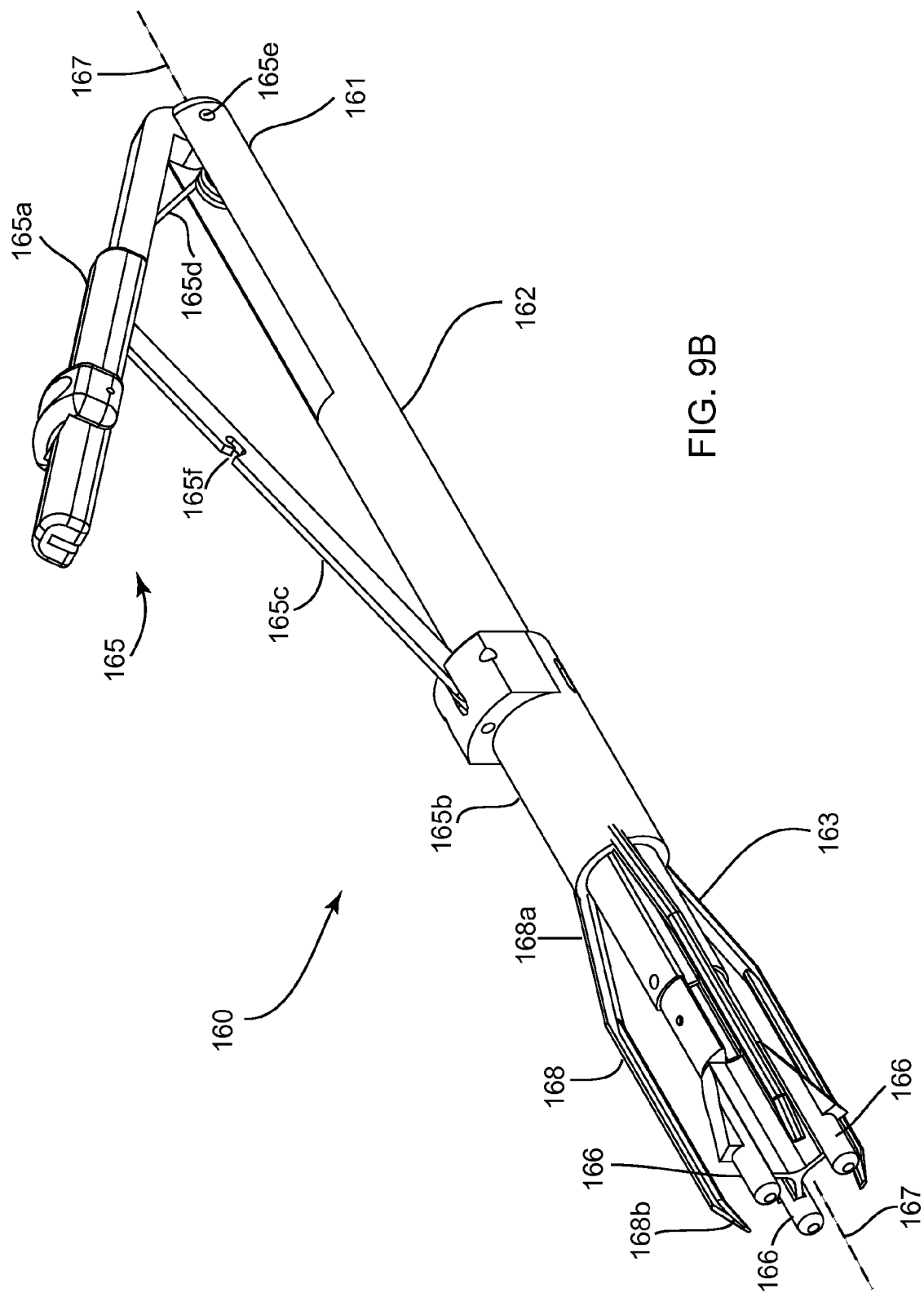
Figure 9C:
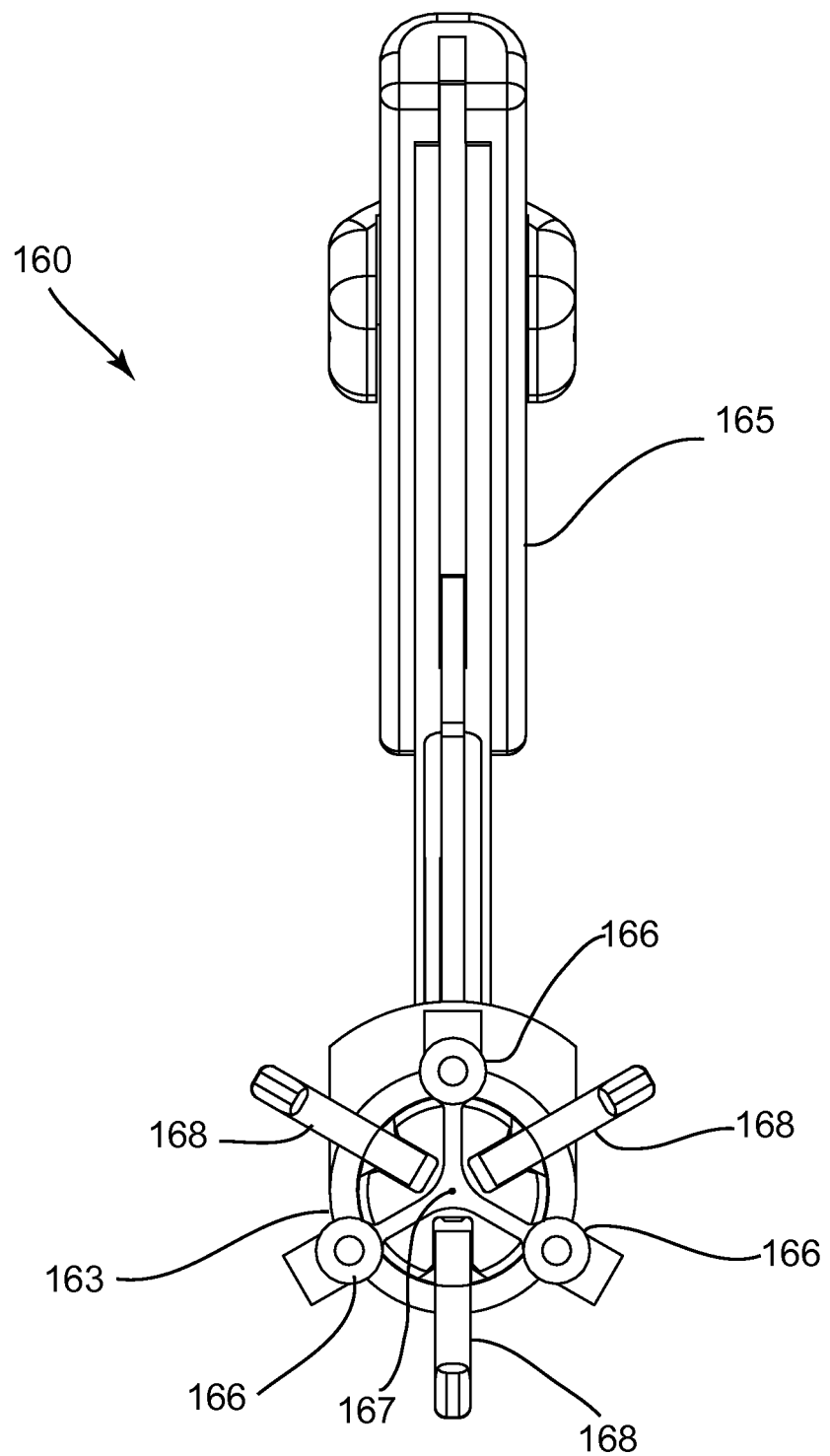

Turning to FIGS. 9A-9C, an exemplary embodiment of a gasket delivery tool 160 is shown that generally includes an elongate shaft 162 including a proximal end 161, a distal end 163, and an actuator 165 on the proximal end 161. With additional reference to FIGS. 10A and 10B, the delivery tool 160 includes a plurality of supports 166 on the distal end, e.g., spaced apart around a longitudinal axis 167 of the tool 160. The supports 166 may be substantially rigid cylindrical hubs for receiving a gasket member 112 (such as any of those described herein) around the supports 166. The supports 166 may generally define a diameter that is smaller than the gasket member 112, e.g., smaller than the radius of the annular ring 118. The supports 166 may be formed as a single piece, e.g., integrally molded, machined, and the like, or may be separate shafts and/or other components attached to one another and/or the distal end 163 of the gasket delivery tool 160. Alternatively, a hub or base having a circular or other multiple lobed shape may be provided instead of the supports 166, if desired.

Figure 10A:
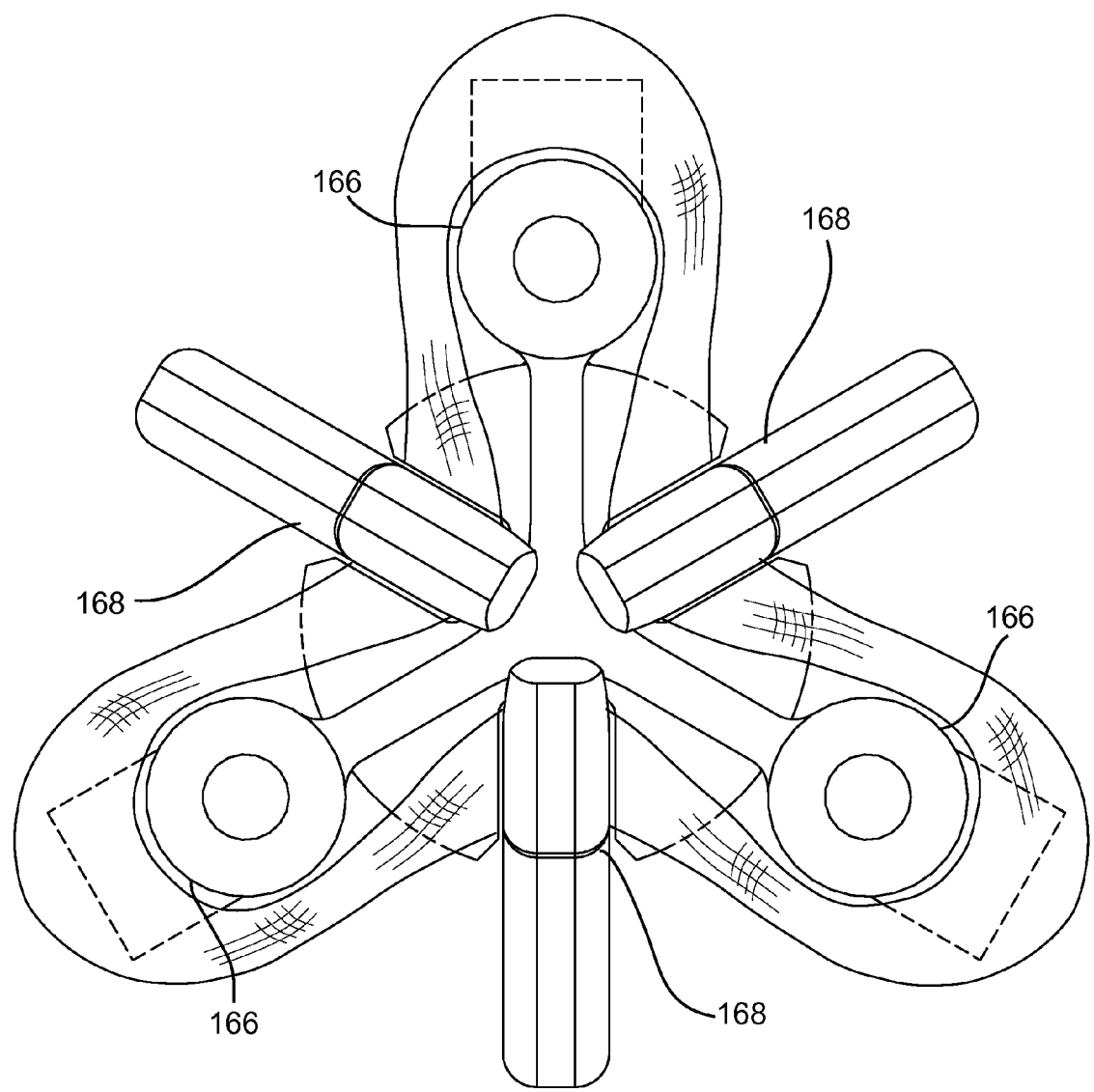
FIGS. 10A and 10B are end and side views, respectively, of a distal end of the tool of FIGS. 9A-9C, showing the gasket of FIGS. 8A and 8B secured thereto in a folded or contracted condition.
Figure 10B:
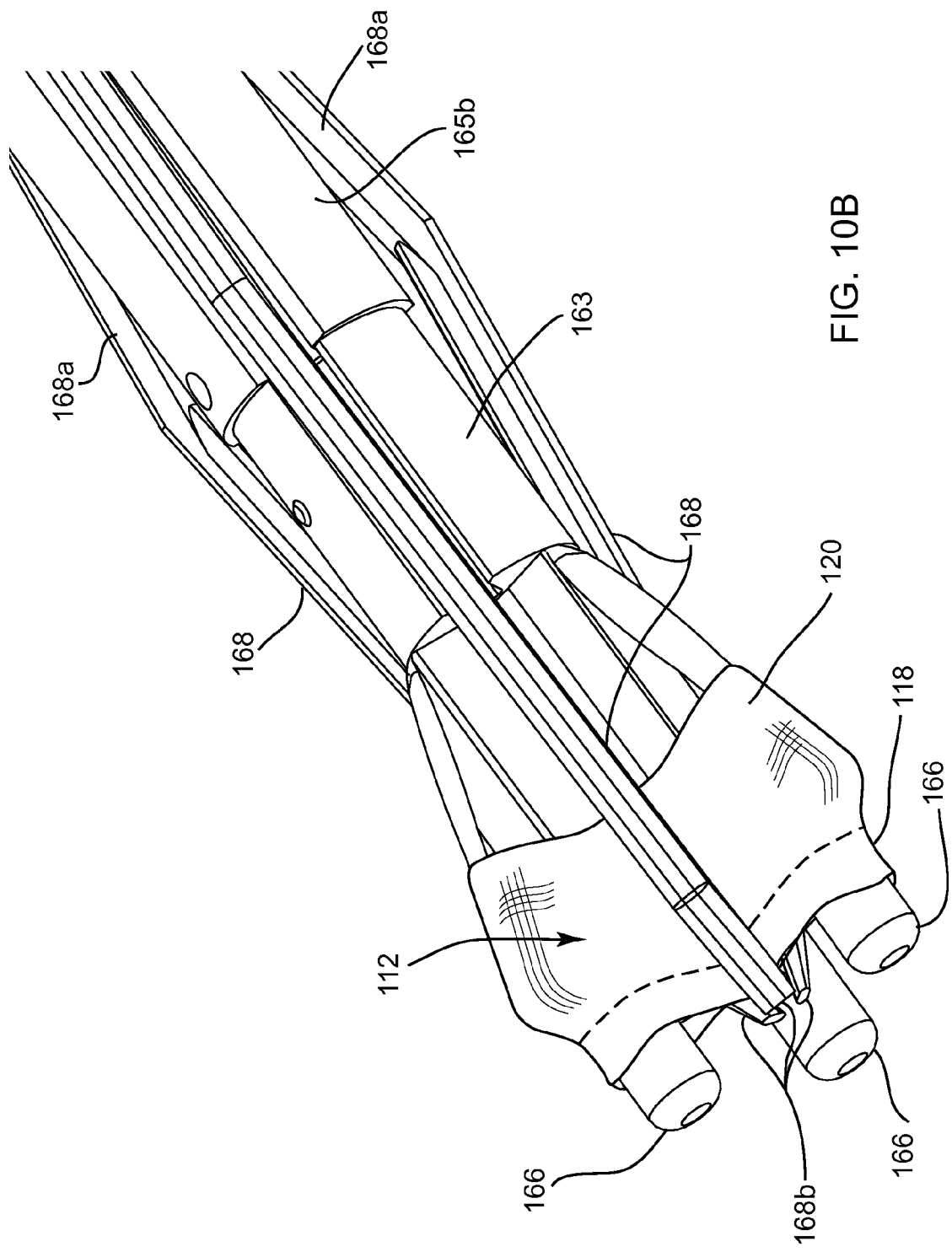

In addition, the tool 160 includes a plurality of arms 168 movably mounted to the distal end 163. For example, one end 168a of the arms 168 may be attached to the distal end 163 of the tool 160, e.g., proximal to the supports 166, and the other free end may include tips 168b disposed adjacent the supports 166. As shown, the arms 168 may be offset radially relative to the supports 166 such that each arm 168 is disposed between adjacent supports 166. The arms 168 may be movable from an outer position, e.g., as shown in FIGS. 9A and 9B, defining a radius larger than the gasket member 112 to an inner position, e.g., as shown in FIGS. 10A and 10B, wherein the tips 168b are disposed between and/or within the supports 166.

The actuator 165 may include a lever or other mechanism that may selectively move the tips 168b of the arms 168 between the outer and inner positions. For example, as shown in FIGS. 9A and 9B, the actuator 165 may include a handle 165a coupled to a sleeve 165b via a linkage 165c. The handle 165a may be biased outwardly, e.g., by a spring 165d or other biasing mechanism, thereby maintaining the arms 168 in the outer position. The handle 165a may be directed towards the shaft 162, e.g., about pivot point 165e, thereby directing linkage 165c and sleeve 165b distally, i.e., towards the distal end 163. This action causes the tips 168b of the arms 168 to move inwardly towards the inner position.

For example, the arms 168 may be deflectable radially inwardly by an inward force applied to the arms 168 as the sleeve 165b passes over the first ends 168a. The arms 168 may be sufficiently resilient to return outwardly when the sleeve 165b is retracted from over the first ends 168a. Alternatively, the arms 168 may include hinges or other components coupled to the sleeve 165b and/or linkage 165c such that the arms 168 are movable inwardly and outwardly.

The handle 165a may be temporarily locked against the shaft 162 with the arms 168 in the inner position, e.g., by a lock or other interlocking features (not shown) on the handle 165a, linkage 165c, and/or shaft 162. For example, the linkage 165c may include a slot 165f and the handle 165a may include a sliding button, switch or other control 165g that includes a cross pin 165h that may be received in the slot 165f when the handle 165a is directed against the shaft 162. The control 165g may be manually moved to engage and/or disengage the cross pin 165h and the slot 165f. Optionally, the control 165g may be biased, e.g., towards or away from the end of the handle 165a, for example by a spring (not shown), such that when the handle 165a is directed against the shaft 162, the cross pin 165h slides into the slot 165f, preventing subsequent movement of the handle 165a. The control 165g may be directed against the bias of the spring, e.g., distally or proximally, to release the cross pin 165h from the slot 165f, whereupon the spring 165d may then bias the handle 165a outwardly. Thus, the slot 165f may be oriented to engage with the cross pin 165h as the control 165g is translated along the handle 165a in a distal or proximal direction, and to release the cross pin 165h as the control 165g is translated in an opposite proximal or distal direction. When it is desired to release the handle 165a and arms 168 back to the outer position, the control 165g may be released, whereupon the spring 165d may then bias the handle 165a outwardly, thereby automatically opening the arms 168 towards the outer position. Alternatively, the levers involved may be designed such that the bias of the spring 165d is removed when the handle 165a is directed against the shaft 162, thereby maintaining the arms 168 in the inner position. In this alternative, the handle 165a may simply be pulled away from the shaft 162 such that the spring 165d again biases the handle 165a to move outwardly, directing the arms 168 to the outer position.

During use, with the arms 168 in the outer position, a gasket member 112 may be placed between the supports 166 and the arms 168, e.g., with the nadir regions of the sewing cuff 120 aligned radially with the arms 168 and the commissure regions of the sewing cuff 120 aligned radially with the supports 166. The arms 168 may then be directed to the inner position, thereby securing the gasket member 112 between the supports 166 and the arms 168. As shown in FIGS. 10A and 10B, the gasket member 112 may be deformed from a generally circular expanded condition to a multiple lobed, e.g., "shamrock" shaped contracted condition defining lobes, similar to the other embodiments and tools described above. The gasket member 112 may be elastically deformed into the contracted condition or plastically deformed, e.g., in a martensitic state, similar to the previous embodiments.

Figure 11A:
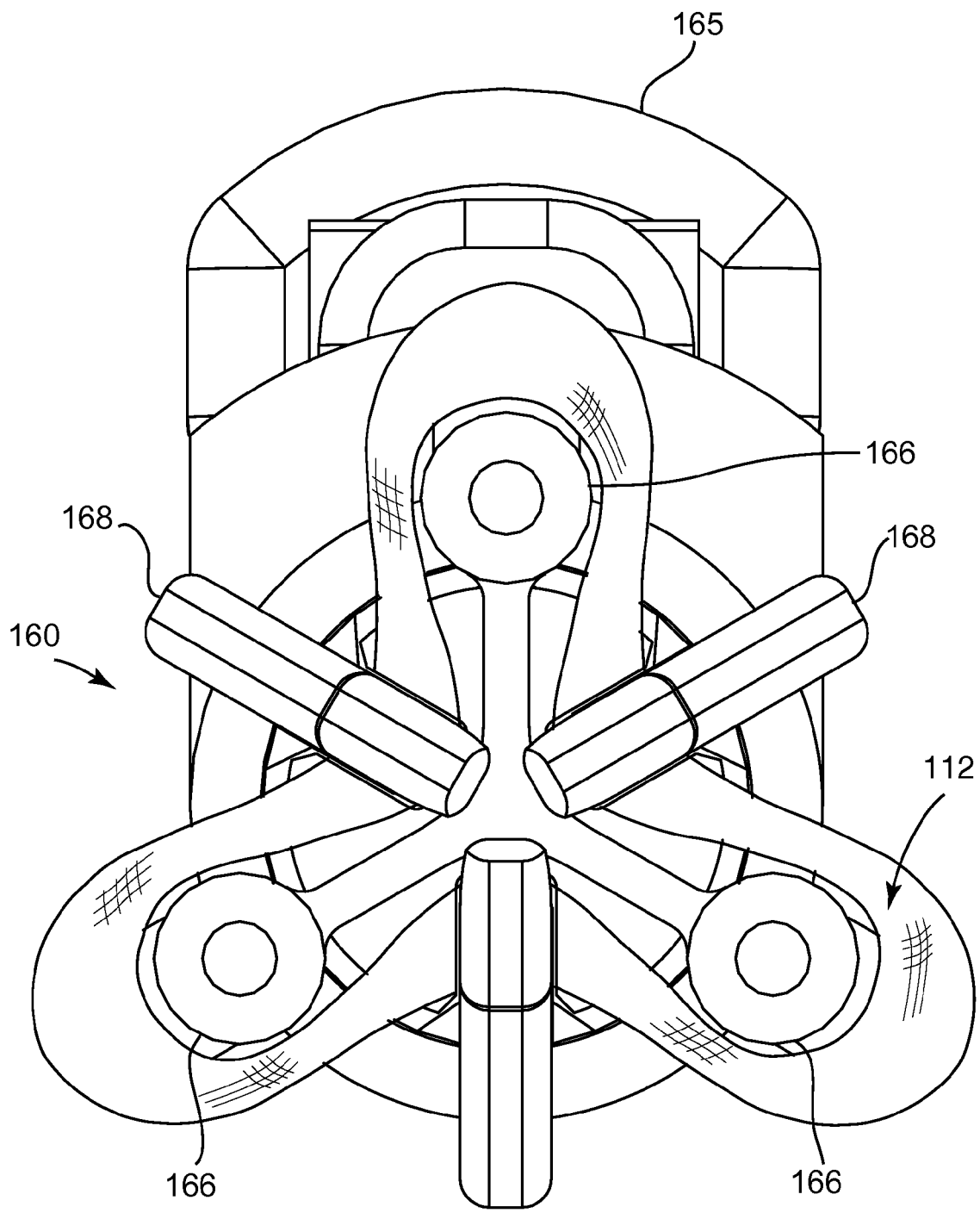
FIGS. 11A-11E show the gasket member of FIGS. 10A and 10B being delivered into a biological annulus (FIG. 11B) in a contracted condition (FIGS. 11A, 11C, 11D), aligned with commissures of the annulus (FIGS. 11B, 11C), and released from the tool (FIG. 11E).
Figure 11B:
Figure 11C:
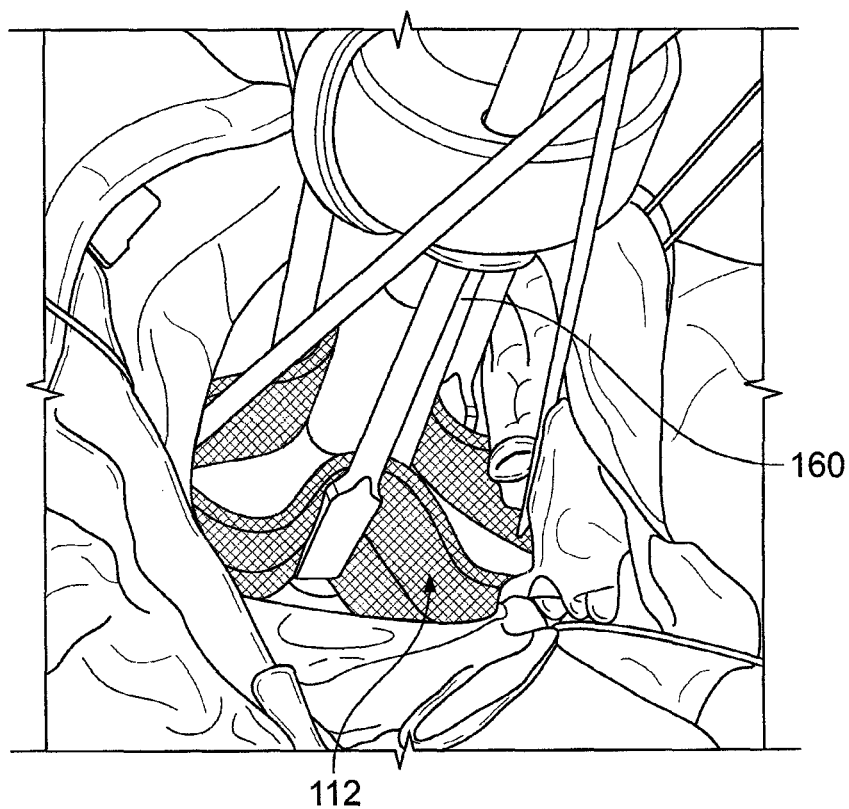
Figure 11D:
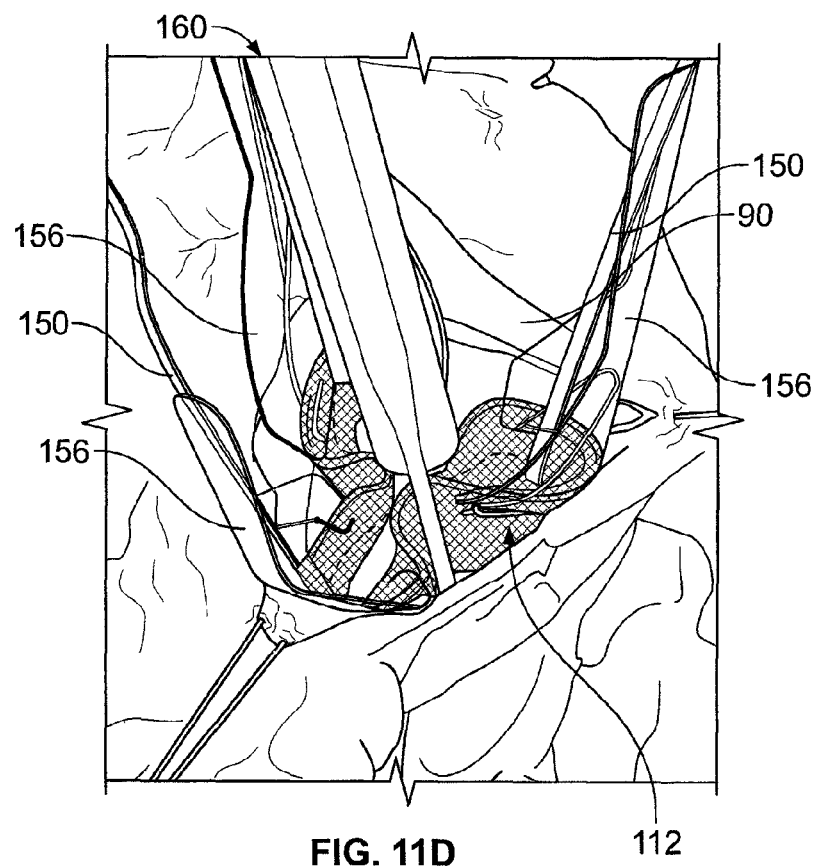
Figure 11E:
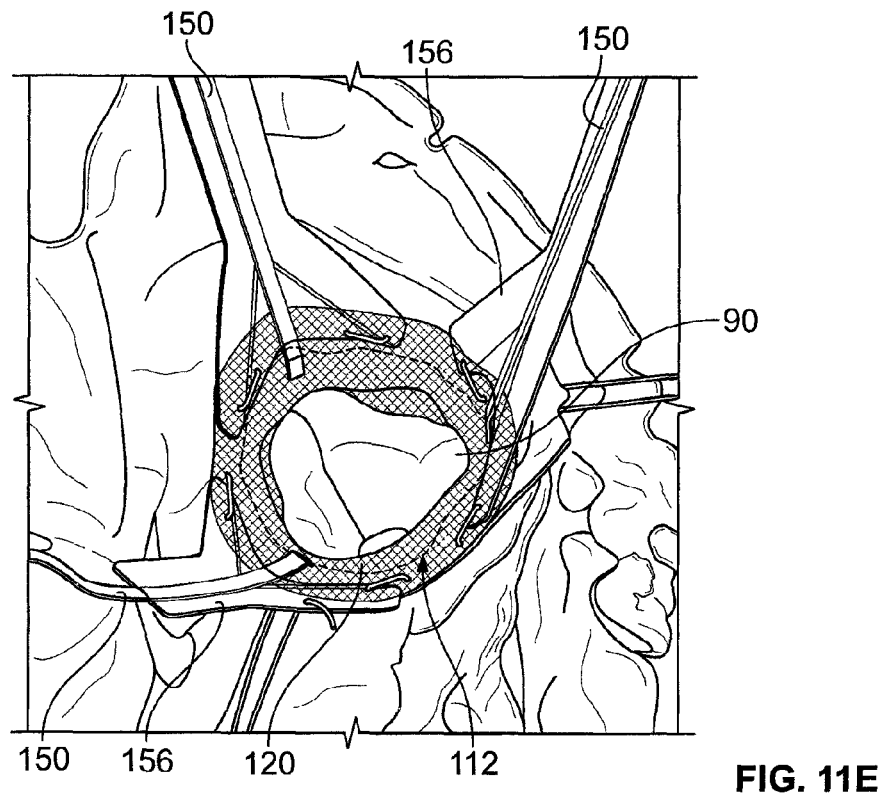

Turning to FIGS. 11A-11E, during use, the tool 160 may be loaded with the gasket member 112, as shown in FIG. 11A, and then directed into a biological annulus 90, e.g., as best seen in FIG. 11B. As shown in FIG. 11C, the tool 160 may be rotated about its longitudinal axis 167 to align the lobes or "ears" of the gasket member 112 with the commissures 91 of the biological annulus 90. Turning to FIGS. 11D and 11E, the arms 168 may then be directed to the outer position, thereby releasing the gasket member 112.

As shown in FIG. 11E, the gasket member 112 may resiliently expand towards its original expanded condition when released, thereby contacting tissue surrounding the biological annulus 90. The tool 160 may be removed, leaving the gasket member 112 in place within the biological annulus 90. As shown, the annular ring of the gasket member 112 may be located within a native valve annulus, while the sewing cuff 120 may be located in a supra-annular position relative to the native valve annulus. If the gasket member 112 includes guide rails 150 and/or guide shields 156, the guide rails 150 and/or guide shields 156 may extend upwardly from the biological annulus 90, e.g., to a location above the biological annulus and/or outside the patient's body, as described elsewhere herein.

Figure 12:
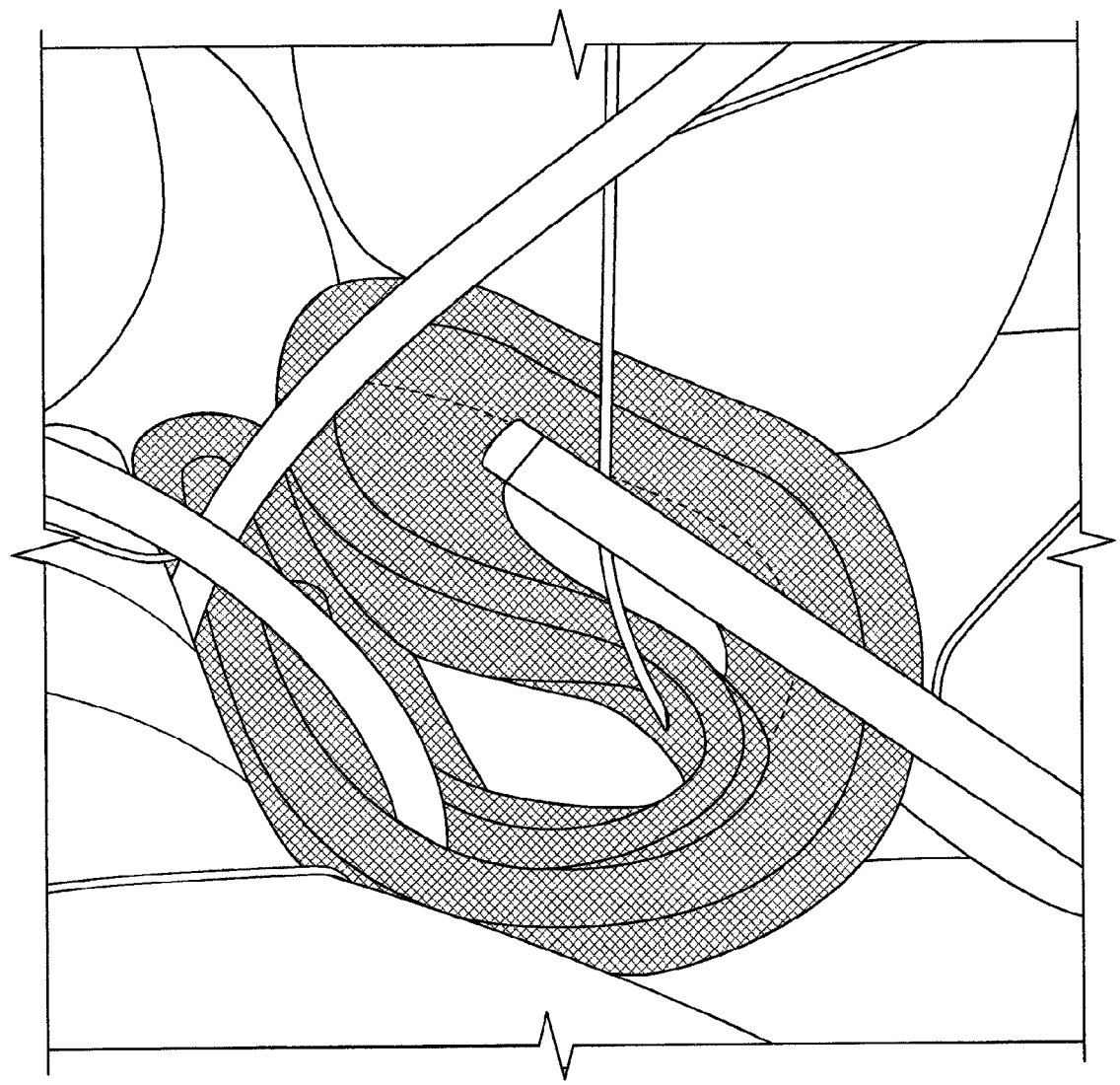
FIG. 12 is an end view of an alternate contracted configuration for the gasket member of FIGS. 8A and 8B, e.g., having a folded shape.

FIG. 12 shows an alternate contracted configuration for the gasket member 112, which may be used instead of the multiple lobed or "shamrock" contracted condition shown in FIG. 10A. As shown in FIG. 12, the gasket member 112 may be folded into a generally "C" shaped or rolled shape in the contracted condition, rather than the multiple lobed condition. Such a folded condition may be maintained by a tool (not shown), e.g., including one or more arms or other actuatable members (also not shown), similar to the arms 168 of the tool 160. Alternatively, the gasket member 112 may simply held by a needle driver, clamp, or other surgical instrument. Optionally, the folded ends of the gasket member 112 may be temporarily secured to one another, e.g., using one or more sutures, a band, and the like (not shown), which may be removed once the gasket member 112 is introduced into the biological annulus 90. Upon being released by the tool, the gasket member 112 of FIG. 12 may resiliently unfold or otherwise return back to its original annular shape, similar to when the gasket member 112 is released from the multiple lobed condition. The folded condition may allow the gasket member 112 to achieve a smaller cross-section than the multiple lobed condition, which may be useful when access is limited into the biological annulus.

Figure 13A:
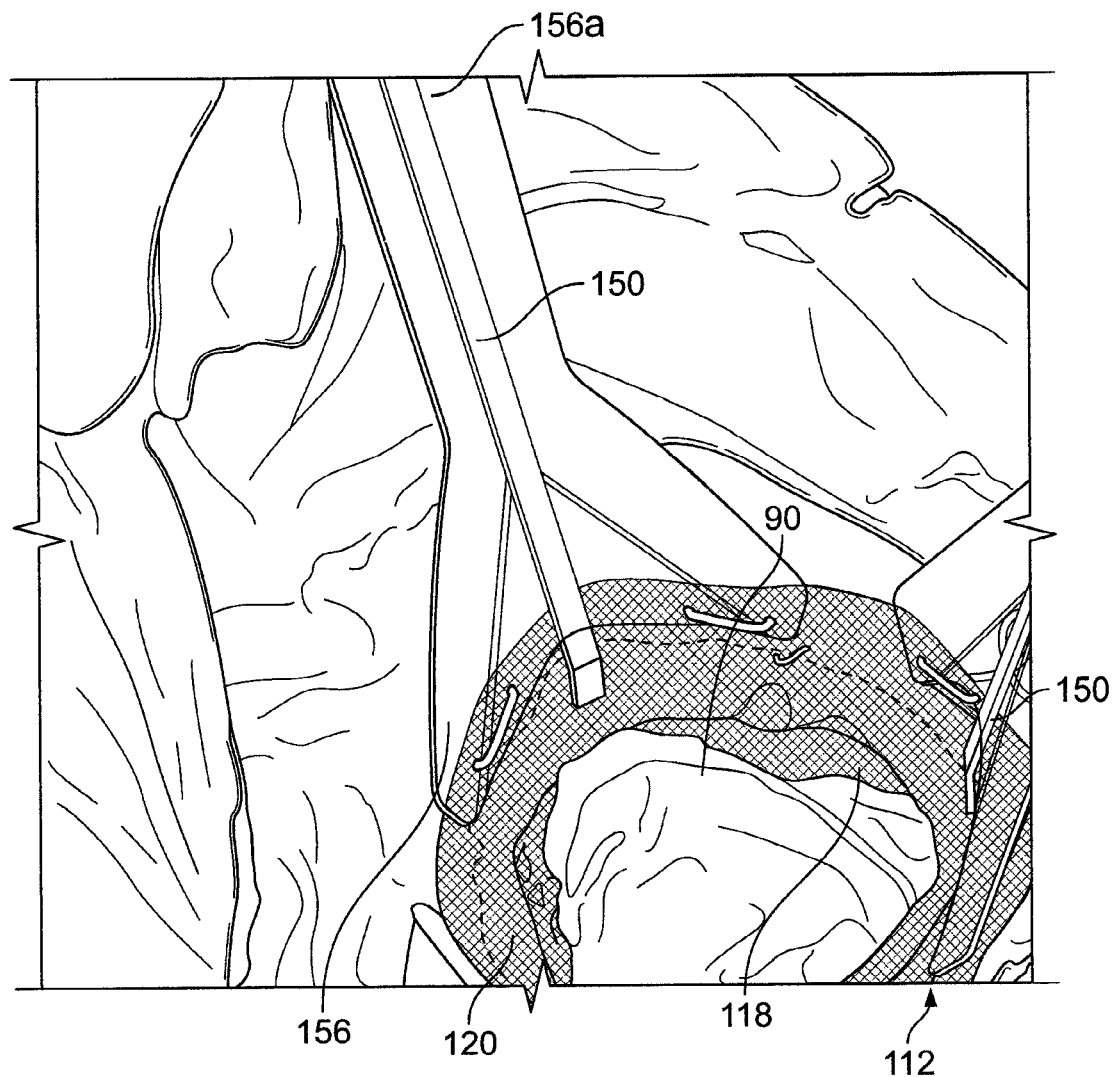
FIG. 13A is a perspective detail of a biological annulus including the gasket member of FIGS. 8A and 8B delivered therein, showing a guide shield of the gasket member.

Turning to FIG. 13A, the gasket member 112 is shown delivered into the biological annulus 90, e.g., using any of the tools and/or methods described elsewhere herein. The guide shields 156 extend upwardly and/or outwardly from the gasket member 112, thereby contacting surrounding tissue. The guide shields 156 may be sufficiently long such that upper ends of the guide shields 156 are disposed outside the patient's body and/or outside the biological annulus 90. Optionally, the upper ends 156b of the guide shields 156 may be folded outwardly, e.g., against the patient's chest or other anatomy, to maintain a passage through the guide shields 156 open and/or move the uppers ends 156b out of the field of view. In addition or alternatively, the upper ends 156b may also be held by sutures, clips, clamps, and the like (not shown), e.g., to help tension or retract the guide shields 156 in order to maintain the field of view open. The guide shields 156 may at least partially define a passage communicating with the biological annulus 90, the inner surfaces of the guide shields 156 providing a smooth and/or lubricious surface to facilitate advancing a valve prosthesis (not shown) into the biological annulus 90 towards the gasket member 112, as described further elsewhere herein.

Figure 13B:
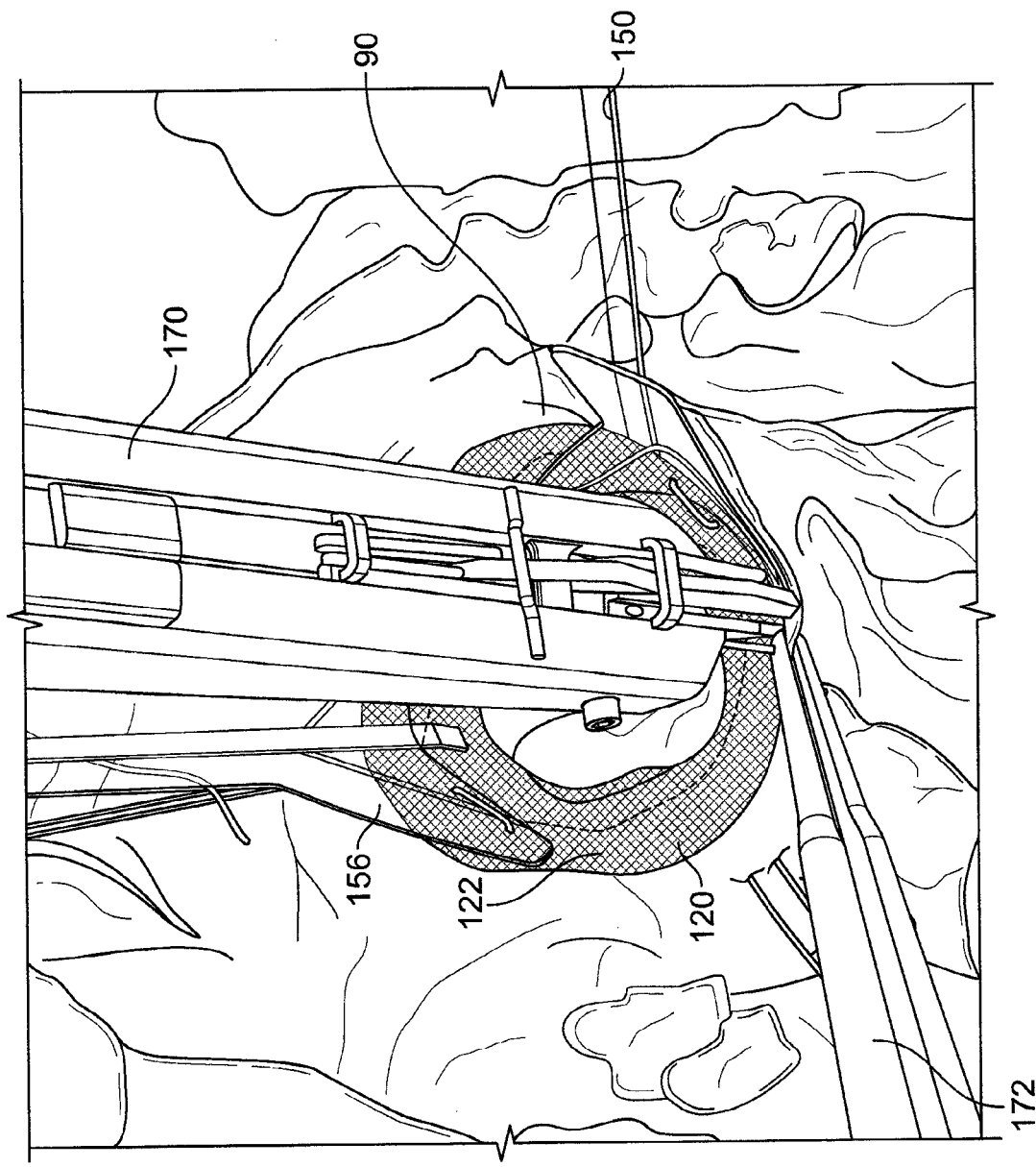
FIG. 13B is a perspective detail of the biological annulus of FIG. 13A, showing tools being used to deliver a fastener through the gasket member into surrounding tissue.
Figure 14A:
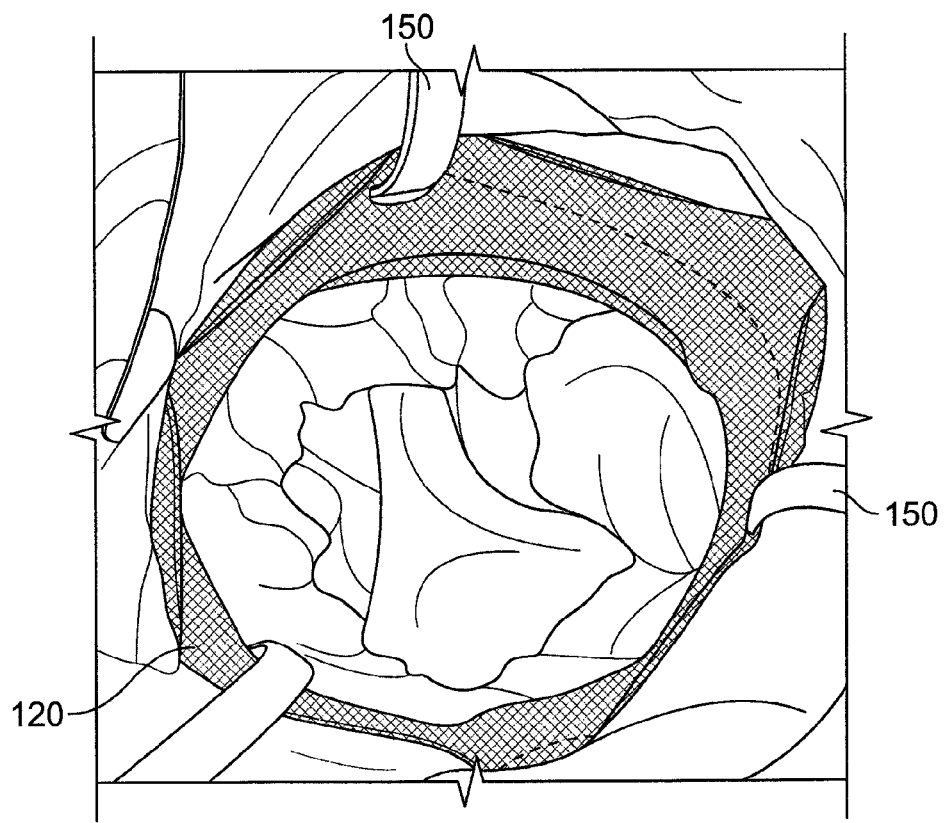
FIGS. 14A-14C are details of the biological annulus of FIGS. 13A and 13B, showing the gasket member being secured to the annulus.
Figure 14B:
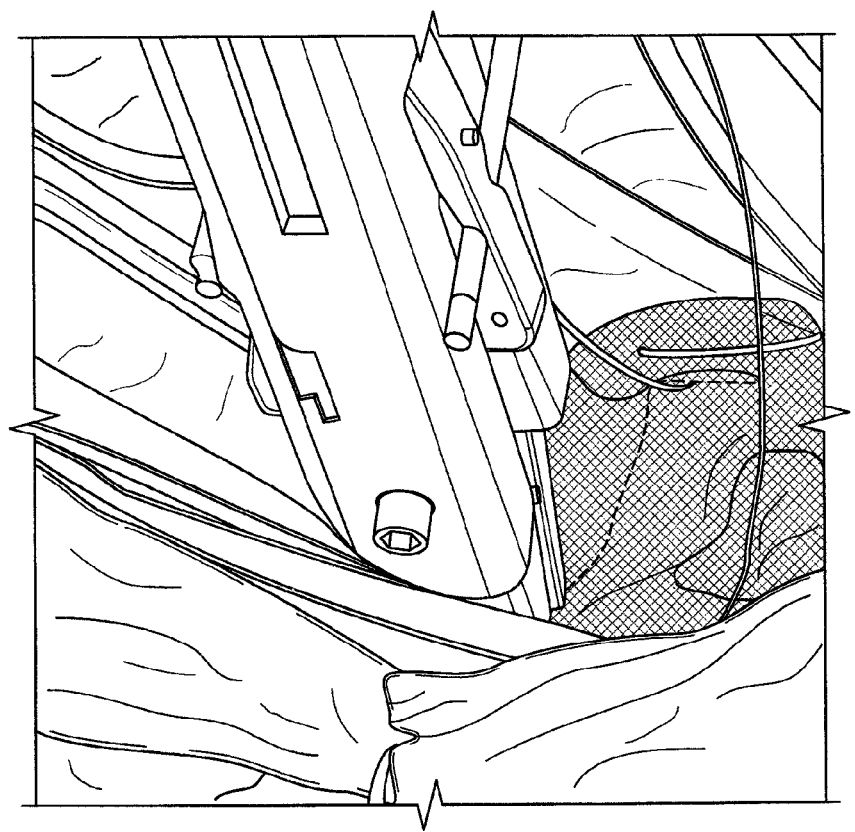
Figure 14C:
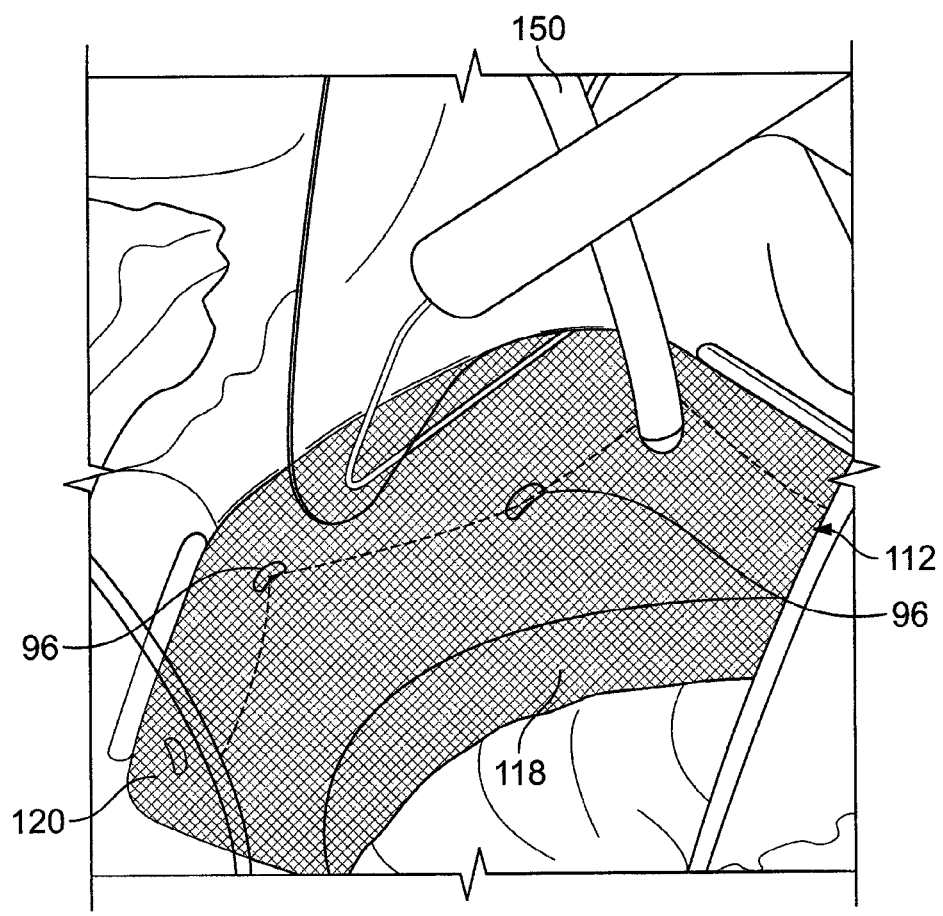

Turning to FIG. 13B, after releasing the gasket member 112 within the biological annulus 90, the gasket member 112 may be secured to the surrounding tissue. For example, as shown, a tool 170 may be used to deliver a plurality of fasteners 96 (not shown) through the sewing cuff 120 and into the surrounding tissue, as described elsewhere herein. Forceps, tweezers, or other tool 172 may be used, if desired, to manipulate components of the gasket member 112 during delivery of the fasteners 96. For example, the tool 172 may be used to hold the sewing cuff 120 and/or to move the guide rails 150 and/or guide shields 156 out of the way. Because of the orientation, configuration, and/or transparency of the guide shields 156, the guide shields 156 may not obscure observation and/or access into the biological annulus to deliver the fasteners. FIGS. 14A-14C show additional details of securing the gasket member 112 to the surrounding tissue using fasteners 96.

Turning to FIGS. 15A-17B, a valve holder tool 210 is shown that may be used to deliver a valve member 14, which may be any valve prosthesis described elsewhere herein or in the references incorporated by reference. For simplicity, only a frame of a valve member 14 is shown without leaflets or fabric covering. Generally, the valve holder 210 includes an elongate shaft 212 including a proximal end 214 and a distal end 216 defining a longitudinal axis 218 therebetween. As best seen in FIGS. 15B and 17B, the valve holder 210 may include an enlarged head or support 220 on the distal end 216, which may have a size and/or shape similar to the valve member 14 carried on the distal end 216. For example, the head 220 may have a partial dome shape, e.g., defining a cavity (not shown) under the head 220, which may protect or otherwise cover leaflets (not shown) of the valve member 14. The head 220 may include one or more openings 221 therethrough, e.g., for receiving one or more sutures 13, e.g., as shown in FIG. 17B. As shown, a suture 13 may be directed through a respective opening 221 and through fabric of the valve member 14, and then tied off and cut, thereby securing the valve member 14 to the head 220. Thereafter, during use, e.g., after implantation, the suture(s) 13 may be cut, thereby releasing the valve member 14 from the head 220, as described further below.

Returning to FIGS. 15A and 15D, the valve holder 210 also includes a plurality of tubular members 230 including open upper and lower ends 232, 233. The tubular members 230 may provide guide passages 230a for receiving guide rails 150 (not shown) of a gasket member 112 (also not shown), as described further below. The tubular members 230 may be attached to the shaft 212 of the valve holder 210, e.g., by hubs 234, 236, such that the tubular members 230 extend generally parallel to the longitudinal axis 218. As shown, the tubular members 230 include upper ends 232 that are disposed closer to the longitudinal axis 218 than lower ends 233, which may facilitate visually monitoring beyond the tubular members 230. Alternatively, the tubular members 230 may extend parallel to the longitudinal axis 218. In addition or alternatively, the tubular members 230 may be disposed against or otherwise closer to the shaft 212, although the distal ends 233 may then curve outwardly, e.g., in an "S" shape to dispose the distal ends 233 outside the head 220, e.g., as shown in FIG. 15B.

In addition, the valve holder 210 may include one or more actuators for causing separation of at least a portion of the guide rails 150 from the gasket member 112, as described further below. For example, in one embodiment, each of the tubular members 230 may be rotatable about an individual central axis 231, as shown in FIG. 15D. The passages 230a through the tubular members 230 may have a cross-section similar to the guide rails 150, e.g., having an oblong or rectangular cross-section, which may receive the guide rails 150 in a fixed angular orientation, while accommodating relative axial movement. When the tubular members 230 are rotated about the axes 231, the portion of the guide rails 150 in the passages may also rotate, thereby causing the guide rails 150 to plastically deform and break, e.g., adjacent the distal end 233 of the tubular members 230. Optionally, similar to previous embodiments, the guide rails 150 may include weakened regions that may preferentially break upon rotation of the tubular members 230. The weakened regions may include a notch, slit, groove, cut, necking, thinning, score mark, and/or narrowing on either or both edges of the guide rails 150, across the entire width of the guide rails 150, and/or axially or diagonally along the length of the guide rails 150. Optionally, a preload force or stress may be applied on the guide rails 150 when received within the tubular members 230 that is less than the tensile breaking strength of the guide rails 150, or, more specifically, less than the tensile breaking strength at the weakened region(s) of the guide rails 150. Such a preload may reduce the number of turns of the tubular members 230 necessary to break or separate the guide rails 150, e.g., by preventing the guide rails 150 from twisting, binding, and/or bunching excessively during rotation of the tubular members 230. Thus, each guide rail 150 may be separated by rotating the respective tubular member 230.

Alternatively, the entire hub 234 may be rotatable around the shaft 210, which may cause all of the guide rails 150 to separate substantially simultaneously at the weakened regions or other locations adjacent the distal ends 263. In a further alternative, shown in FIGS. 16A and 16B, the valve holder 210 may include an actuator 250 that is movable axially relative to the shaft 212, e.g., from a distal position (shown in FIG. 16A) to a proximal position (shown in FIG. 16B) for breaking the guide rails.

Figure 15C:
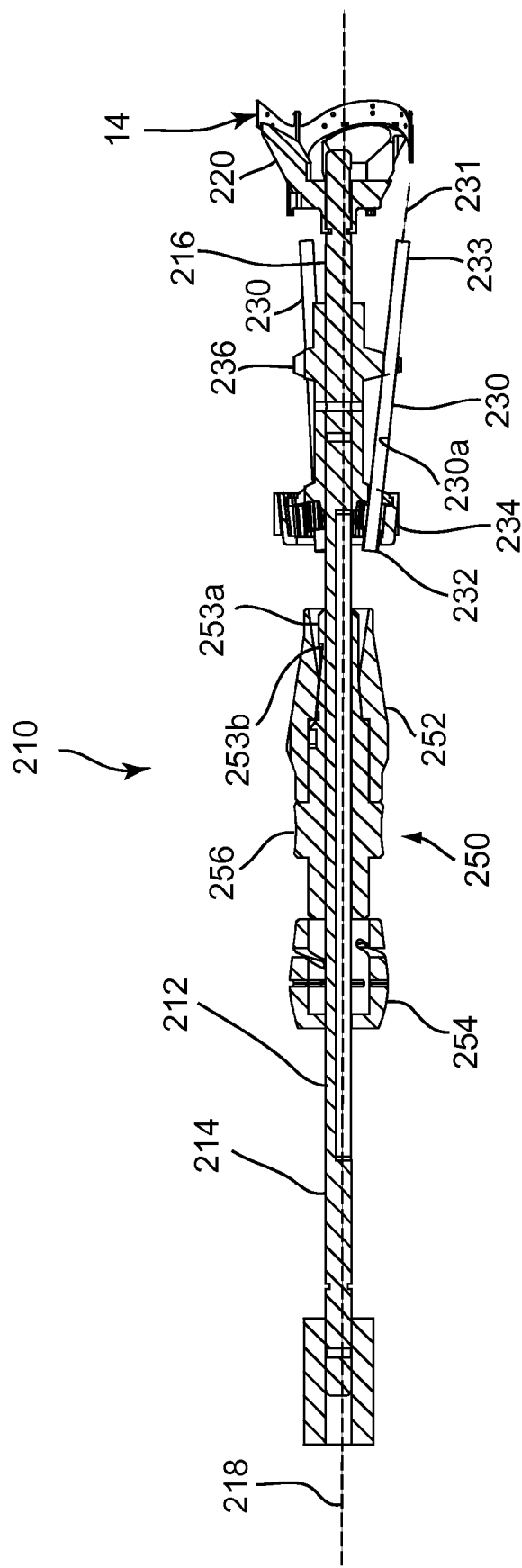
FIG. 15C is a longitudinal cross-section of the valve holder tool of FIGS. 15A and 15B, taken along line 15C-15C.
Figure 15D:
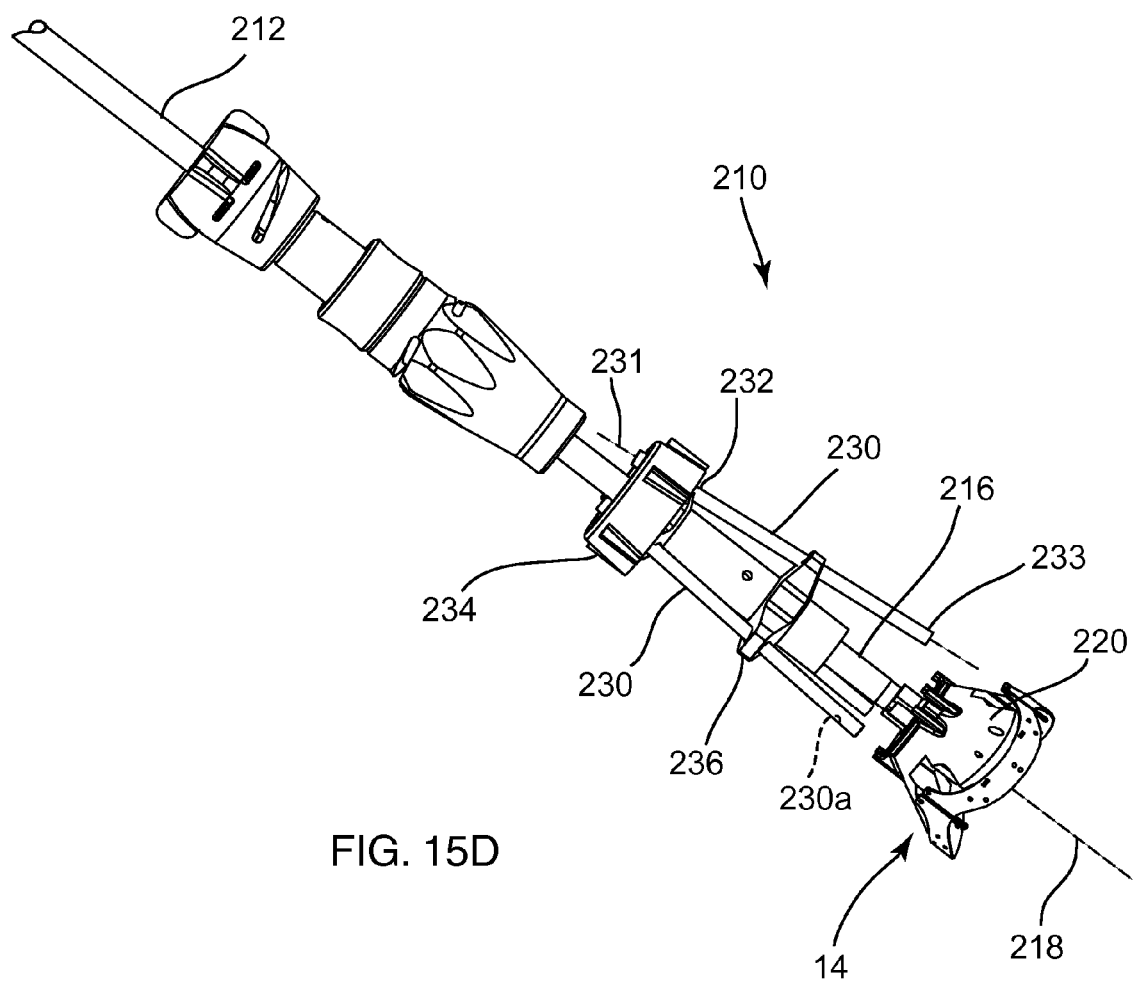
FIG. 15D is a perspective view of a distal end of the valve holder tool of FIGS. 15A-15C.
Figure 16A:
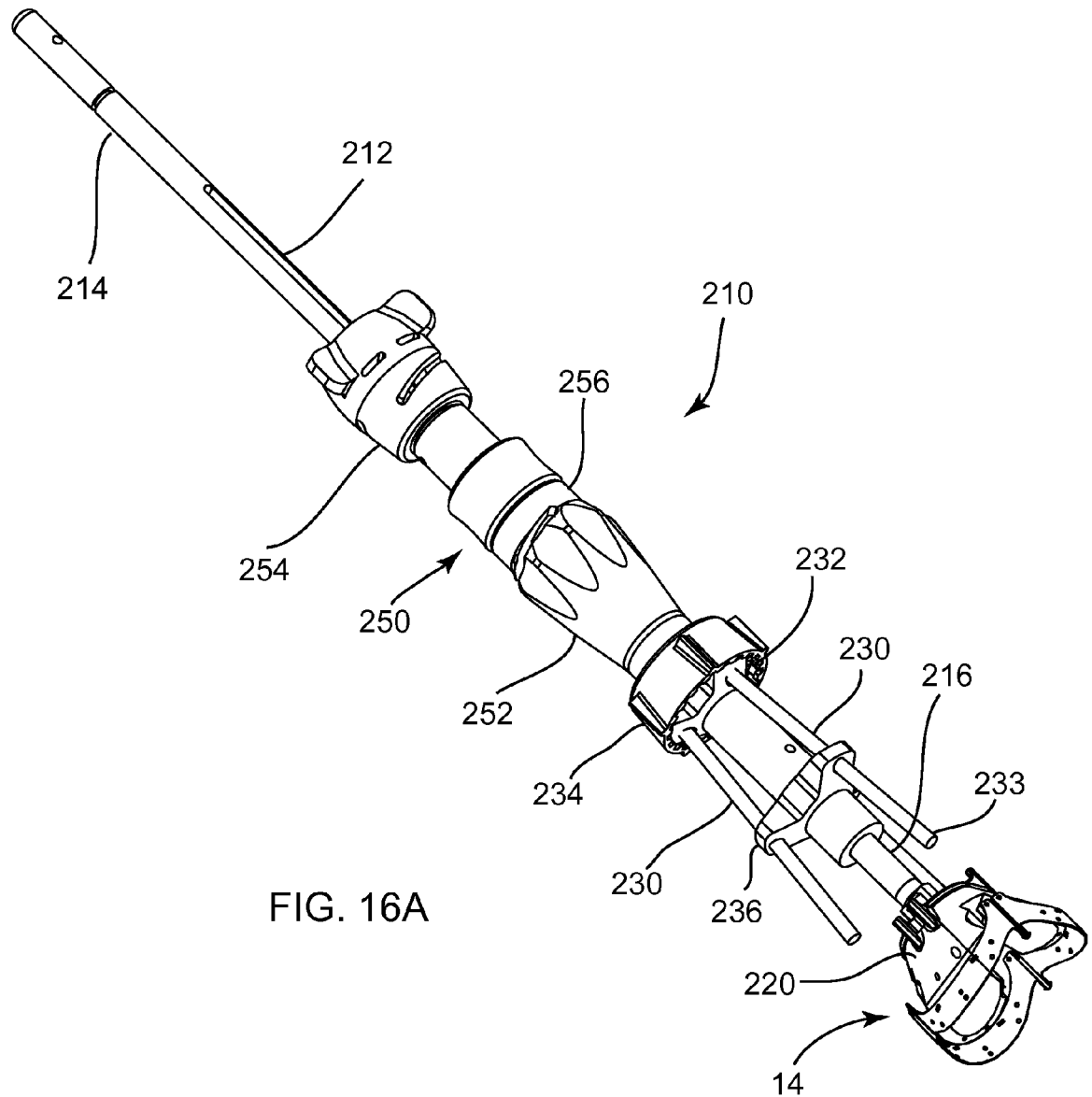
FIGS. 16A and 16B are perspective views of the valve holder tool of FIGS. 15A-15D, showing an actuator on the valve holder in distal and proximal positions, respectively.
Figure 16B:
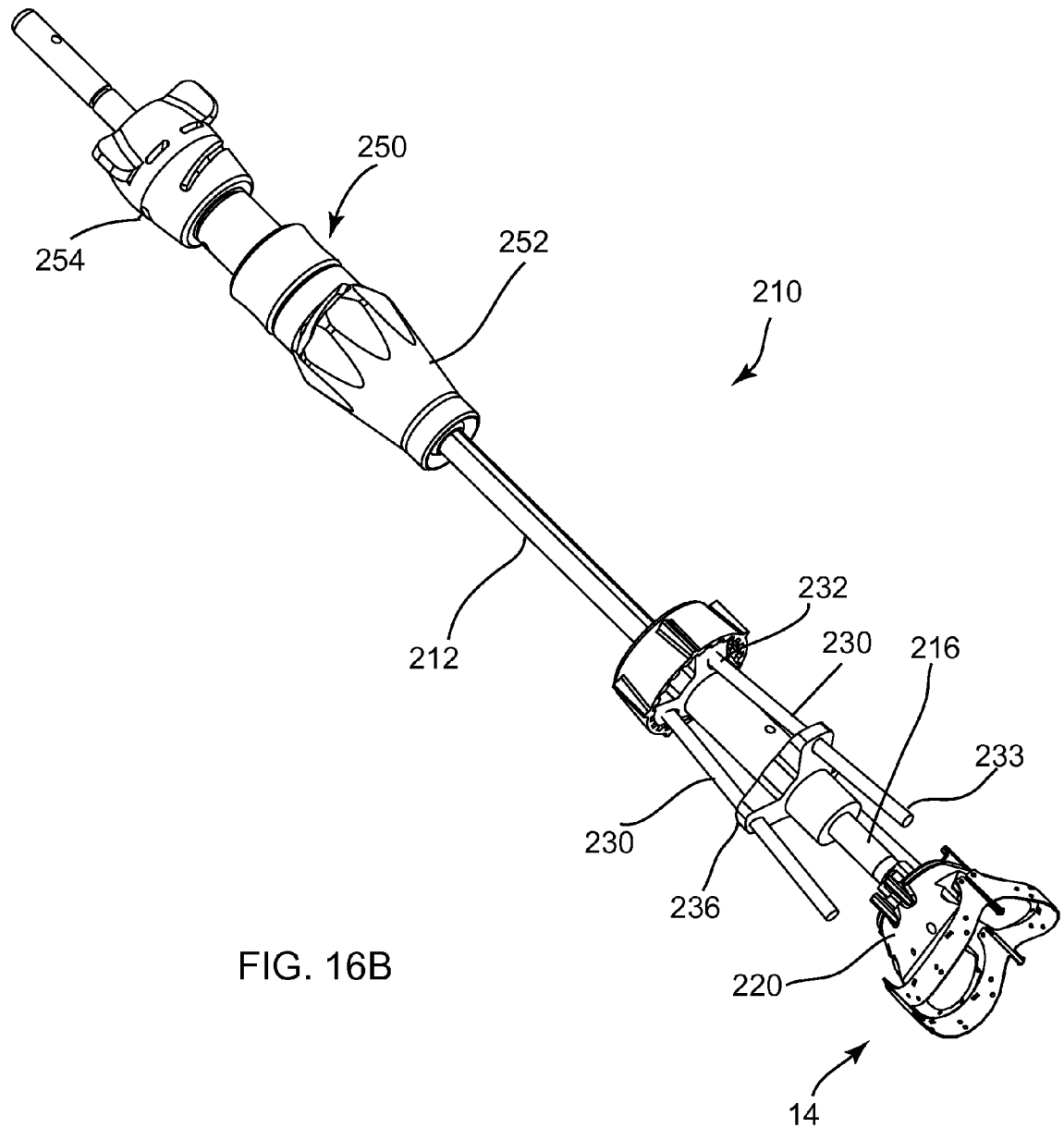

For example, as best seen in FIG. 15C, the actuator 250 may include an outer housing 252 and an inner member 256 disposed adjacent the hub 234 in the distal position. The inner member 256 may be coupled to a handle 254, e.g., such that axial movement of the handle causes the inner member to move axially. The outer housing 252 may be rotatable relative to the inner member 256, e.g., for capturing ends of the guide rails 150. The proximal ends 232 of the tubular members 230 may extend into the hub 234 and communicate with one or more recesses or other features, e.g., recess 253a between the outer housing 252 and the inner member 256. The outer housing 252 and/or inner member 256 may include one or more locking features, e.g., hooks, catches, ratchets, and the like, such as catch 253b within the recess 253a that may receive and/or engage the ends of the guide rails 150.

With the outer housing 252 open relative to the inner member, ends of the guide rails 150 may be received within the recess 253a, e.g., when the guide rails 150 are loaded through the tubular members 230. The outer housing 252 may then be rotated to engage the ends of the guide rails 150, e.g., with the catch(es) 253b and/or by at least partially closing the recess 253a to clamp the ends of the guide rails 150, thereby preventing the guide rails 150 from being separated from the actuator 250. Optionally, similar to the embodiment shown in FIGS. 23A and 23B, the ends of the guide rails 150 may include a slot 153 that may receive or otherwise engage corresponding hooks, catches, ratchets and the like (not shown) within the recess 253a or otherwise provided on the outer housing 252 and/or inner member 256.

During use, a portion of the guide rails 150 may be received in or otherwise engaged with the actuator 250, e.g., when the guide rails 150 are loaded through the tubular members 230. When the actuator 250 is moved from the distal position, shown in FIG. 16A, towards the proximal position, shown in FIG. 16B, e.g., by pulling the handle 254, the guide rails 150 may be pulled by the housing 252, thereby causing the guide rails 150 to separate at weakened regions or otherwise break, e.g. adjacent the distal ends 263 of the tubular members 230. Optionally, the actuator 250 may include a lock (not shown) to prevent proximal movement of the actuator 250 until the lock is released. For example, the actuator 250 may be rotated about the shaft 212 to engage or disengage a lock between the actuator 250 and the shaft 212.

This configuration of the valve holder tool 210 may allow the actuator 250 to be located at a distance proximally from the head 220. For example, this may facilitate actuation, allowing the user to actuate the valve holder 210 without having to reach into the biological annulus. In addition, this configuration of the valve holder tool 210 may also allow the actuator 250 to be moved a substantial distance away from the head 220 and the implantation site. For example, if the shaft 212 were replaced with a flexible catheter, and the guide rails 150 were sufficiently long and/or flexible, the valve holder 210 may be used in a percutaneous implantation or other procedure wherein the actuator is located outside the patient's body, while the head 220 (and valve 14 thereon) are located within the body at the implantation site, e.g., as disclosed in US 2007/0016288, incorporated by reference herein.

Figure 23A:
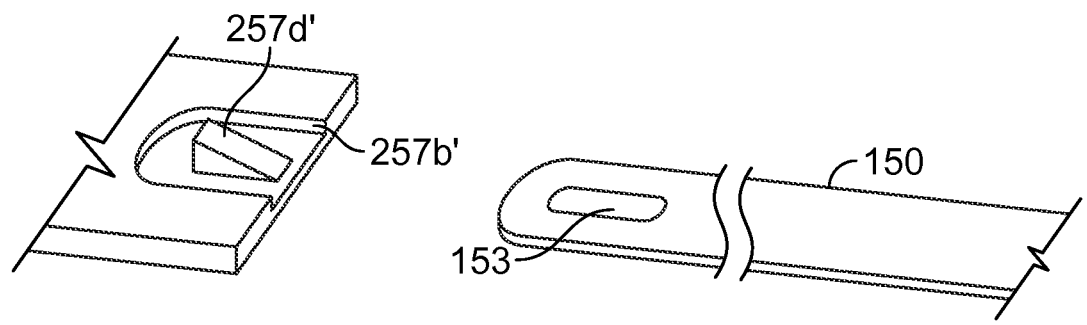
FIGS. 23A and 23B are details showing a free end of a guide rail being received within an actuator of the valve holder tool of FIGS. 22A and 22B.
Figure 23B:
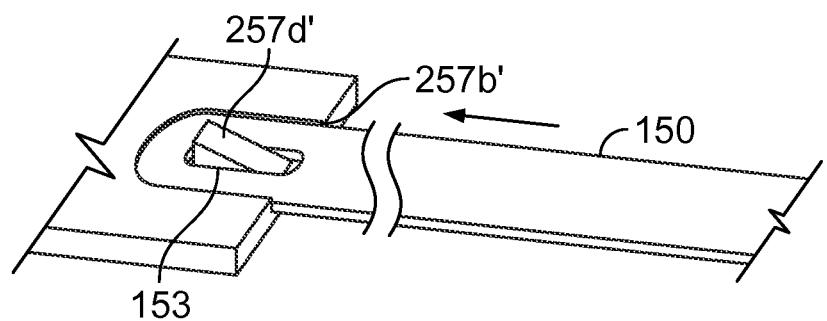

In another alternative, shown in FIGS. 22A and 22B, a valve holder tool 210' may include a set of cam-lock features 258 for securing ends of guide rails 150 (not shown, see FIGS. 23A and 23B) to an actuator 250.' The valve holder tool 210' includes an elongate shaft 212' including proximal and distal ends 214,' 216,' a support or head 220' on the distal end 216,' and a plurality of tubular members 230,' similar to the previous embodiments. An actuator 250' is slidable on the shaft 212,' e.g., for severing ends of guide rails 150, similar to the previous embodiment. The actuator 250 includes an inner member 256' including guide channels 257a' that communicate with tracks 257b.' Openings 257c' above respective tracks 257b' provide access into the tracks 257b,' if desired. Each track 257b' includes a tab, detent, catch, or other feature 257d' as best seen in FIGS. 23A and 23B that may be received in a hole 153 in an end of a guide rail 150.

Each cam-lock 258' includes a cap 258a' pivotally mounted to the actuator 250' by a hinge or element, such that the cap 258a' may be moved between an open position, e.g., extending away from the inner member 256' as shown, and a closed position covering a respective track 257b' and/or opening 257c'. In addition, each cam-lock 258' includes a tab 258b' or other feature that is received in the track 257b' when the cap 258a' is moved to the closed position. Thus, a guide rail 150 may be directed from a tubular member 230' along the guide channel 257a' into the track 257b,' e.g., until the catch 257c' is received in the hole 153, as shown in FIGS. 23A and 23B. The cap 258a' may then be closed, the tab 258b' contacting the guide rail to prevent the catch 257c' from being removed from the hole 153, thereby securing the end of the guide rail 150 to the actuator 250.' Optionally, the hole may be omitted from the guide rail 150 and the catch 257c' may have a pointed and/or barbed tip that may embed or penetrate through the end of the guide rail 150, e.g., when the cap 258a' is moved to the closed position. Once the guide rails 150 are captured in the tracks 257b' by the caps 258a', the actuator 250' may be subsequently moved proximally or otherwise manipulated to pull the guide rails, e.g., to break the guide rails at weakened regions or elsewhere, similar to the other embodiments described herein.

Turning to FIGS. 18A-19D, a method is shown for using the valve holder 210 of FIGS. 15A-17C to deliver a valve 14 into a biological annulus. The desired valve 14 (which may be any of the embodiments disclosed herein or in the references incorporated by reference herein) may be preloaded onto the head 220 of the valve holder 210 by the manufacturer or the user. Alternatively, a desired size valve (if multiple sizes are available) may be selected and loaded onto the head 220 by the user immediately before or during the procedure, e.g., using one or more sutures 13, as described above. For example, a valve sizer (or a series of progressively larger valve sizers) may be directed into the biological annulus to determine the appropriate size valve prosthesis to be delivered into the biological annulus.

Figure 18A:
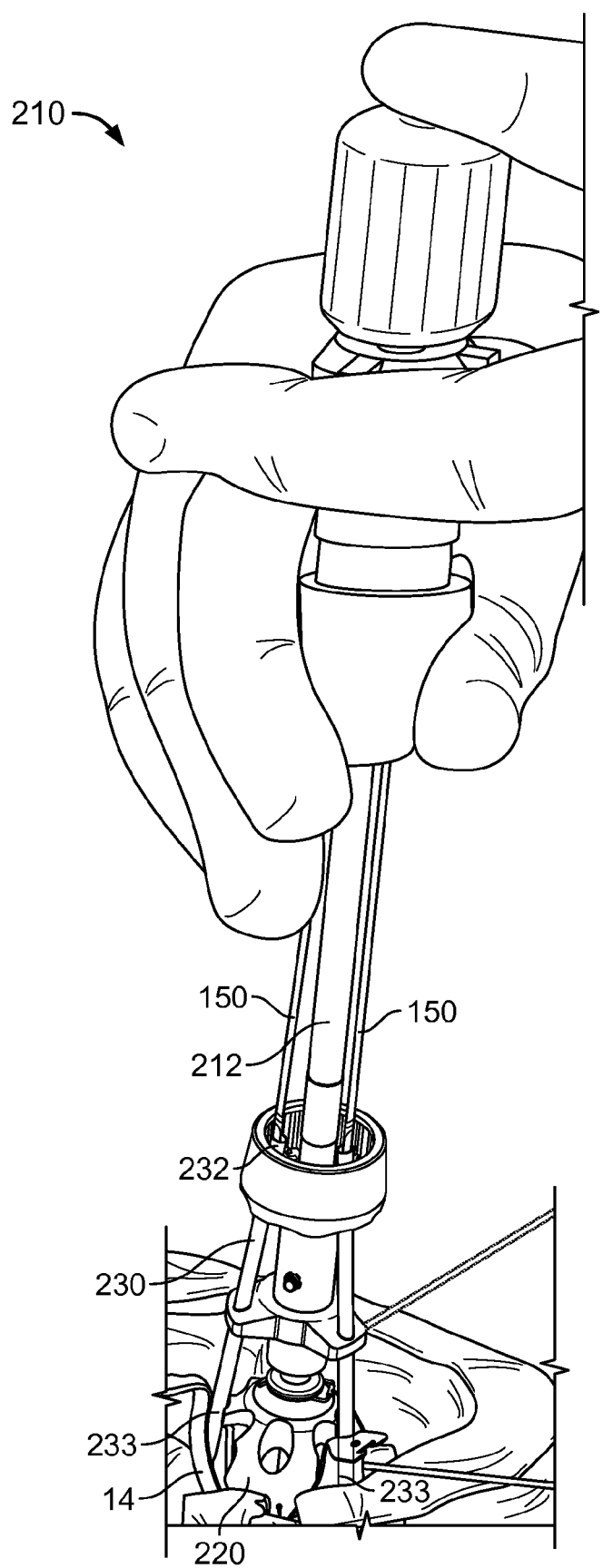
FIGS. 18A and 18B show the valve holder tool of FIG. 17A being used to deliver the valve prosthesis into a biological annulus along guide rails of a gasket member already delivered into the annulus.
Figure 18B:
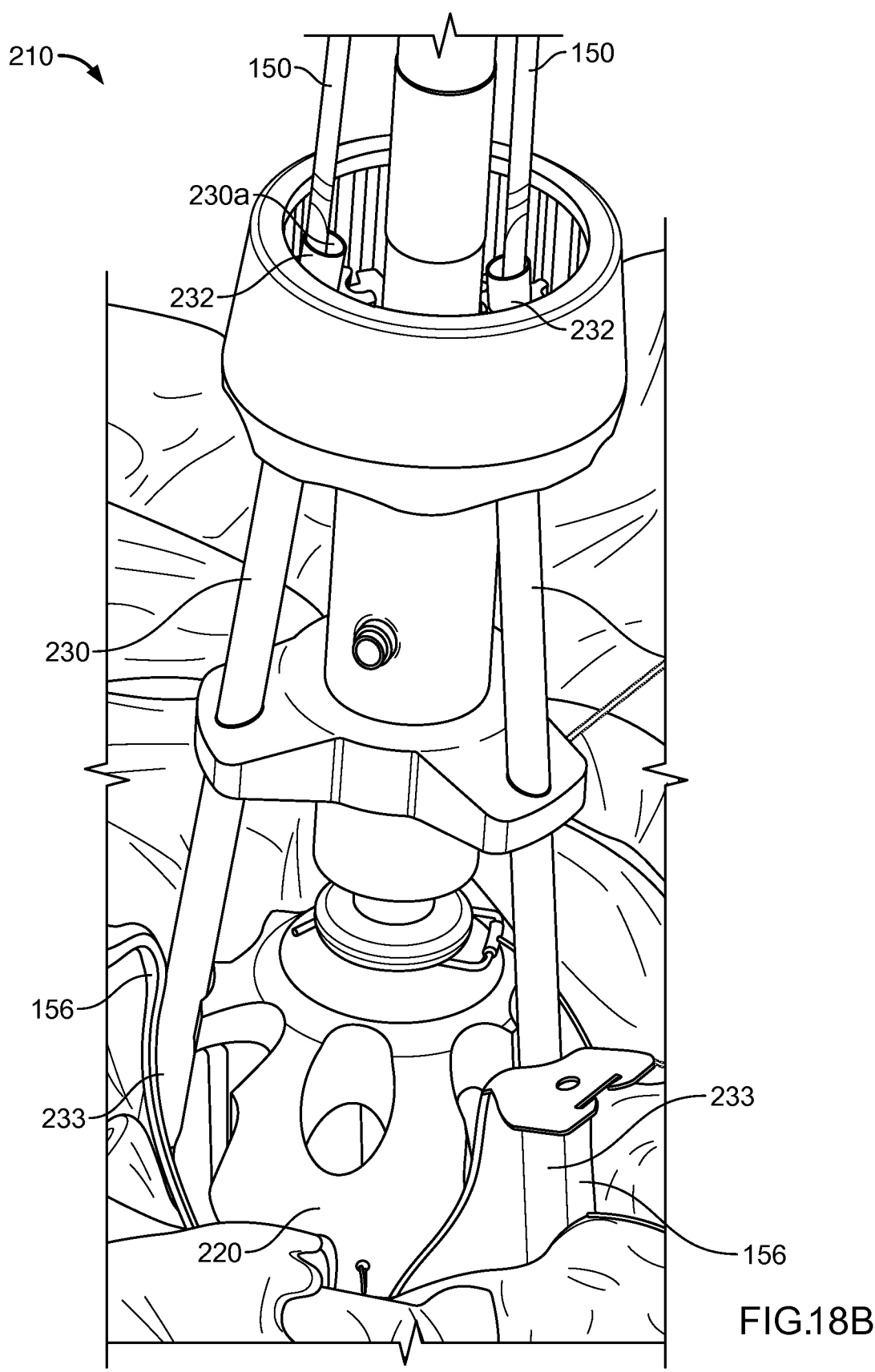

Before introducing the head 220 and valve 14 into the biological annulus, a gasket member (not shown) may be delivered and/or secured within the biological annulus, e.g., as described above. As can be seen in FIGS. 18A and 18B, guide rails 150 and guide shields 156 extend out of the biological annulus from the gasket member, which cannot be seen.

Turning to FIG. 18A, the head 220 of the valve holder 210, carrying the valve 14, may be directed into the biological annulus. Before doing so, the guide rails 150 may be loaded into the tubular members 230 of the valve holder 210. Each guide rail 150 may be loaded through a feature (not shown) of the valve 14 (e.g., as described elsewhere herein) and into the lower end 233 of the respective tubular member 230, e.g., until the guide rail 150 exits the upper end 232 of the tubular member 230.

Figure 20A:
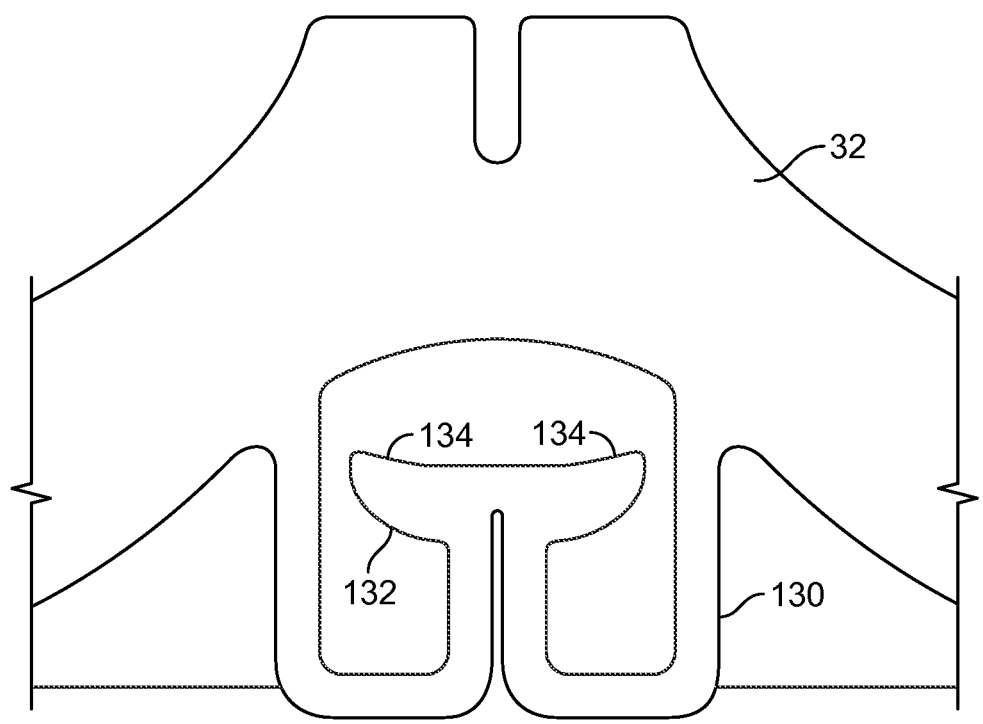
FIGS. 20A and 20B are details of a frame of a valve prosthesis that includes a receptacle including a cantilever spring, showing a track and locking elements being formed therein.
Figure 20B:
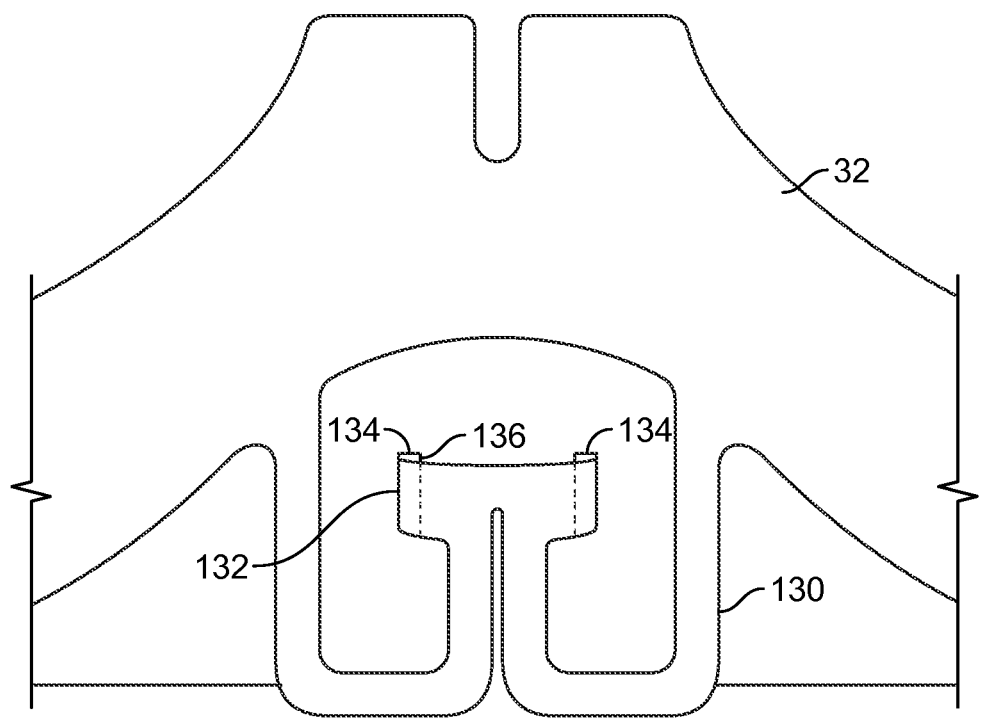

For example, as shown in FIGS. 20A-20E, the valve 14 may include a frame 32 including a plurality of receptacles or other features 130 configured to receive the guide rails 150 therethrough. Each receptacle 130 may include a cantilever spring 132 including a first end supported by the valve frame 32 and a second free end including one or more detents 134. As shown in FIGS. 20A and 20B, the detents 134 may be bent or otherwise formed to at least partially define a track, slot, or other passage 136 for receiving a guide rail 150 therethrough. The receptacle 130 may be formed integrally with the valve frame 32, e.g., laser cut or otherwise formed from a Nitinol or other sheet used to make the frame 32. Alternatively, other receptacles or connectors may be provided on the valve 14, such as those disclosed in the references incorporated by reference above.

Returning to FIGS. 18A and 18B, the receptacles 130 of the valve 14 may be aligned with the lower ends 233 of respective tubular members 230 on the valve holder 210. Thus, to insert the guide rails 150, the ends of the guide rails 150 may be passed upwards through the receptacles 130, into the lower ends 233 and out the upper ends 232 of the tubular members 230. Optionally, the valve 14 may include guides or other features (not shown) to facilitate loaded the ends of the guide rails 150 into the receptacles 130. For example, the fabric covering the valve 14 may include a slot or other opening that may receive the ends of the guide rails 150, and direct the guide rails 150 into the receptacles 130. In addition or alternatively, visual markers may be provided on the valve 14, e.g., above or around the receptacles 130, to facilitate inserting the guide rails 150 through the valve 14 and into tubular members 230.

Turning to FIG. 18B, as the head 220 and valve 14 are directed into the biological annulus, the valve 14 may slidably contact the guide shields 156 extending from the gasket member (not shown). The guide shields 156 may thereby provide a substantially smooth and/or lubricious surface, which may facilitate advancing the valve 14 into a narrow or partially obstructed biological annulus.

Figure 18C:
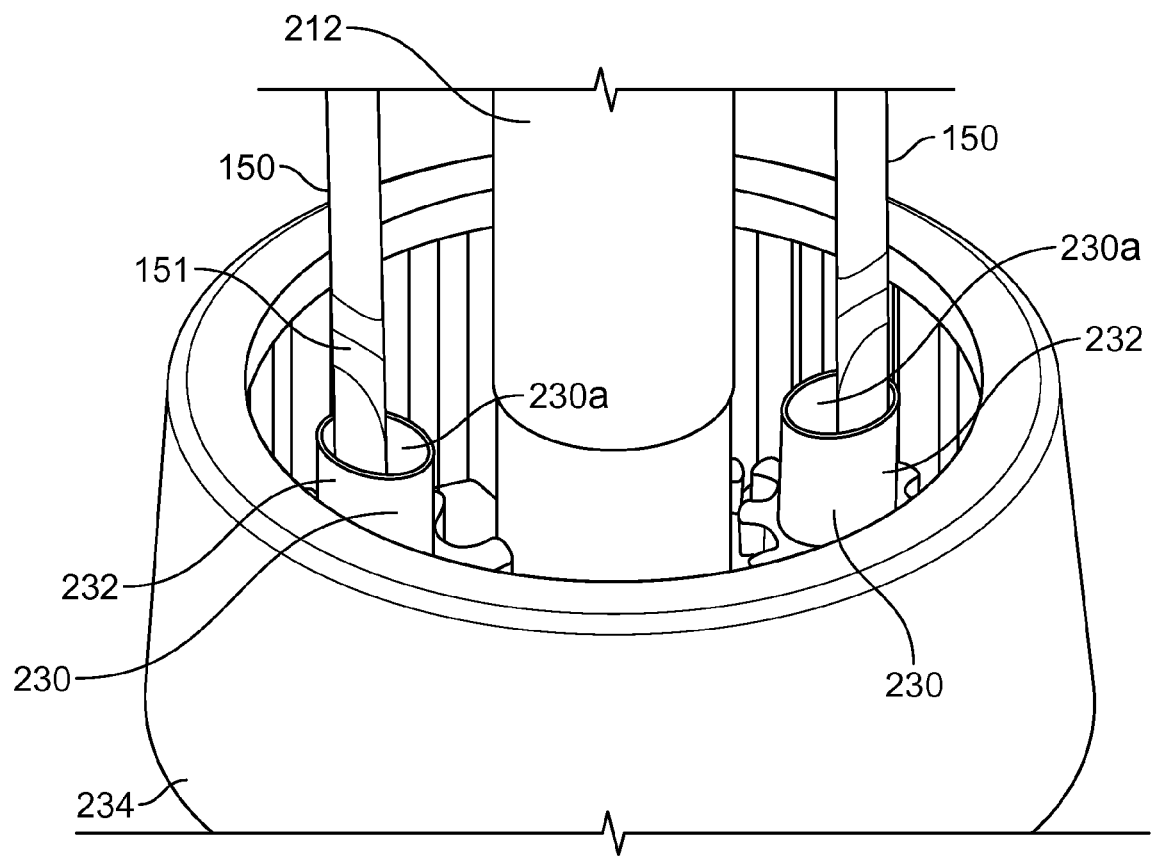
FIG. 18C is a detail showing the passages on the valve holder tool of FIG. 17C with guide rails from a gasket member extending through the passages.

As shown in FIG. 18C, the guide rails 150 may include markers 151 at predetermined locations, i.e., known lengths from the gasket member. The markers 151 may exit the upper ends 232 of the tubular members 230 when the valve 14 is located immediately adjacent the gasket member. This may provide the user confirmation of the relative location and that the valve 14 may then be secured to the gasket member.

Figure 20C:
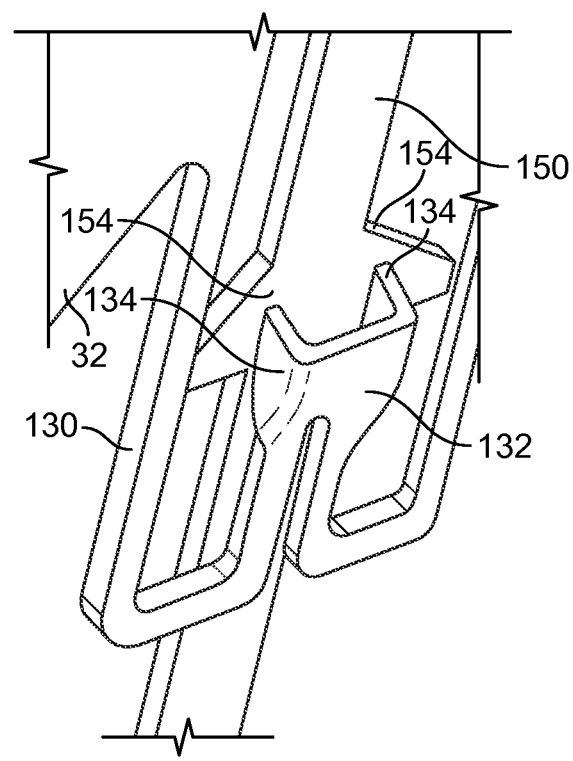
FIGS. 20C and 20D are perspective and side details, respectively, of the receptacle of FIGS. 20A and 20B receiving a guide rail therethrough, the locking elements on the cantilever spring causing the cantilever spring to defect outwardly to accommodate locking tabs on the guide rail passing through the receptacle.
Figure 20D:
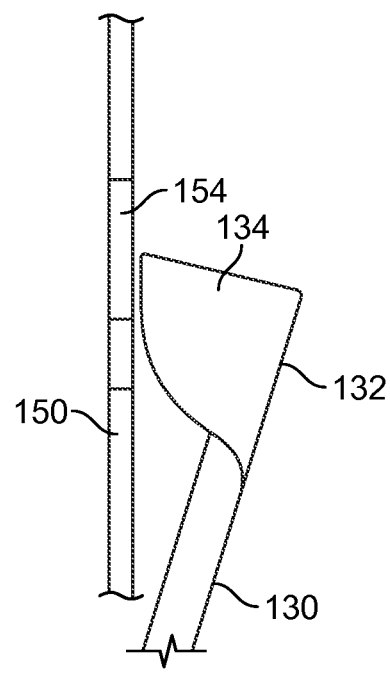
Figure 20E:
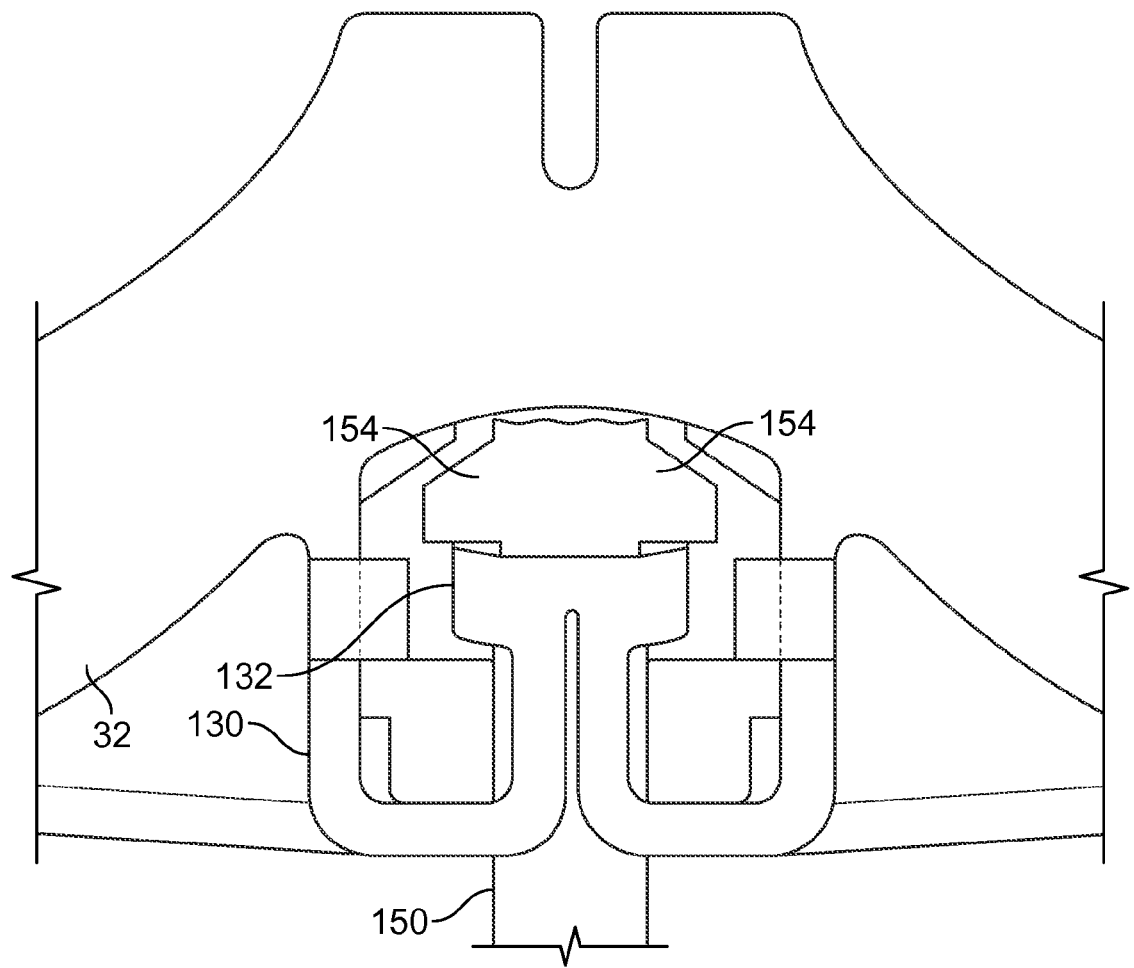
FIG. 20E is a side detail of the frame of FIGS. 20A-20D with the locking tabs of a guide rails engaged with the locking elements of the receptacle and a top portion of the guide rails severed and removed.
Figure 21A:
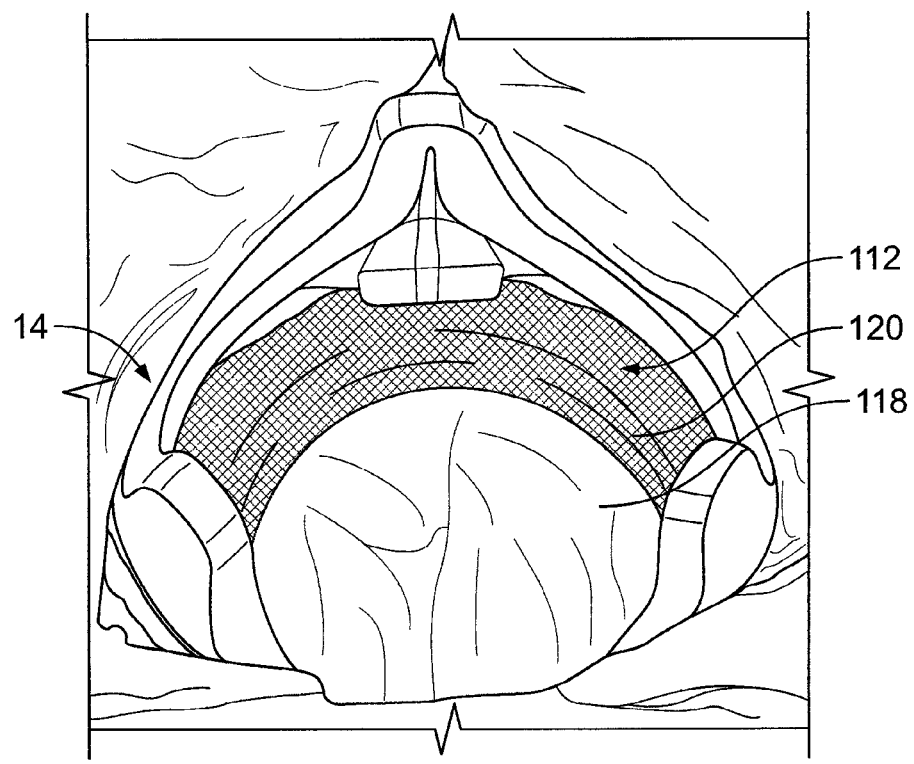
FIGS. 21A-21D are perspective views of a biological annulus with a valve assembly including a gasket member and a valve prosthesis (with leaflets omitted for clarity) implanted therein.
Figure 21B:
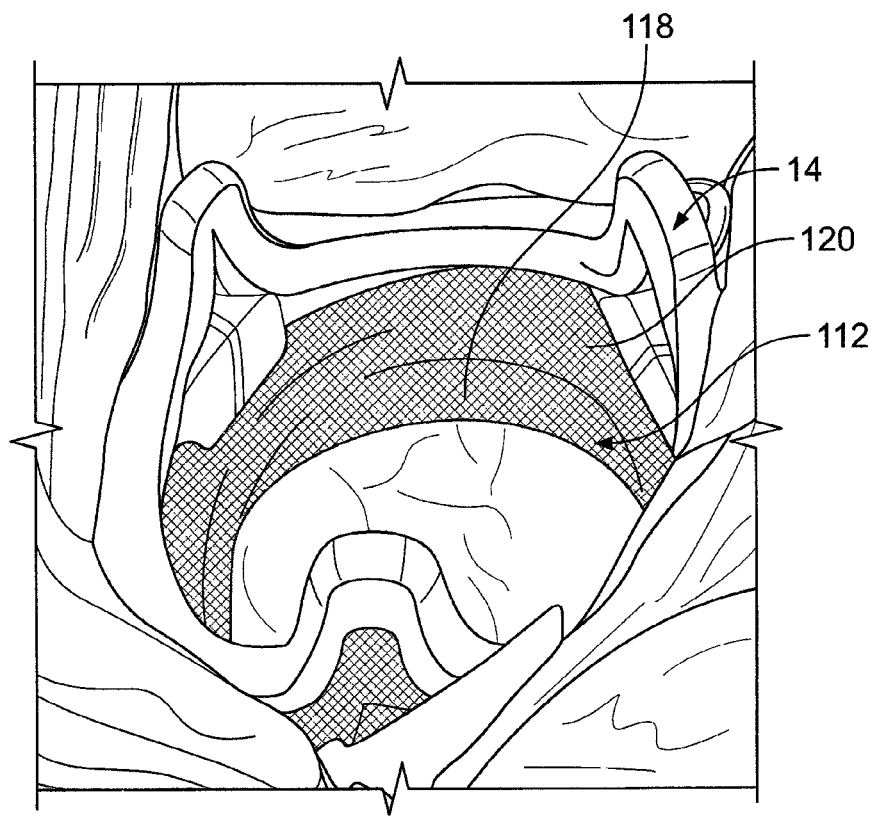
Figure 21C:
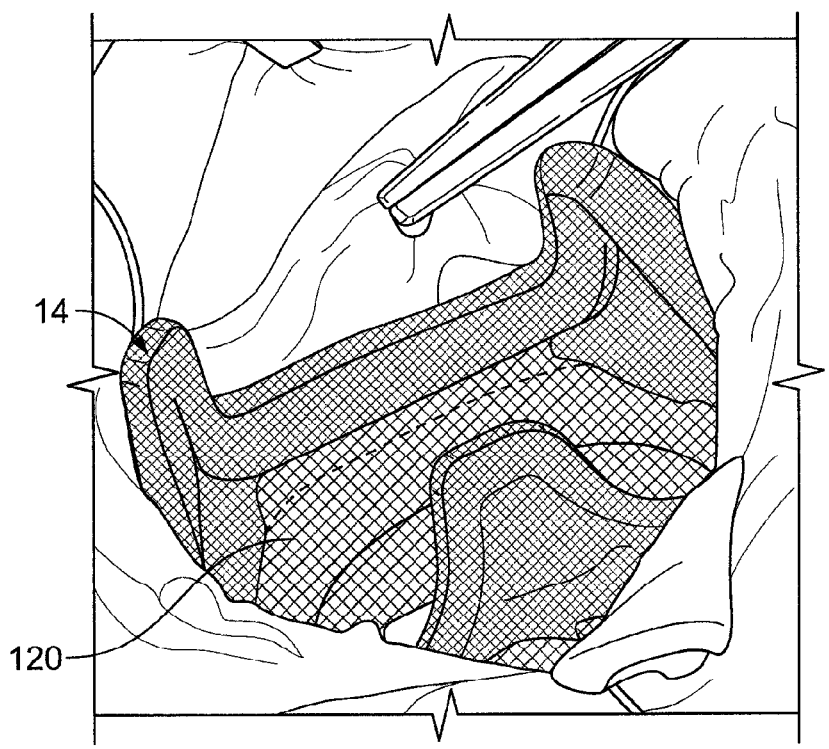
Figure 21D:
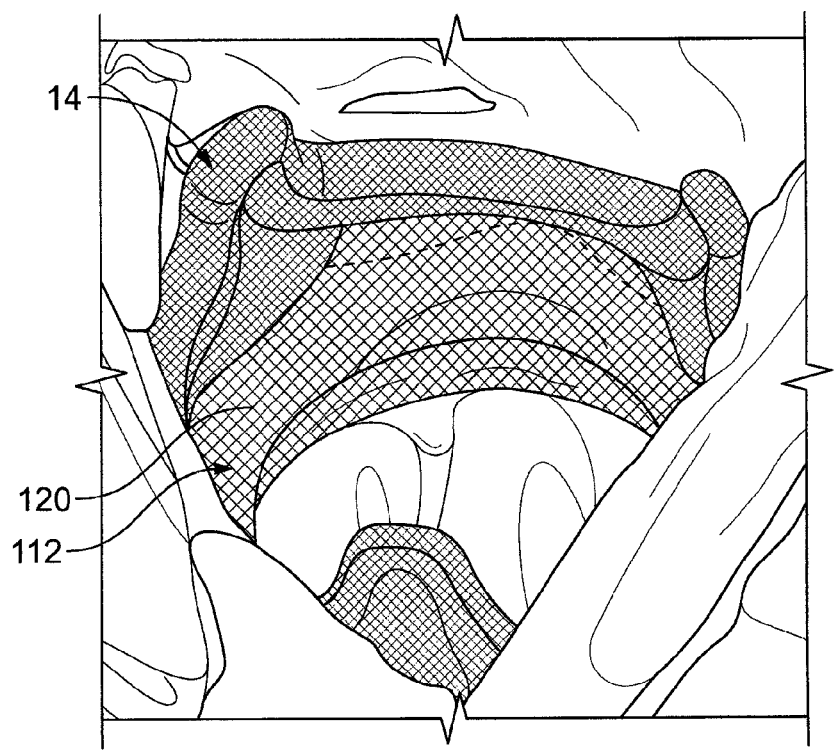

For example, turning to FIGS. 20C-20E, when the valve 14 is disposed immediately adjacent the gasket member, the retention elements 154 on the guide rails 150 may encounter the detents 134 on the cantilever spring 132. As shown, the retention elements 154 may include tapered upper edges and the detents 134 may include tapered lower edges. Thus, as the valve 14 is directed downwardly, the tapered edges may slide relative to one another, causing the cantilever spring 132 to deflect resiliently outward, as shown in FIG. 20D. Once the detents 134 pass below the retention elements 154, the cantilever spring 132 may return inwardly, thereby capturing the detents 134 below the locking tabs 154. The detents 134 may include substantially blunt upper edges and the retention elements 154 may include substantially blunt lower edges, thereby preventing the valve 14 from being moved subsequently away from the gasket member, similar to the embodiment disclosed in the references incorporated by reference above.

Turning to FIG. 20E, the guide rails 150 may include a weakened region above the locking tabs 154 or may be otherwise severable above the locking tabs 154. For example, the guide rails 150 may include one or more holes, thinned regions, and the like (not shown), which may allow the guide rails 150 to preferential break at the weakened regions, similar to other embodiments described elsewhere herein.

With additional reference to FIGS. 18B and 18C, once the markers 151 on the guide rails 150 appear from the upper ends 232 of the tubular members 230, the valve holder 210, and valve 14, may be advanced further distally to secure the valve 14 to the gasket member. As just described with reference to FIGS. 20A-20E, the valve 14 may be advanced to engage the detents 134 with the retention element 154. To facilitate this, the user may pull or otherwise subject the guide rails 150 to proximal tension, while advancing the valve holder 210 and valve 14 until a "click" or other audible and/or tactile feedback is provided that confirms that the detents 134 and retention elements 154 are engaged. Each set of detents 134 and retention elements 154 may be engaged sequentially or simultaneously.

Optionally, the valve holder tool may include one or more safety features that prevent final engagement of the valve 14 with the gasket member until the user makes an affirmative decision to complete this step. For example, as shown in FIGS. 22A and 22B, the valve holder tool 210' includes a handle 270' and cap 274' that may facilitate manipulation of the valve holder tool 270' during a procedure. The cap 274' may be disposed above a hub 272' coupled to the shaft 212' such that the cap 274' may be movable towards the hub 272' to complete deployment of the valve 14 (not shown). However, features 276' on the cap 274' may be keyed with an opening (not shown) through the hub 272' such that the user must rotate the cap 274' to align the features 276' with the opening before the cap 274' may be directed towards the hub 272.' In addition, the shaft 213' may include an axial marker or other visual feature that may be used to confirm the orientation of the head 220' and valve 14 relative to surrounding anatomy.

After securing the valve 14 to the gasket member, the guide rails 150 may then be severed or otherwise separated from the gasket member, e.g., above the retention elements 154, as shown in FIG. 20E. Methods for breaking or otherwise severing the retention elements 154 are described above. For example, in one embodiment, each tubular member 230 may be rotated to twist the guide rail 150 received therein until the guide rail 150 breaks at the weakened region. Alternatively, the hub 234 may be twisted to break the guide rails 150, e.g., substantially simultaneously. In a further alternative, shown in FIGS. 16A and 16B, the actuator 250 engaging the ends of the guide rails 150 may be pulled proximally, thereby breaking the guide rails 150 at their respective weakened regions. In a further alternative, the guide rails 150 may be cut or otherwise severed using a tool introduced into the biological annulus.

Figure 19A:
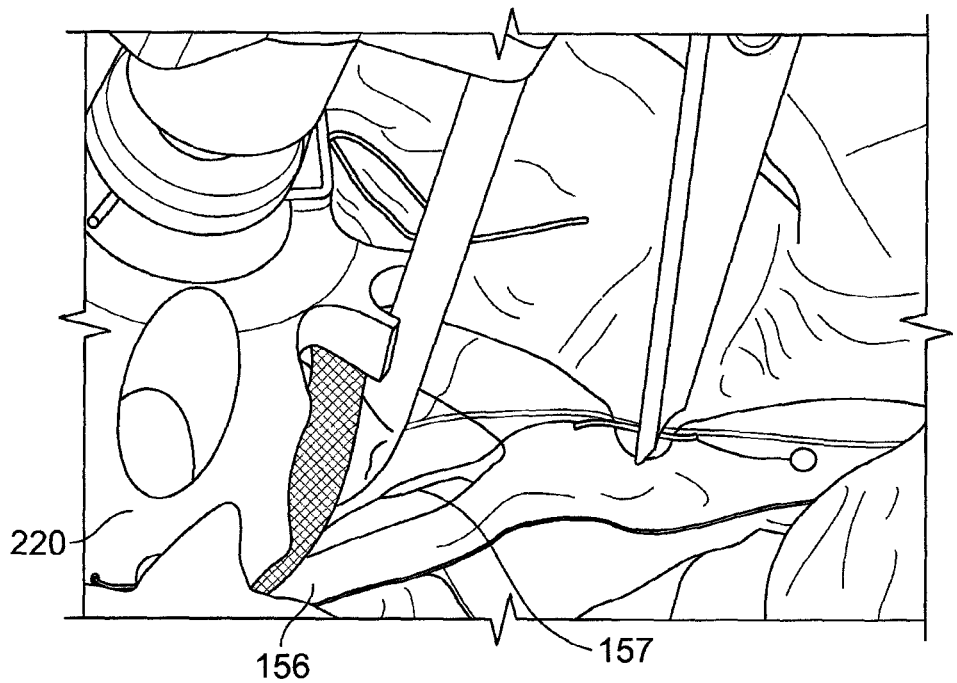
FIG. 19A is a detail showing a method for removing guide shields from a gasket member after a valve prosthesis has been engaged with the gasket member.

Turning to FIG. 19A, the guide shields 156 may be removed from the gasket member 112 before or after severing the guide rails 150. As shown, sutures 157 may be looped through individual portions of the sewing cuff (not shown) and guide shields 156 that may be cut or otherwise severed. The sutures 157 may then simply unravel or otherwise loosen, allowing the guide shields 156 and sutures 157 to be removed from the gasket member. Additional information on methods for attaching and removing the guide shields may be found in the references incorporated by reference above.

Figure 19B:
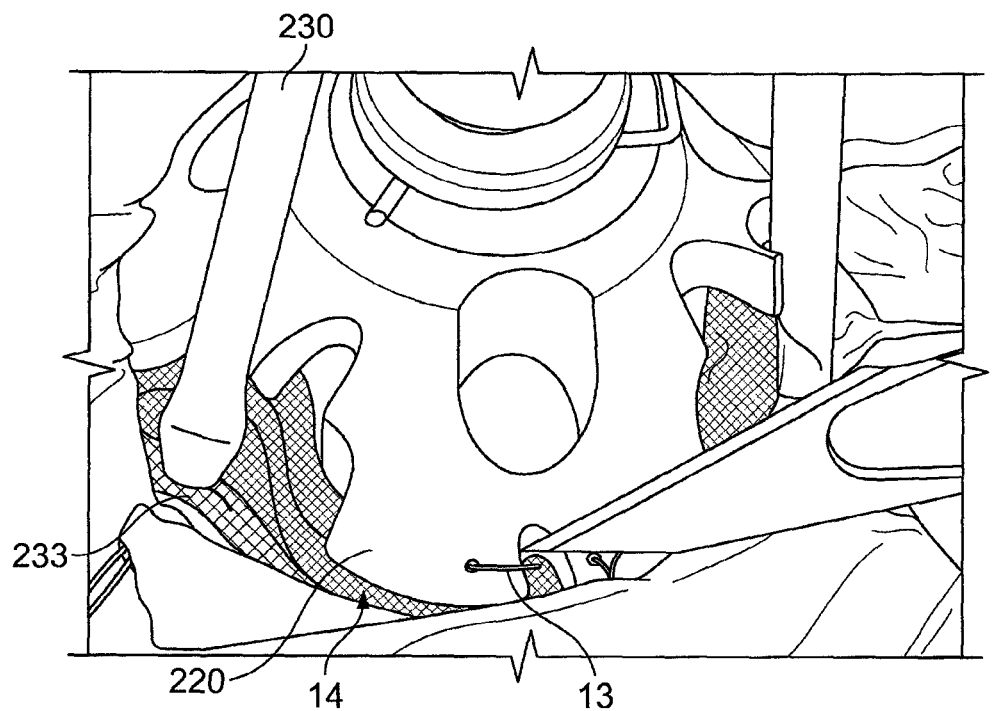
FIG. 19B is a detail showing a method for removing a valve prosthesis from the valve holder tool of FIGS. 17A and 17B by cutting the sutures securing the valve prosthesis to the valve holder tool.
Figure 19C:
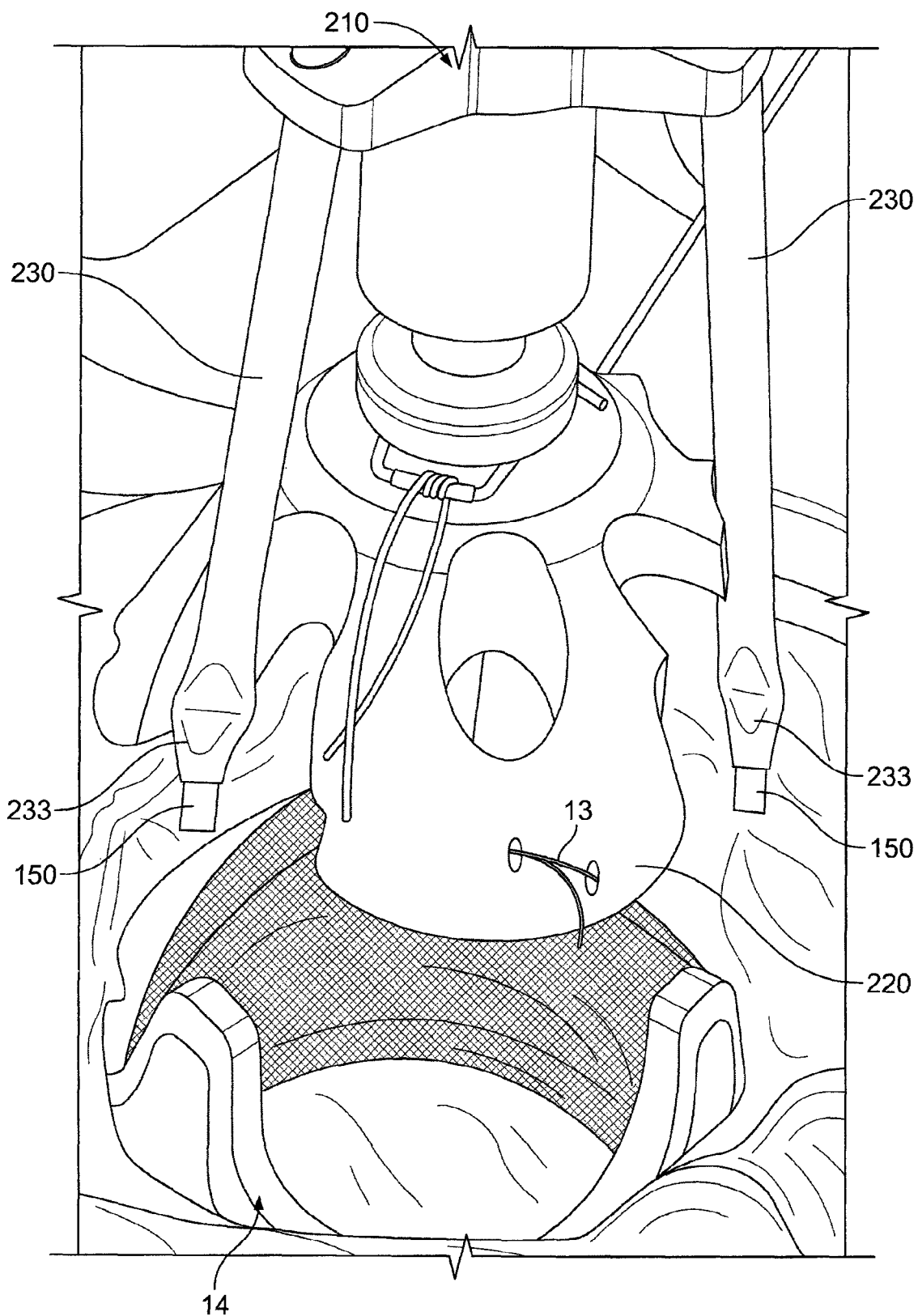
FIGS. 19C and 19D show a distal end of the valve holder tool of FIG. 19B being withdrawn after releasing the valve prosthesis from the valve holder tool.
Figure 19D:
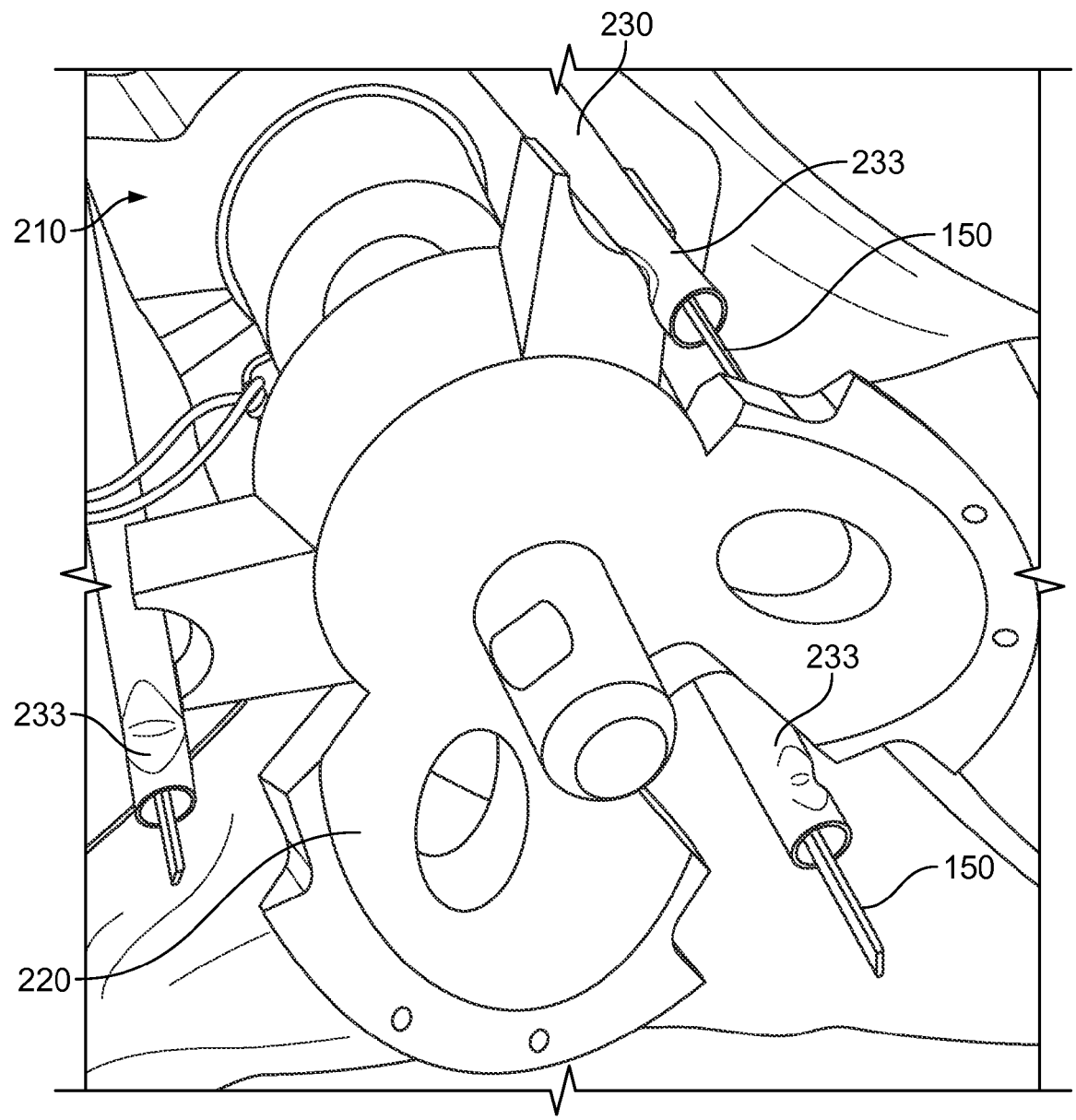

Turning to FIG. 19B, the valve 14 may be released from the valve holder 210, e.g., before or after severing the guide rails 150 and/or removing the guide shields 156. As shown, sutures 13 may be cut, thereby releasing the valve 14 from the head 220, and allowing the head 220, valve holder 210, and sutures 13 to be removed. FIGS. 19C and 19D show the valve holder 210 being separated from the valve 14. As best seen in FIG. 19D, the severed ends of the guide rails 150 may extend from the lower ends 233 of the tubular members 232 when the valve holder 210 is removed, thereby ensuring that the guide rails 150 are removed from the patient. In addition or alternatively, the sutures 13 may be anchored to a portion of the head 220 or valve holder 210, e.g., when the valve 14 is secured to the head 220. Thus, when the sutures 13 are cut to allow the valve 14 to be separated from the head 220, the sutures 13 may be remain anchored to the valve holder 210 to avoid having to retrieve individual pieces of the sutures 13.

FIGS. 21A-21D show various views of the implanted valve 14 and gasket member 12 with the leaflets of the valve 14 omitted for clarity.

Turning to FIGS. 24A-26, another exemplary embodiment of a valve member 314 is shown that generally includes an annular shaped body or frame 332, a plurality of receptacles 380 attached to the frame 332, and one or more valve elements (not shown for simplicity). The valve member 14 may include a fabric covering (also not shown) covering the frame 332, receptacles 380, and/or other components of the valve member 14. The valve member 314 may be included in any of the systems and methods described herein and/or in the references incorporated by reference herein.

Figure 25A:
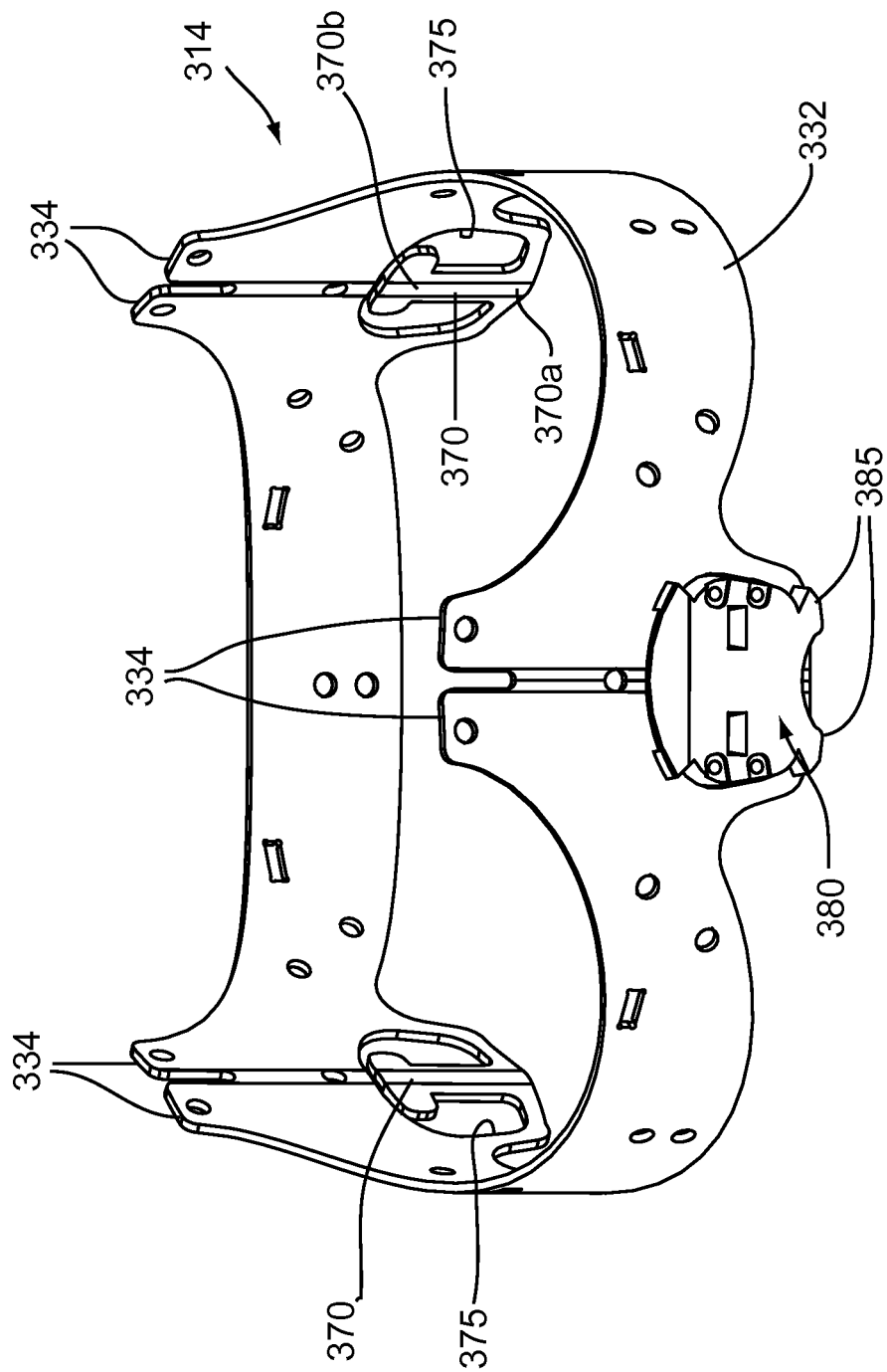
FIGS. 25A and 25B are perspective views of a frame for a valve prosthesis including the receptacle of FIGS. 24A and 24B attached thereto.
Figure 25B:
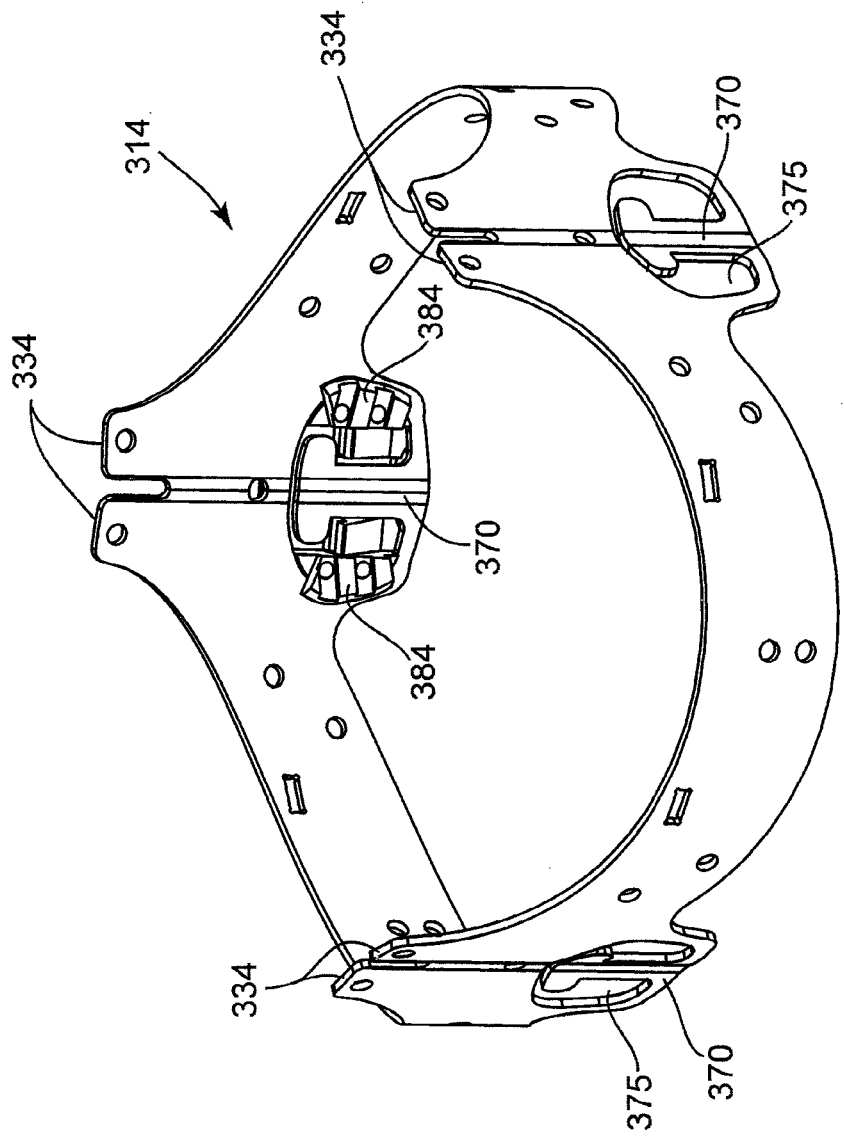

As shown in FIGS. 25A and 25B, the frame 332 is an annular band including commissures 334, e.g., at the cusps, and spring tabs 370, e.g., at the lobes, similar to other embodiments described herein. The spring tabs 370 may be supported by extensions of the frame 332 defining windows 375, e.g., receiving the receptacles 380, as described further below. As shown, each spring tab 370 includes a lower end 370a substantially fixed relative to the frame 332 and a free upper end 370b, e.g., having a "T" shape. Thus, the free end 370b of the spring tabs 370 may be deflectable radially inwardly, but may be resiliently biased to return to the position shown in FIGS. 25A and 25B.

Figure 24A:
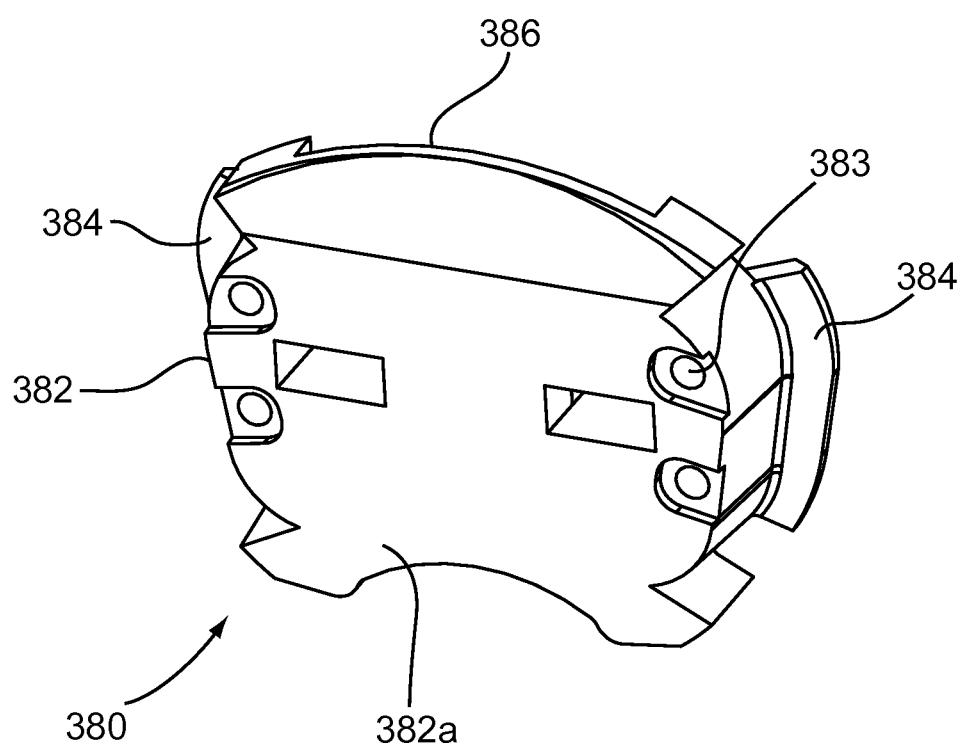
FIGS. 24A and 24B are front and back views, respectively, of a receptacle that may be attached to a valve prosthesis.
Figure 24B:
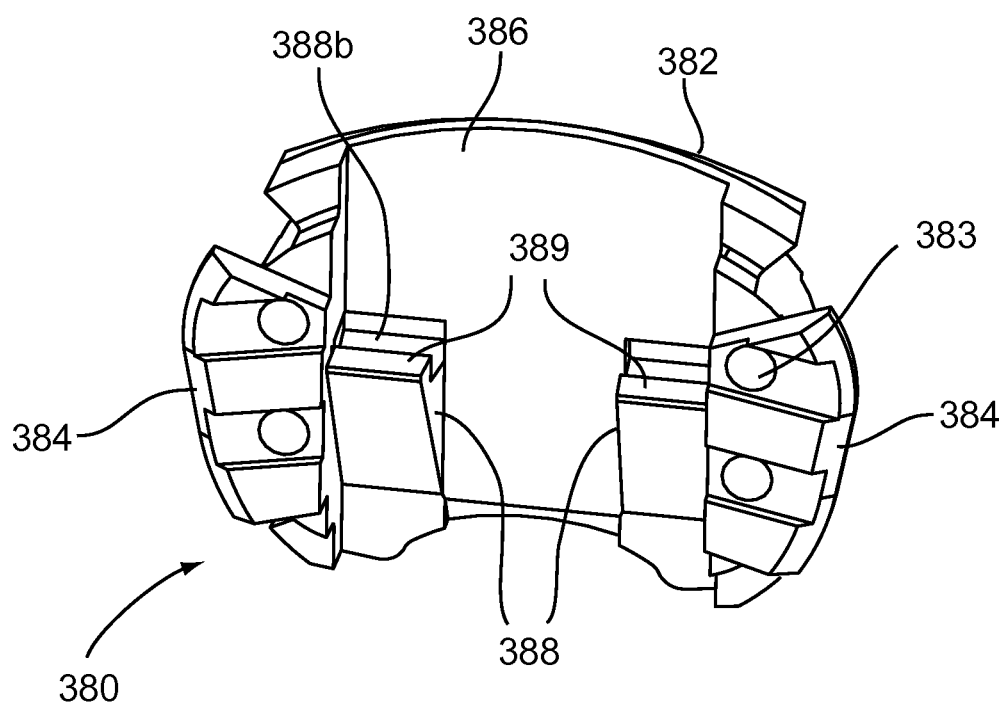

Turning to FIGS. 24A and 24B, the receptacle 380 may be a unitary body, e.g., injection molded, cast, machined, or otherwise formed from plastic, metal, or composite material. Generally, the receptacle 380 includes a main body 382 defining a substantially smooth front surface 382a, as shown in FIG. 24A, and include a plurality of lips or flanges 384, 385 extending from the main body 382. For example, a first set of flanges 384 may extend laterally from the main body 382 but offset away from the front surface 382, and a second set of flanges 385 may extend up and down from the main body 382. Thus, the first set of flanges 384 may be offset from the second set of flanges 385, e.g., for capturing a portion of the frame 332 therebetween, as described further below.

The receptacle 380 includes a channel 386 along a back surface of the main body 382 and a pair of locking tabs 388 within the channel 386, as shown in FIG. 24B. The channel 386 may have sufficient width to receive a guide rail 150 (see FIG. 26) therethrough, e.g., between the tabs 388. The locking tabs 388 may include ramped or tapered lower surfaces 388a and blunt upper surfaces 388b. Optionally, as shown, raised ridges or lips 389 may be provided that extends upwardly from the upper surfaces 388b, thereby defining pocket behind the lips 389 and above the upper surfaces 388b.

The receptacle 380 may include one or more additional features formed therein, e.g., holes 383 for receiving sutures 390 or other fasteners therethrough.

Turning to FIGS. 25A and 25B, a receptacle 380 may be attached to the frame 332 over each of the spring tabs 370, e.g., such that the receptacle 380 is disposed on an outer surface of the frame 332. For example, the main body 382 of each receptacle 380 may be compressed to direct the first set of flanges 384 closer together and the receptacle 380 may be inserted through the window 375 around one of the spring tabs 370. As the main body 382 is inserted through the window 375, the second set of flanges 385 may abut the outer surface of the frame 332 while the first set of flanges 384 pass through behind the frame 332. The main body 382 may then be released, thereby capturing the frame 332 between the first and second set of flanges 384, 385. Optionally, sutures 390 may be directed through holes 383 in the receptacles 380 and around the portion of the frame 332 defining the windows 375, thereby further securing the receptacles 380 to the frame 332.

The frame 332 may then be covered with fabric, e.g., over the receptacles 380, using similar procedures for assembling valves described elsewhere herein and in the references incorporated by reference herein. Slits or other openings (not shown) may be formed in the fabric covering above and below the receptacles 380, e.g., to provide access to the receptacles 380 during use.

With the receptacles 380 attached to the frame 332, the channel 386 may be spaced apart from the frame 332, thereby defining a vertical passage between the receptacles 380 and the frame 332, similar to other embodiments described herein.

Figure 26:
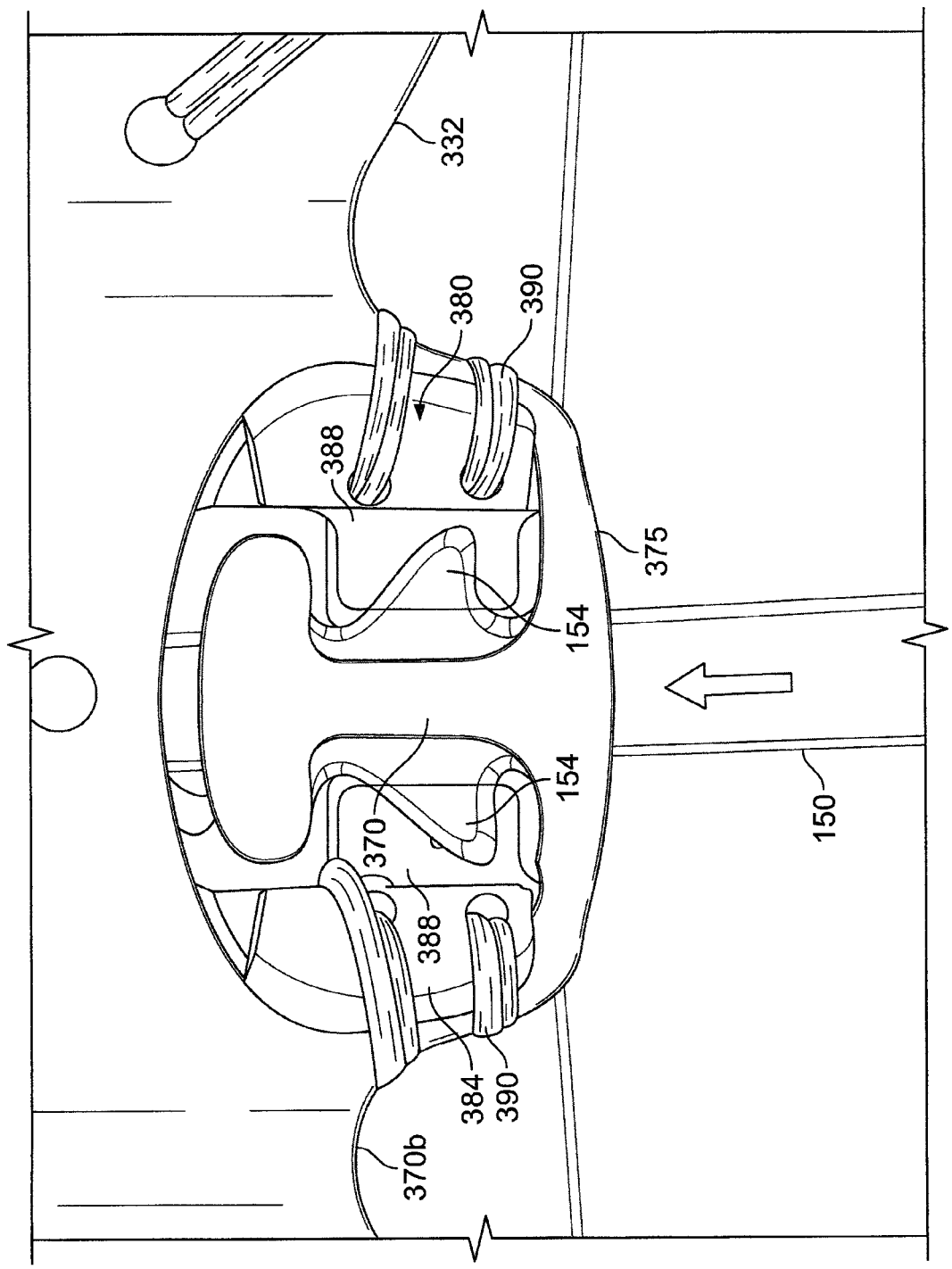
FIG. 26 is a detail showing a guide rail being received within the receptacle of FIGS. 25A and 25B.

Turning to FIG. 26, during use, a guide rail 150 may be passed through the passage, i.e., between the receptacle 380 and frame 332, e.g., from below. The free of the guide rail 150 may pass freely through the channel 386 of the receptacle 380, e.g., exiting out the top of the receptacle 380 and frame 332. As retention elements 154 on the guide rails 150 enter the channel 386, the retention elements 154 may slide along the ramped lower surfaces 388a of the locking tabs 388, thereby directing the spring tab 370 away from the channel 386 to accommodate the retention elements 154 passing over the locking tabs 388. Once the retention elements 154 pass over the locking tabs 388, the spring tab 370 may resiliently return inwardly, thereby directing the retention elements 154 into the pockets defined by the lips 389 and upper surfaces 388b of the locking tabs 388. Thus, if the guide rail 150 is pulled back down out of the receptacle 380, the blunt lower edges of the retention elements 154 may engage the upper surfaces 388b, thereby preventing removal of the guide rail 150. The free end of the guide rail 150 above the receptacle 380 may be severed, similar to previous embodiments, e.g., including one or more weakened regions (not shown) above the retention elements 154.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for implanting a heart valve assembly in a biological annulus, the method comprising:

inserting a first prosthesis into the biological annulus with the first prosthesis in a contracted condition, the first prosthesis comprising a plurality of elongate leaders extending therefrom and secured to a delivery tool;

deploying the first prosthesis in the biological annulus such that the first prosthesis expands to an enlarged condition within the biological annulus;

securing the first prosthesis to tissue surrounding the biological annulus;

severing the leaders from the delivery tool;

advancing a second valve prosthesis along free ends of the leaders, which pass through respective portions of the second valve prosthesis; and engaging the second valve prosthesis with the secured first prosthesis.

2. The method of claim 1, wherein the first prosthesis is secured to tissue by directing a plurality of fasteners through a sewing cuff of the first prosthesis.

3. The method of claim 1, further comprising securing the second prosthesis to the first prosthesis.

4. The method of claim 3, wherein the second prosthesis is secured to the first prosthesis by retention elements on the leaders.

5. The method of claim 1, wherein tissue surrounding the biological annulus is dilated when the first prosthesis is deployed.

6. A method for implanting a heart valve assembly in a biological annulus, the method comprising:

constraining a first annular prosthesis in a contracted condition, the first prosthesis comprising a plurality of elongate leaders extending therefrom and secured to a delivery tool;

introducing the first prosthesis into the biological annulus in the contracted condition;

deploying the first prosthesis within the biological annulus such that first prosthesis expands towards an enlarged condition;

severing the leaders from the delivery tool;

introducing a second prosthesis along free ends of the leaders, which pass through respective portions of a second valve prosthesis, and advancing the second prosthesis towards the first prosthesis into the biological annulus; and securing the second prosthesis to the deployed first prosthesis.

7. The method of claim 6, wherein the second prosthesis is secured to the first prosthesis by advancing one or more knots down the leaders after the second prosthesis is introduced into the biological annulus.

8. A method for implanting a heart valve assembly in a biological annulus, the method comprising:

introducing a first prosthesis into a biological annulus, the first prosthesis comprising a plurality of elongate leaders extending therefrom and secured to a delivery tool;

severing the leaders from the delivery tool;

passing free ends of the leaders through respective portions of a second prosthesis; and directing the second prosthesis towards the introduced first prosthesis until portions of second prosthesis pass over connectors on the leaders.

9. The method of claim 8, wherein the first prosthesis comprises an annular member and a sewing cuff extending outwardly from the annular member, and wherein the second prosthesis sealingly engages the sewing cuff upon passing over the connectors on the leaders.

10. The method of claim 8, wherein the connectors comprise a tapered arrow shape allowing the second prosthesis to pass freely over the connectors towards the first prosthesis but substantially prevent subsequent proximal movement of the second prosthesis away from the first prosthesis.

11. The method of claim 8, further comprising severing the leaders above the connectors after the second prosthesis has passed over the connectors.

12. The method of claim 11, wherein the leaders comprise weakened regions above the connectors, and wherein the leaders are severed by subjecting the leaders to tension sufficient to break the weakened regions.

13. The method of claim 8, further comprising introducing free ends of the leaders through introducers on the second prosthesis before directing the second prosthesis over the leaders.

14. The method of claim 13, further comprising removing the introducers from the second prosthesis.

15. The method of claim 14, wherein the introducers comprise tubular members received through fabric of the second prosthesis.

16. The method of claim 15, wherein the introducers are removed from the second prosthesis after the second prosthesis is passed over the connectors.

17. The method of claim 8, further comprising advancing one or more knots down the leaders after directing the second prosthesis over the leaders.

* * * * *